(12) United States Patent
Bava

(10) Patent No.: US 12,188,085 B2
(45) Date of Patent: Jan. 7, 2025

(54) THREE-DIMENSIONAL SPATIAL TRANSCRIPTOMICS WITH SEQUENCING READOUT

(71) Applicant: 10x Genomics, Inc., Pleasanton, CA (US)

(72) Inventor: Felice Alessio Bava, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 756 days.

(21) Appl. No.: 17/192,746

(22) Filed: Mar. 4, 2021

(65) Prior Publication Data

US 2021/0277460 A1 Sep. 9, 2021

Related U.S. Application Data

(60) Provisional application No. 62/985,622, filed on Mar. 5, 2020.

(51) Int. Cl.
*C12Q 1/6869* (2018.01)
*C12Q 1/6832* (2018.01)

(52) U.S. Cl.
CPC ......... *C12Q 1/6869* (2013.01); *C12Q 1/6832* (2013.01)

(58) Field of Classification Search
CPC .................... C12Q 1/6869; C12Q 1/6832
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,512,462 A | 4/1996 | Cheng |
| 5,599,675 A | 2/1997 | Brenner |
| 5,635,352 A | 6/1997 | Urdea et al. |
| 5,695,940 A | 12/1997 | Drmanac et al. |
| 5,750,341 A | 5/1998 | Macevicz |
| 6,054,274 A | 4/2000 | Sampson et al. |

(Continued)

FOREIGN PATENT DOCUMENTS

| | | |
|---|---|---|
| WO | WO 2005/065814 | 7/2005 |
| WO | WO 2006/064199 | 6/2006 |

(Continued)

OTHER PUBLICATIONS

Liu et al. (Jan. 1, 2019a). High-spatial-resolution multi-omics Atlas sequencing of mouse embryos via deterministic barcoding in tissue. bioRxiv. biorxiv.org/content/10.1101/788992v1.full (Year: 2019).*

(Continued)

*Primary Examiner* — Aaron A Priest
*Assistant Examiner* — Tian Yu
(74) *Attorney, Agent, or Firm* — MORRISON & FOERSTER LLP

(57) ABSTRACT

In some embodiments described herein are methods for three-dimensional analysis of a biological sample, comprising migrating a population of spatial probes into the biological sample in each of three dimensions, wherein each spatial probe comprises a targeting domain and a migration domain. Also provided are kits and compositions for use according to any of the methods described herein.

16 Claims, 17 Drawing Sheets

(56) References Cited

U.S. PATENT DOCUMENTS

| | | |
|---|---|---|
| 6,172,218 B1 | 1/2001 | Brenner |
| 6,210,891 B1 | 4/2001 | Nyren et al. |
| 6,258,568 B1 | 7/2001 | Nyren et al. |
| 6,265,552 B1 | 7/2001 | Schatz |
| 6,274,320 B1 | 8/2001 | Rothberg et al. |
| 6,291,187 B1 | 9/2001 | Kingsmore et al. |
| 6,306,597 B1 | 10/2001 | Macevicz |
| 6,323,009 B1 | 11/2001 | Lasken et al. |
| 6,344,329 B1 | 2/2002 | Lizardi et al. |
| 6,368,801 B1 | 4/2002 | Faruqi |
| 6,391,937 B1 | 5/2002 | Beuhler et al. |
| 6,534,266 B1 | 3/2003 | Singer |
| 6,969,488 B2 | 11/2005 | Bridgham et al. |
| 7,001,792 B2 | 2/2006 | Sauer et al. |
| 7,057,026 B2 | 6/2006 | Barnes et al. |
| 7,255,994 B2 | 8/2007 | Lao |
| 7,264,929 B2 | 9/2007 | Rothberg et al. |
| 7,473,767 B2 | 1/2009 | Dimitrov |
| 7,534,991 B2 | 5/2009 | Miller et al. |
| 7,555,155 B2 | 6/2009 | Levenson et al. |
| 7,655,898 B2 | 2/2010 | Miller |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,512,422 B2 | 12/2016 | Barnard et al. |
| 9,541,504 B2 | 1/2017 | Hoyt |
| 9,551,032 B2 | 1/2017 | Landegren et al. |
| 9,624,538 B2 | 4/2017 | Church et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,889,422 B2 | 2/2018 | Smith et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,416,116 B2* | 9/2019 | Chung ............... G01N 1/31 |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,459,603 B2 | 10/2022 | Tyagi et al. |
| 2005/0158716 A1 | 7/2005 | Dahlberg et al. |
| 2006/0188901 A1 | 8/2006 | Barnes et al. |
| 2006/0240439 A1 | 10/2006 | Smith et al. |
| 2006/0281109 A1 | 12/2006 | Barr et al. |
| 2007/0166705 A1 | 7/2007 | Milton et al. |
| 2010/0055733 A1 | 3/2010 | Lutolf et al. |
| 2011/0223585 A1 | 9/2011 | Gullberg et al. |
| 2011/0256183 A1 | 10/2011 | Frank et al. |
| 2012/0270305 A1 | 10/2012 | Reed et al. |
| 2013/0079232 A1 | 3/2013 | Kain et al. |
| 2013/0260372 A1 | 10/2013 | Buermann et al. |
| 2013/0288249 A1 | 10/2013 | Gullbert |
| 2013/0323729 A1 | 12/2013 | Landegren et al. |
| 2016/0024555 A1 | 1/2016 | Church et al. |
| 2016/0108458 A1 | 4/2016 | Frei et al. |
| 2016/0305856 A1 | 10/2016 | Boyden et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0219465 A1 | 8/2017 | Desseroth et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0245142 A1* | 8/2018 | So ................. C12Q 1/6816 |
| 2018/0251833 A1 | 9/2018 | Daugharthy et al. |
| 2018/0320226 A1 | 11/2018 | Church et al. |
| 2019/0017106 A1* | 1/2019 | Frisen ................. G16B 30/00 |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1* | 4/2019 | Deisseroth ........... C12Q 1/6806 |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0194709 A1 | 6/2019 | Church et al. |
| 2019/0218608 A1 | 7/2019 | Daugharthy et al. |
| 2019/0233878 A1 | 8/2019 | Delaney et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0323088 A1 | 10/2019 | Boutet et al. |
| 2019/0339203 A1 | 11/2019 | Miller et al. |
| 2019/0367969 A1 | 12/2019 | Belhocine |
| 2020/0002763 A1 | 1/2020 | Belgrader et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |

(56) References Cited

U.S. PATENT DOCUMENTS

| | | |
|---|---|---|
| 2021/0017587 A1 | 1/2021 | Cai et al. |
| 2021/0115504 A1 | 4/2021 | Cai et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |

FOREIGN PATENT DOCUMENTS

| | | | |
|---|---|---|---|
| WO | WO 2007/010251 | 1/2007 | |
| WO | WO-2016138496 A1 * | 9/2016 | ............ C12Q 1/6813 |
| WO | WO 2017/143155 | 8/2017 | |
| WO | WO-2018217862 A1 * | 11/2018 | ............. C12N 15/10 |
| WO | WO 2019/199579 | 10/2019 | |
| WO | WO 2020/076976 | 4/2020 | |
| WO | WO 2020/076979 | 4/2020 | |
| WO | WO 2020/096687 | 5/2020 | |
| WO | WO 2020/099640 | 5/2020 | |
| WO | WO 2020/117914 | 6/2020 | |
| WO | WO 2020/123316 | 6/2020 | |
| WO | WO 2020/123742 | 6/2020 | |
| WO | WO 2020/142490 | 7/2020 | |
| WO | WO 2020/240025 | 12/2020 | |
| WO | WO 2020/254519 | 12/2020 | |
| WO | WO 2021/123282 | 6/2021 | |
| WO | WO 2021/123286 | 6/2021 | |
| WO | WO 2021/155063 | 8/2021 | |
| WO | WO 2021/168326 | 8/2021 | |

OTHER PUBLICATIONS

Salimullah et al. High-throughput three-dimensional gel electrophoresis for versatile utilities: a stacked slice-gel system for separation and reactions (4SR). Genomics Proteomics Bioinformatics. Feb. 2006;4(1):26-33. doi: 10.1016/S1672-0229(06)60013-2. (Year: 2006).*

(With supplementary) Wang et al. Three-dimensional intact-tissue sequencing of single-cell transcriptional states. Science. Jul. 27, 2018;361(6400): eaat5691. without supplementary filed as IDS #262, 08/23/202 (Year: 2018).*

Liu et al., High-Spatial-Resolution Multi-Omics Atlas Sequencing of Mouse Embryos via Deterministic Barcoding in Tissue; bioRxiv (Jan. 1, 2019a), doi.org/10.1101/788992 (Year: 2019).*

Baner et al., "Signal amplification of padlock probes by rolling circle replication," Nucleic Acids Res. (1998) 26(22):5073-5078.

Bibikova et al., "Quantitative gene expression profiling in formalin-fixed, paraffin-embedded tissues using universal bead arrays," Am J Pathol. Nov. 2004; 165(5):1799-807.

Bolognesi et al., "Multiplex Staining by Sequential Immunostaining and Antibody Removal on Routine Tissue Sections," J. Histochem. Cytochem. (2017); 65(8): 431-444.

Capodieci et al., "Gene expression profiling in single cells within tissue," Nat Methods. (2005) 2(9): 663-5.

Chen et al., "Nanoscale imaging of RNA with expansion microscopy," Nat Methods. (2016) 13:679-684.

Chen et al., "Expansion Microscopy," Science (2015) 347(6221):543-548.

Cockroft et al., "A single-molecule nanopore device detects DNA polymerase activity with single-nucleotide resolution," J Am Chem Soc. (2008) 130(3): 818-20.

Conze et al., "Single molecule analysis of combinatorial splicing," Nucleic Acids Res. (2010) 38(16): e163.

Deamer et al., "Characterization of nucleic acids by nanopore analysis," Acc Chem Res. (2002) 35(10): 817-25.

Deamer et al., "Nanopores and nucleic acids: prospects for ultrarapid sequencing," Trends Biotechnol. (2000) 18(4): 147-51.

Dean et al., "Rapid Amplification Of Plasmid And Phage DNA Using Phi29 DNA Polymerase And Multiply-Primed Rolling Circle Amplification," Genome Research (2001) 11:1095-1099.

Eagen, K. "Principles of Chromosome Architecture Revealed by Hi-C," Trends Biochem Sci. (2018) 43(6): 469-478.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Faruqi et al., "High-throughput genotyping of single nucleotide polymorphisms with rolling circle amplification," BMC Genomics. (2001) 2:4.

Femino et al., "Visualization of single RNA transcripts in situ," Science. (1998) 280(5363): 585-90.

Forcucci et al., "All-plastic miniature fluorescence microscope for point-of-care readout of bead-based bioassays," J Biomed Opt. (2015) 20(10): 105010.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Glass et al., "SIMPLE: a sequential immunoperoxidase labeling and erasing method," J Histochem Cytochem. (2009) 57(10); 899-905.

Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1): e7. doi: 10.1093/nar/gkn921.

Gunderson et al. "Decoding randomly ordered DNA arrays." Genome research 14.5 (2004): 870-877.

Han et al., "Quantum-dot-tagged microbeads for multiplexed optical coding of biomolecules," Nat Biotechnol. (2001) 19(7): 631-5.

Healy et al., "Nanopore-based single-molecule DNA analysis," Nanomedicine (Lond). (2007) 2(4): 459-81.

Itzkovitz et al., "Validating Transcripts with Probes and Imaging Technology," Nat Methods. (2011) 8(4 Suppl): S12-S19.

Itzkovitz et al., "Single-molecule transcript counting of stem-cell markers in the mouse intestine," Nat Cell Biol. (2011) 14(1): 106-14.

Jamur et al., "Permeabilization of cell membranes," Method Mol. Biol. (2010) 588: 63-66 (abstract only).

Korlach et al. "Selective aluminum passivation for targeted immobilization of single DNA polymerase molecules in zero-mode waveguide nanostructures." *Proceedings of the National Academy of Sciences* 105.4 (2008): 1176-1181.

Lagunavicius et al., "Novel application of Phi29 DNA polymerase: RNA detection and analysis in vitro and in situ by target RNA-primed RCA," RNA. (2009) 15(5):765-71.

Larsson et al. "In situ detection and genotyping of individual mRNA molecules," Nat Methods. (2010) 7(5):395-397.

Levene et al. "Zero-mode waveguides for single-molecule analysis at high concentrations." *science* 299.5607 (2003): 682-686.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Li et al., "DNA molecules and configurations in a solid-state nanopore microscope," Nat Mater. (2003) 2(9): 611-615.

Lin et al., "Highly multiplexed imaging of single cells using a high-throughput cyclic immunofluorescence method," Nat Commun. (2015) 6:8390.

(56) References Cited

OTHER PUBLICATIONS

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Lizardi et al., "Mutation detection and single-molecule counting using isothermal rolling-circle amplification," Nat Genet. (1998) 19(3): 225-232.

Lundquist et al. "Parallel confocal detection of single molecules in real time." Optics letters 33.9 (2008): 1026-1028.

Maierhorfer et al., "Multicolor deconvolution microscopy of thick biological specimens," Am J Pathol. (2003) 162(2): 373-9.

McGinn et al., "New technologies for DNA analysis—a review of the READNA Project," N Biotechnol. (2016) 33(3): 311-30. doi: 10.1016/j.nbt.2015.10.003.

Meade et al. "Multiplexed DNA detection using spectrally encoded porous SiO2 photonic crystal particles," Anal Chem. (2009) 81(7): 2618-25.

Miele et al. "Mapping cis-and trans-chromatin interaction networks using chromosome conformation capture (3C)." The nucleus. Humana Press, Totowa, NJ, 2008. 105-121.

Mohsen et al., "The Discovery of Rolling Circle Amplification and Rolling Circle Transcription," Acc Chem Res. (2016) 49(11): 2540-2550.

Nallur et al., "Signal amplification by rolling circle amplification on DNA microarrays," Nucleic Acids Res. (2001) 29(23): e118.

Payne et al. "In situ genome sequencing resolves DNA sequence and structure in intact biological samples," Science. (2021) 371(6532): eaay3446. doi: 10.1126/science.aay3446. Epub Dec. 31, 2020.

Pirici et al., "Antibody elution method for multiple immunohistochemistry on primary antibodies raised in the same species and of the same subtype," J Histochem Cytochem. (2009) 57(6); 567-75.

Raab et al., "Human tRNA genes function as chromatin insulators," EMBO J. (2012) 31(2): 330-50.

Raj et al., "Imaging individual mRNA molecules using multiple singly labeled probes," Nat Methods. (2008) 5(10): 877-879.

Rajeswari et al., "Multiple pathogen biomarker detection using an encoded bead array in droplet PCR," J Microbiol Methods. (2017) 139: 22-28.

Ronaghi et al., "A sequencing method based on real-time pyrophosphate," Science. (1998) 281(5375): 363, 365.

Ronaghi et al., "Real-time DNA sequencing using detection of pyrophosphate release," Anal Biochem. (1996) 242(1): 84-9.

Ronaghi, "Pyrosequencing sheds light on DNA sequencing," Genome Res. (2001) 11(1): 3-11.

Rouhanifard et al. "ClampFISH detects individual nucleic acid molecules using click chemistry-based amplification," Nat Biotechnol. (2018) 17 pages. doi: 10.1038/nbt.4286.

Schweitzer et al., "Multiplexed protein profiling on microarrays by rolling-circle amplification," Nature Biotech. (2002) 20:359-365.

Schweitzer et al. "Immunoassays with rolling circle DNA amplification: A versatile platform for ultrasensitive antigen detection," Proc. Natl Acad. Sci. USA (2000) 97:10113-119.

Shendure et al, "Accurate multiplex polony sequencing of an evolved bacterial genome," Science (2005) 309(5741); 1728-1732.

Simonis et al., "Nuclear organization of active and inactive chromatin domains uncovered by chromosome conformation capture-on-chip (4C)," Nat Genet. (2006) 38(11): 1348-54.

Soderberg et al. "Characterizing proteins and their interactions in cells and tissues using the in situ proximity ligation assay." *Methods* 45.3 (2008): 227-232.

Soni et al., "Progress toward ultrafast DNA sequencing using solid-state nanopores," Clin Chem. (2007) 53(11): 1996-2001.

Sun et al., "Composite organic-inorganic nanoparticles as Raman labels for tissue analysis," Nano Lett. (2007) 7(2): 351-6.

Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.

Wählby et al., "Sequential immunofluorescence staining and image analysis for detection of large numbers of antigens in individual cell nuclei," Cytometry. (2002) 47(1): 32-41.

Wang et al., "Three-dimensional intact-tissue sequencing of single-cell transcriptional states," Science. (2018) 361(6400): eaat5691.

Weibrecht et al., "Simultaneous visualization of both signaling cascade activity and end-point gene expression in single cells," PLoS One. (2011) 6(5): e20148.

Wilson et al., "Encoded microcarriers for high-throughput multiplexed detection," Angew Chem Int Ed Engl. (2006) 18;45(37): 6104-17.

Wu, C. et al. "RollFISH Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.

Zhao et al., "Advances of multiplex and high throughput biomolecular detection technologies based on encoding microparticles," Sci China Chem. (2011) 54(8):1185.

\* cited by examiner

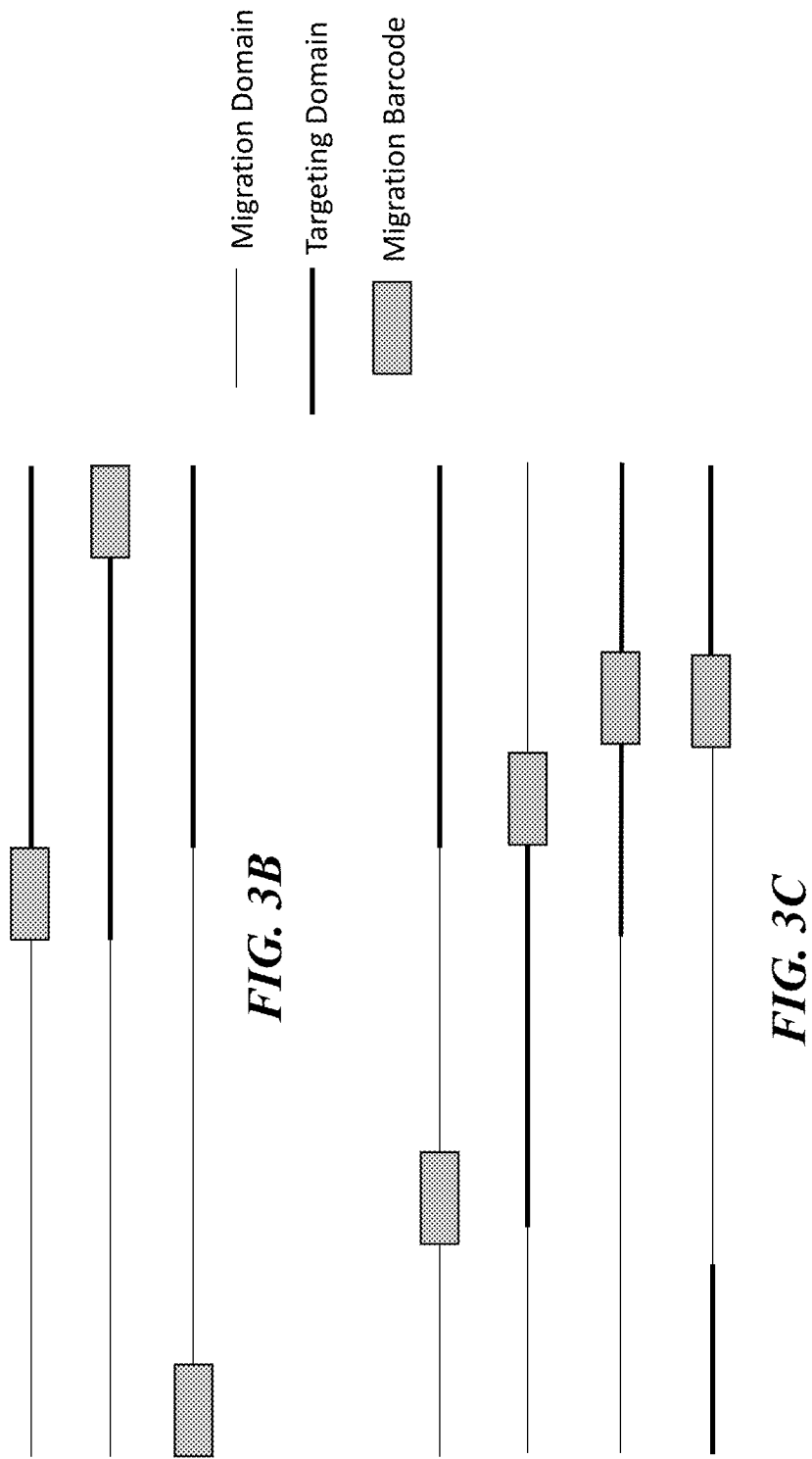

THREE-DIMENSIONAL SPATIAL TRANSCRIPTOMICS WITH SEQUENCING READOUT

CROSS-REFERENCE TO RELATED APPLICATION

This application claims priority to U.S. Provisional Patent Application No. 62/985,622, filed Mar. 5, 2020, entitled "THREE-DIMENSIONAL SPATIAL TRANSCRIPTOMICS WITH SEQUENCING READOUT," which is herein incorporated by reference in its entirety for all purposes.

FIELD

The present disclosure relates in some aspects to methods for analyzing locations of analytes in a three-dimensional space of a sample.

BACKGROUND

Intact tissues can be interrogated in three dimensions by spatial transcriptomics (see Wang et al., Science 361, 380, 2018). Current methods are mainly associated with microscopy-based technologies as a readout, to determine locations of specific RNAs within a multidimensional space.

Improved methods for determining and quantifying relative locations of specific cellular analytes, including RNAs, within a three-dimensional space would be useful. The present disclosure addresses this and other needs.

BRIEF SUMMARY

In some aspects, provided herein is a method for three-dimensional analysis of a biological sample, comprising: (a) in a first dimension, migrating a first population of spatial probes into the biological sample, wherein a first-dimension spatial probe of the first population is targeted to a target molecule immobilized in the biological sample; (b) in a second dimension, migrating a second population of spatial probes into the biological sample, wherein a second-dimension spatial probe of the second population is targeted to the target molecule and/or the first-dimension spatial probe targeted thereto; (c) in a third dimension, migrating a third population of spatial probes into the biological sample, wherein a third-dimension spatial probe of the third population is targeted to the target molecule, the first-dimension spatial probe targeted thereto, and/or the second-dimension spatial probe targeted thereto, wherein the first-dimension spatial probe, the second-dimension spatial probe, and the third-dimension spatial probe each comprises: (i) a targeting domain, (ii) a migration domain corresponding to a location in the biological sample to which the spatial probe is migrated in the respective dimension, and optionally (iii) a migration barcode sequence that identifies the migration domain; d) generating a product in the biological sample, the product comprising: (1) a sequence or complement thereof of the migration domains and/or the migration barcode sequences of the first-dimension spatial probe, the second-dimension spatial probe, and the third-dimension spatial probe; and (2) a sequence corresponding to the target molecule; and (e) determining a sequence of the product, thereby identifying the location of the target molecule in a three-dimensional space in the biological sample. In some embodiments, by migrating the spatial probes of the first, second, and third populations in the biological sample, the spatial probes of each population are separated and distributed in the biological sample.

In any of the preceding embodiments, the first-dimension, second-dimension, and/or third-dimension spatial probe can each comprise the migration domain and the migration barcode sequence. In any of the preceding embodiments, the migration domain or a portion thereof can be cleaved from its spatial probe once the spatial probe is migrated to a location in the respective dimension. In any of the preceding embodiments, the migration domain or a portion thereof can be cleaved from its spatial probe once the spatial probe is targeted to the target molecule, the first-dimension spatial probe targeted thereto, and/or the second-dimension spatial probe targeted thereto. In any of the preceding embodiments, the migration domain or a portion thereof can be cleaved from the product once it is generated in the biological sample, for instance, in order to reduce the size of the product for sequencing analysis but without separating spatial information encoded in the sequences of the spatial probes from information of the target molecule. In some embodiments, the product can be processed (e.g., cleaved) but still comprise (1) a sequence or complement thereof of the migration barcode sequences of the first-dimension spatial probe, the second-dimension spatial probe, and the third-dimension spatial probe; and (2) a sequence corresponding to the target molecule; In some embodiments, the determining of the sequence of the product is not performed in situ in the biological sample or a matrix embedding the sample. In some embodiments, the product can be released, migrated, or isolated from the biological sample prior to being processed for sequencing, such as sequencing library construction and obtaining sequencing reads by next-generation sequencing techniques known in the art.

In any of the preceding embodiments, the migration barcode sequence of the spatial probe can correspond to the length of the spatial probe and/or the length of the migration domain of the spatial probe.

In any of the preceding embodiments, the targeting domain can comprise a nucleic acid sequence capable of hybridizing to the target molecule or one or more intermediate probes directly or indirectly bound to the target molecule.

In any of the preceding embodiments, the targeting domain can comprise a gene-specific nucleic acid sequence, a common nucleic acid sequence, a degenerate or partially degenerate nucleic acid sequence, a universal nucleic acid sequence, or any combination thereof.

In any of the preceding embodiments, the targeting domains of first-dimension spatial probes for two or more different target molecules can be different, optionally wherein the target domain of each first-dimension spatial probe is specific for its corresponding target molecule.

In any of the preceding embodiments, the targeting domains of second-dimension spatial probes for two or more different target molecules can be the same or different, optionally wherein the targeting domains of third-dimension spatial probes for two or more different target molecules are the same or different.

In any of the preceding embodiments, the targeting domains of first-dimension spatial probes for two or more different target molecules can share a common sequence, optionally wherein the target domains of first-dimension spatial probes for two or more different target molecules are identical.

In any of the preceding embodiments, the common sequence of the first-dimension spatial probes for two or more different target molecules can comprise an oligo(dT) sequence.

In any of the preceding embodiments, the common sequence of the first-dimension spatial probes for two or more different target molecules can be (i) complementary to a common adapter sequence in target-binding primary probes for two or more different target molecules or (ii) complementary to a splint that bridges a target-binding primary probe and a first-dimension spatial probe.

In any of the preceding embodiments, the targeting domains of second-dimension spatial probes for two or more different target molecules can share a common sequence, optionally wherein the common sequence is (i) complementary to a common adapter sequence in first-dimension spatial probes for two or more different target molecules or (ii) complementary to a splint that bridges a first-dimension spatial probe and a second-dimension spatial probe.

In any of the preceding embodiments, the targeting domains of third-dimension spatial probes for two or more different target molecules can share a common sequence, optionally wherein the common sequence is (i) complementary to a common adapter sequence in first-dimension spatial probes and/or second-dimension spatial probes for two or more different target molecules, (ii) complementary to a splint that bridges a first-dimension spatial probe and a third-dimension spatial probe, or (iii) complementary to a splint that bridges a second-dimension spatial probe and a third-dimension spatial probe.

In any of the preceding embodiments, the target molecule can be an RNA, a probe directly or indirectly bound thereto, an amplification product of the RNA or the probe, or a probe directly or indirectly bound to the amplification product.

In some of any such embodiments, the first, second, and third populations can each comprise spatial probes that migrates differently in the sample. In any of the preceding embodiments, the first, second, and third populations can each comprise spatial probes having different lengths. In any of the preceding embodiments, the first, second, and third populations can each comprise spatial probes having migration domains of different lengths.

In any of the preceding embodiments, the location in the biological sample to which the spatial probe is migrated in the respective dimension can be correlated with the length of the spatial probe and/or the length of the migration domain of the spatial probe.

In any of the preceding embodiments, the spatial probe can further comprise a barcode sequence that identifies the targeting domain.

In any of the preceding embodiments, spatial probes of the first population or a subset thereof can share a barcode sequence corresponding to or identifies the first population or subset thereof.

In any of the preceding embodiments, spatial probes of the second population or a subset thereof can share a barcode sequence corresponding to or identifies the second population or subset thereof.

In any of the preceding embodiments, spatial probes of the third population or a subset thereof can share a barcode sequence corresponding to or identifies the third population or subset thereof.

In any of the preceding embodiments, the first, second, and/or third populations can comprise spatial probes targeting different target molecules. In some embodiments, the first population of spatial probes targets different target molecules from the second and/or third population of spatial probes. In some embodiments, the second population of spatial probes targets different target molecules from the third population of spatial probes.

In any of the preceding embodiments, the length of the migration domain of the spatial probe can be variable while the length of the rest of the spatial probe is constant among spatial probes of the first population, the second population, and/or the third population.

In any of the preceding embodiments, the length of the targeting domain and the migration barcode sequence of the spatial probe can be constant among spatial probes of the first population, the second population, and/or the third population.

In any of the preceding embodiments, the migration domain of the spatial probe can be cleavable from the spatial probe.

In any of the preceding embodiments, the migration in steps (a), (b), and/or (c) can be performed using passive migration, active migration, or any combination thereof in any order.

In any of the preceding embodiments, the active migration can comprise using an electric field, a magnetic field, a charged gradient, or any combination thereof in any order.

In any of the preceding embodiments, the migration in steps (a), (b), and/or (c) can comprise migration in a linear direction.

In any of the preceding embodiments, the migration in steps (a), (b), and/or (c) can comprise migration in a non-linear direction.

In any of the preceding embodiments, in the migrating step of (a), the first-dimension spatial probes can be migrated while the target molecule is not migrated.

In any of the preceding embodiments, the migrating step of (a) can comprise electrophoresis to distribute the first-dimension spatial probes by size in the biological sample in the first dimension.

In any of the preceding embodiments, the method can further comprise ceasing migration to allow the first-dimension spatial probes to directly or indirectly bind to target molecules in the corresponding locations to which they are migrated in the biological sample.

In any of the preceding embodiments, the method can further comprise removing first-dimension spatial probe molecules that non-specifically bind or do not bind to the target molecules.

In any of the preceding embodiments, the method can further comprise cleaving the migration domain from the first-dimension spatial probe after the migration in step (a).

In any of the preceding embodiments, the method can further comprise anchoring the first-dimension spatial probes in the corresponding locations to which they are migrated in the biological sample.

In any of the preceding embodiments, the first-dimension spatial probes can be anchored to target molecules and/or other endogenous or exogenous molecules in the corresponding locations to which they are migrated in the biological sample. In some embodiments, the anchored first-dimension spatial probes do not migrate during electrophoresis of the second-dimension spatial probes or the third-dimension spatial probes.

In any of the preceding embodiments, the anchoring can comprise hybridization, ligation, primer extension, cross-linking, or any combination thereof in any order.

In any of the preceding embodiments, the anchoring can comprise hybridization followed by ligation, with or without gap filling prior to the ligation.

In any of the preceding embodiments, the ligation can comprise enzymatic ligation, chemical ligation, or any combination thereof in any order, optionally wherein the chemical ligation comprises click chemistry.

In any of the preceding embodiments, in the migrating step of (b), the second-dimension spatial probes can be migrated while the target molecule and the first-dimension spatial probe are not.

In any of the preceding embodiments, the migrating step of (b) can comprise electrophoresis in the biological sample to distribute the second-dimension spatial probes by size in the second dimension.

In any of the preceding embodiments, the method can further comprise ceasing migration to allow the second-dimension spatial probes to directly or indirectly bind to target molecules and/or first-dimension spatial probe molecules in the corresponding locations to which they are migrated in the biological sample.

In any of the preceding embodiments, the method can further comprise removing second-dimension spatial probe molecules that non-specifically bind or do not bind to the target molecules and/or the first-dimension spatial probe molecules.

In any of the preceding embodiments, the method can further comprise cleaving the migration domain of the second-dimension spatial probe from the second-dimension spatial probe after the migration in step (b).

In any of the preceding embodiments, the method can further comprise anchoring the second-dimension spatial probes in the corresponding locations to which they are migrated in the biological sample.

In any of the preceding embodiments, the second-dimension spatial probes can be anchored to target molecules, first-dimension spatial probe molecules, and/or other endogenous or exogenous molecules in the corresponding locations to which they are migrated in the biological sample. In some embodiments, the anchored second-dimension spatial probes do not migrate during electrophoresis of the third-dimension spatial probes.

In any of the preceding embodiments, the anchoring can comprise hybridization, ligation, primer extension, cross-linking, or any combination thereof in any order.

In any of the preceding embodiments, the anchoring can comprise hybridization followed by ligation, with or without gap filling prior to the ligation.

In any of the preceding embodiments, the ligation can comprise enzymatic ligation, chemical ligation, or any combination thereof in any order, optionally wherein the chemical ligation comprises click chemistry.

In any of the preceding embodiments, in the migrating step of (c), the third-dimension spatial probes can be migrated while the target molecule, the first-dimension spatial probe, and the second-dimension spatial probe are not.

In any of the preceding embodiments, the migrating step of (c) can comprise electrophoresis in the biological sample to distribute the third-dimension spatial probes by size in the third dimension.

In any of the preceding embodiments, the method can further comprise ceasing migration to allow the third-dimension spatial probes to directly or indirectly bind to target molecules, first-dimension spatial probe molecules, and/or second-dimension spatial probe molecules in the corresponding locations to which they are migrated in the biological sample.

In any of the preceding embodiments, the method can further comprise removing third-dimension spatial probe molecules that non-specifically bind or do not bind to the target molecules, the first-dimension spatial probe molecules, and/or the second-dimension spatial probe molecules.

In any of the preceding embodiments, the method can further comprise cleaving the migration domain of the third-dimension spatial probe from the third-dimension spatial probe after the migration in step (c).

In any of the preceding embodiments, the method can further comprise anchoring the third-dimension spatial probes in the corresponding locations to which they are migrated in the biological sample.

In any of the preceding embodiments, the third-dimension spatial probes can be anchored to target molecules, first-dimension spatial probe molecules, second-dimension spatial probe molecules, and/or other endogenous or exogenous molecules in the corresponding locations to which they are migrated in the biological sample.

In any of the preceding embodiments, the anchoring can comprise hybridization, ligation, primer extension, cross-linking, or any combination thereof in any order.

In any of the preceding embodiments, the anchoring can comprise hybridization followed by ligation, with or without gap filling prior to the ligation.

In any of the preceding embodiments, the ligation can comprise enzymatic ligation, chemical ligation, or any combination thereof in any order, optionally wherein the chemical ligation comprises click chemistry.

In any of the preceding embodiments, the method can further comprise repeating the migrating step in (a) using the same or different first population of spatial probes, optionally wherein the migrating step in (a) is repeated prior to the migrating step in (b).

In any of the preceding embodiments, the method can further comprise repeating the migrating step in (b) using the same or different second population of spatial probes, optionally wherein the migrating step in (b) is repeated prior to the migrating step in (c).

In any of the preceding embodiments, the method can further comprise repeating the migrating step in (c) using the same or different third population of spatial probes, optionally wherein the migrating step in (c) is repeated prior to generate the product in (d).

In any of the preceding embodiments, the method can further comprise repeating the migrating steps in (a)-(c) using the same or different first, second, or third populations of spatial probes.

In any of the preceding embodiments, the method can further comprise repeating the migrating steps in (a)-(c) and the generating step in (d) using the same or different first, second, or third populations of spatial probes.

In any of the preceding embodiments, the method can further comprise releasing, removing, or isolating the product from the biological sample prior to the determining step of (e).

In any of the preceding embodiments, the determining step of (e) can comprise sequential fluorescence hybridization, sequencing by synthesis, sequencing by ligation, sequencing by hybridization, sequencing by binding, nanopore sequencing, solid-state sequencing, electronic sequencing, digital sequencing, or any combination thereof in any order.

In any of the preceding embodiments, the spatial probe can further comprise a detectable moiety. In some embodiments, the spatial probes are not labeled with a detectable moiety.

In any of the preceding embodiments, the method can further comprise imaging the biological sample. In some embodiments, the method does not include imaging the spatial probes in the biological sample.

In any of the preceding embodiments, the target molecule can be a target nucleic acid or a target protein.

In any of the preceding embodiments, the target molecule can be a viral or cellular DNA or RNA.

In any of the preceding embodiments, the target molecule can be endogenous in the biological sample.

In any of the preceding embodiments, the target molecule can be a product of an endogenous molecule in the biological sample.

In any of the preceding embodiments, the target molecule can be comprised in a labelling agent that directly or indirectly binds to an analyte in the biological sample, or is comprised in a product of the labelling agent. In some embodiments, the labelling agent can comprise a reporter oligonucleotide, optionally wherein the reporter oligonucleotide comprises one or more barcode sequences and the product of the labelling agent comprises one or a plurality of copies of the one or more barcode sequences.

In any of the preceding embodiments, the target molecule immobilized in the biological sample can be a rolling circle amplification (RCA) product of a circular or circularizable probe or probe set that hybridizes to a nucleic acid molecule in the biological sample.

In any of the preceding embodiments, the labelling agent can comprise a binding moiety that directly or indirectly binds to a non-nucleic acid analyte in the biological sample and the reporter oligonucleotide in the labelling agent can identify the binding moiety and/or the non-nucleic acid analyte.

In any of the preceding embodiments, the binding moiety of the labelling agent can comprise an antibody or antigen binding fragment thereof that directly or indirectly binds to a protein analyte, and the nucleic acid molecule in the biological sample is a rolling circle amplification (RCA) product of a circular or circularizable probe or probe set that hybridizes to a reporter oligonucleotide of the labelling agent.

In any of the preceding embodiments, the biological sample can comprise cells or cellular components. In any of the preceding embodiments, the biological sample can be a tissue sample. In any of the preceding embodiments, the biological sample can be fixed. In any of the preceding embodiments, the biological sample may not be fixed. In any of the preceding embodiments, the biological sample can be a formalin-fixed, paraffin-embedded (FFPE) sample, a frozen tissue sample, or a fresh tissue sample. In any of the preceding embodiments, the biological sample can be permeabilized. In any of the preceding embodiments, the biological sample can be processed or cleared. In some embodiments, the biological sample is cleared before being contacted with the first, second, and third populations of spatial probes.

In any of the preceding embodiments, the biological sample can be embedded in a matrix. In some embodiments, the matrix can be a hydrogel. In any of the preceding embodiments, one or more molecules in the biological sample are anchored to the matrix. In any of the preceding embodiments, the biological sample and/or the matrix can be crosslinked.

In some embodiments, provided herein is a method for three-dimensional analysis of a biological sample, comprising: (a) generating target nucleic acid molecules in the biological sample, wherein the target nucleic acid molecules are (i) a product of an endogenous nucleic acid molecule, (ii) a product of one or more nucleic acid probes that directly or indirectly hybridize to the endogenous nucleic acid molecule or to the product of (i), or (iii) a product of the product of (i) or (ii); (b) embedding the biological sample in a matrix, wherein the target nucleic acid molecules are crosslinked to the matrix, thereby immobilizing the target nucleic acid molecules in the matrix-embedded biological sample; (c) electrophoresing a first population of spatial probes for distribution by size in a first dimension, wherein a first-dimension spatial probe of the first population is targeted to a target nucleic acid molecule immobilized in the matrix-embedded biological sample; (d) electrophoresing a second population of spatial probes for distribution by size in a second dimension, wherein a second-dimension spatial probe of the second population is targeted to the target nucleic acid molecule and/or the first-dimension spatial probe targeted thereto; (e) electrophoresing a third population of spatial probes for distribution by size in a third dimension, wherein a third-dimension spatial probe of the third population is targeted to the target nucleic acid molecule, the first-dimension spatial probe targeted thereto, and/or the second-dimension spatial probe targeted thereto, wherein the first-dimension spatial probe, the second-dimension spatial probe, and the third-dimension spatial probe each comprises: (i) a targeting sequence for targeting, (ii) a variable-length sequence corresponding to a location in the matrix-embedded biological sample to which the spatial probe is distributed in the respective dimension, and (iii) a length-barcode sequence corresponding to the variable-length sequence; (f) generating a product in the matrix-embedded biological sample, the product comprising: (1) a sequence or complement thereof of the length-barcode sequences of the first-dimension spatial probe, the second-dimension spatial probe, and the third-dimension spatial probe; and (2) a sequence or complement thereof of the target nucleic acid molecule; (g) releasing, removing, or isolating the product from the matrix-embedded biological sample; and (h) subjecting the released, removed, or isolated product to nucleic acid sequencing, thereby identifying the location of the target nucleic acid molecule in the three dimensions of the matrix-embedded biological sample.

In any of the preceding embodiments, the matrix can comprise a polymer and the target nucleic acid molecules can be rolling circle amplification products comprising modified nucleotides crosslinkable to the polymer.

In any of the preceding embodiments, step (g) can comprises depolymerizing or dissolving the polymer.

In some aspects, provided herein is a kit, comprising: (1) a plurality of X spatial probes each comprising (i) an X targeting sequence for targeting a target nucleic acid molecule, (ii) an X variable-length sequence, and (iii) an X length-barcode sequence corresponding to the X variable-length sequence, wherein the X spatial probes are configured to distribute by size in the direction of electrophoresis such that the X length-barcode sequence of an X spatial probe corresponds to the location of the X spatial probe relative to other X spatial probes in the direction of electrophoresis; (2) a plurality of Y spatial probes each comprising (i) a Y targeting sequence for targeting a target nucleic acid molecule and/or an X spatial probe, (ii) a Y variable-length sequence, and (iii) a Y length-barcode sequence corresponding to the Y variable-length sequence, wherein the Y spatial probes are configured to distribute by size in the direction of electrophoresis such that the Y length-barcode sequence of a Y spatial probe corresponds to the location of the Y spatial probe relative to other Y spatial probes in the direction of electrophoresis; and (3) a plurality of Z spatial probes each comprising (i) a Z targeting sequence for targeting a target nucleic acid molecule, an X spatial probe, and/or a Y spatial probe, (ii) a Z variable-length sequence, and (iii) a Z length-barcode sequence corresponding to the Z variable-length sequence, wherein the Z spatial probes are configured to distribute by size in the direction of electrophoresis such that the Z length-barcode sequence of a Z spatial probe corresponds to the location of the Z spatial probe relative to other Z spatial probes in the direction of electrophoresis.

BRIEF DESCRIPTION OF THE DRAWINGS

In the accompanying drawings, which are incorporated in and constitute a part of the specification, embodiments of the present disclosure are illustrated. It will be appreciated that the embodiments illustrated in the drawings are shown for the purpose of illustration and not for limitation. It will be appreciated that changes, modifications and deviations from the embodiments illustrated in the drawings may be made without departing from the spirit and scope of the present disclosure, as disclosed below.

In FIGS. 1A-1C, lines in the X-dimension (L: large; S: small) and lines in the y-dimension (l: large; s: small) are illustrative of "bands" in which oligonucleotides of the same size migrate together. The line lengths and thicknesses and the distances between lines are for illustration only. The oligonucleotide molecules are not shown.

FIG. 3B and FIG. 3C show exemplary oligonucleotides for migration in the X-, y-, and/or $\mathcal{Z}$-dimension, each comprising a migration domain (e.g., a variable-length sequence; indicated as a thin line), a migration barcode sequence (e.g., a length barcode sequence; indicated as a gray box), and a targeting domain (e.g., a hybridizing sequence; indicated as a thick line). The migration barcode sequence can be between the migration domain and the targeting domain, in the 5' to 3' or 3' to 5' direction (FIG. 3B, top exemplary oligonucleotide). Alternatively, the targeting domain can be between the migration domain and the migration barcode sequence, in the 5' to 3' or 3' to 5' direction (FIG. 3B, middle exemplary oligonucleotide). In other examples, the migration domain can be between the migration barcode sequence and the targeting domain, in the 5' to 3' or 3' to 5' direction (FIG. 3B, bottom exemplary oligonucleotide). Sequences of the migration domain, the migration barcode sequence, and the targeting domain may or may not overlap. The migration domain does not have to be a contiguous sequence. For instance, the targeting domain and/or the migration barcode sequence can be between subdomains of the migration domain (FIG. 3C, first and second exemplary oligonucleotides). Likewise, the targeting domain does not have to be a contiguous sequence. For instance, the migration barcode sequence and/or the migration domain can be between subdomains of the targeting domain (FIG. 3C, third and fourth exemplary oligonucleotides). Further, the migration barcode sequence may comprise subsequences that are separated by other sequences in a linear oligonucleotide (not shown). The exemplary oligonucleotides may comprise one or more other sequences, e.g., a primer binding sequence, an adapter sequence (e.g., a sequencing adapter), one or more other barcode sequences, a UMI, a UID, a tag sequence (e.g., for hybridization to one or more capture oligos), a cleavage site or sequence (e.g., a restriction enzyme recognition sequence and cleavage site), an affinity sequence, etc.

DETAILED DESCRIPTION

Figure 1A:
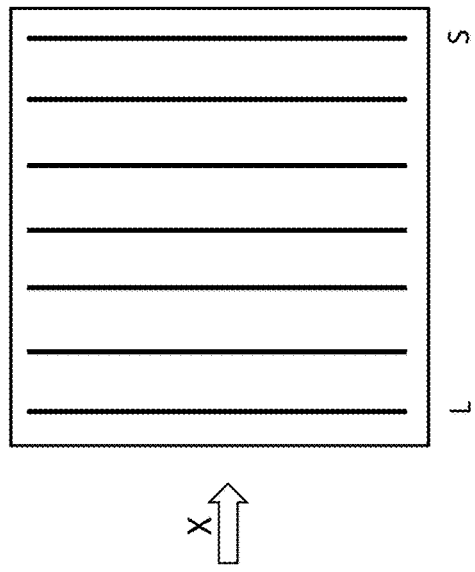
FIG. 1A illustrates exemplary oligonucleotides of different lengths that have been migrated through a medium in an X-dimension and have been separated based on size.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. OVERVIEW

Disclosed herein are reagents, methods, kits, systems, and devices for using nucleotide sequencing as a readout of analyte (e.g., nucleic acid analyte such as DNA or RNA, or protein analyte) location within a multidimensional space. In some embodiments, a method disclosed herein comprises distributing oligonucleotides (e.g., probes) throughout a multidimensional space. In some examples, the oligonucleotides used in the methods are of different lengths and are distributed in the x-, y- and z-dimensions of a three-dimensional space based on their size, e.g., using electrophoresis. The oligonucleotides may comprise nucleotide sequences capable of hybridizing to target nucleic acid molecules (e.g., specific RNAs) or their amplification/ligation products, contained in the three-dimensional space. Retrieval of the oligonucleotides and their associated nucleic acid molecules/amplification/ligation products from the three-dimensional space, and nucleotide sequencing of the oligonucleotides of the complexes, yields a readout of target nucleic acid molecules that are present (e.g., specific RNAs expressed) in the three-dimensional space (specific RNAs are identified by determining the sequence in oligonucleotides that hybridizes to the RNAs). Nucleotide sequencing of the oligonucleotides of the complexes also yields a readout of location in the three-dimensional space (oligonucleotides were distributed by size in each of the x-, y- and z-dimensions during electrophoresis; determination of oligonucleotide size by sequencing, as well as knowledge of the dimension through which the oligonucleotide was electrophoresed, indicates location). Correlation of the target nucleic acid molecules (e.g., specific RNAs) and their locations yields a high-density, quantitative three-dimensional map of relative distribution of target nucleic acid molecules (e.g., specific RNAs) throughout the three-dimensional space.

Disclosed is an oligonucleotide that may include a first barcode nucleotide sequence that is linked to length of the oligonucleotide. The oligonucleotide may include a nucleotide sequence capable of hybridizing to a target nucleic acid molecule including, without limitation: a nucleic acid molecule from a cell (e.g., a cellular RNA); a nucleic acid product generated from a nucleic acid molecule from a cell (e.g., a cellular RNA-derived nucleic acid product, such as a complementary deoxy-ribonucleic acid (cDNA) or an amplification product); a probe hybridized to a nucleic acid molecule from a cell (e.g., a cellular RNA capturing or binding probe); a product generated from a probe hybridized to a nucleic acid molecule from a cell (e.g., a rolling circle amplification product of a padlock probe hybridized to a cellular RNA or cDNA thereof); or any derivative thereof. The oligonucleotide may include one or more other barcode sequences, such as a second barcode nucleotide sequence linked to the nucleotide sequence capable of hybridizing to its target nucleic acid molecule (e.g., a cellular RNA, a cellular RNA capturing probe, or a cellular RNA-derived amplification product). Populations of these so-called "spatial" oligonucleotides (e.g., spatial probes) are disclosed. In some embodiments, at least some subset of spatial probes in the population migrate differently than other spatial probes within the population. Some populations of these oligonucleotides may comprise oligonucleotides of different lengths that comprise the same nucleotide sequence capable of hybridizing to its target nucleic acid molecule (e.g., a cellular RNA, a cellular RNA capturing probe, or a cellular RNA-derived amplification product).

Also disclosed is a population of oligonucleotides of different lengths where the oligonucleotides in the population comprise a first barcode nucleotide sequence linked to length of the oligonucleotides. In some embodiments, oligonucleotides in the population may comprise a hybridizing nucleotide sequence capable of identifying the same target nucleic acid sequence (e.g., a genomic DNA, RNA, or cDNA sequence), which may be present in molecules having identical sequences or different molecules comprising a common target nucleic acid sequence (e.g., DNA variants due to genomic rearrangement, RNA splice variants, etc.). In some embodiments, oligonucleotides in the population may comprise a hybridizing nucleotide sequence capable of identifying the same type of target nucleic acid molecules, e.g., using oligo-T sequences to bind RNA molecules having poly-A tails for transcriptomics analysis. The oligonucleotides in the population may comprise one or more other barcode sequences, such as a second barcode nucleotide sequence linked to the nucleotide sequence capable of identifying the target nucleic acid molecule. In some examples, the oligonucleotides in the population may comprise a third barcode nucleotide sequence common to the oligonucleotides in the population.

Also disclosed is a composition of two or more different populations of oligonucleotides as above, where the different populations of oligonucleotides comprise hybridizing nucleotide sequences capable of identifying different target molecules (e.g., different nucleic acids such as different RNAs). In some examples, the second barcode nucleotide sequences of separate oligonucleotide populations are different.

Also disclosed is a method of migrating a first population of oligonucleotides or composition of oligonucleotides, as above, through a first dimension of a three-dimensional medium to separate individual oligonucleotides by size and immobilizing the separated oligonucleotides of the first population in the medium. In some example methods, a second population or composition of oligonucleotides is migrated through a second dimension of the three-dimensional medium to separate individual oligonucleotides by size and immobilizing the separated oligonucleotides of the second population in the medium. In some example methods, a third population or composition of oligonucleotides is migrated through a third dimension of the three-dimensional medium to separate individual oligonucleotides by size and immobilizing the separated oligonucleotides of the third population in the medium. The three-dimensional medium may be analyzed to determine relative location of the oligonucleotides of one, two or three populations.

In some examples of the method, prior to the migrating, target nucleic acid molecules (e.g., RNA) in the medium may be captured using nucleic acid probes (e.g., RNA capturing probes) and/or production of nucleic acid products derived from the nucleic acid molecules or probes (e.g., RNA-derived extension or amplification products). In some examples of the method where RNA has been captured, after the migrating, the medium may be subjected to conditions where the oligonucleotide sequences capable of hybridizing to a target nucleic acid molecules as described herein (e.g., cellular RNA, a cellular RNA capturing probe, or a cellular RNA-derived extension or amplification product), hybridize to captured target nucleic acid molecules (e.g., RNAs) that have complementary nucleotide sequences. Nucleotide sequences of oligonucleotides that have hybridized may be determined to ascertain location of the target nucleic acid molecules (e.g., RNAs) in the medium.

Also disclosed is an electrophoresis apparatus. The electrophoresis apparatus may include a chamber that can accommodate a three-dimensional tissue sample; sample chambers positioned on one side of, and in communication with, the chamber in each of the x-, y- and z-dimensions of the chamber; and electrodes positioned at each end of the chamber in each of its x-, y- and z-dimensions and configured to direct separate electric fields across a length of each dimension.

In some examples, an exemplary apparatus for electrophoresis may include a central chamber enclosing a volume configured to accept a tissue sample, the chamber additionally configured to hold a volume of electrophoresis buffer into which the tissue sample is submerged; three sample chambers, one positioned adjacent to and contiguous with one side of the central chamber in each of its x-, y- and z-dimensions, the sample chambers configured to hold a sample solution that can be migrated into the entire area of, and across the length, of each dimension of the central chamber; and electrodes positioned to separately and sequentially direct an electric field across each of the x-, y- and z-dimensions of the central chamber to migrate the sample solution from the sample chambers into and through the dimensions of the central chamber containing the tissue sample.

II. SAMPLES AND ANALYTES

A. Samples and Sample Processin.

A sample disclosed herein can be or derived from any biological sample in which analysis of target molecules and their position in two- or three-dimensional space is desired. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can be obtained as a tissue sample, such as a tissue section, biopsy, a core biopsy, needle aspirate, or fine needle aspirate. The sample can be a fluid sample, such as a blood sample, urine sample, or saliva sample, and cells and cellular components therein may be analyzed after placing the cells or cellular components on a substrate. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface and the cells can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include target molecules (e.g., protein, RNA, and/or DNA) in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

The biological sample within the 3D matrix may be cleared of proteins and/or lipids that are not targets of interest. For example, the biological sample can be cleared of proteins (also called "deproteination") by enzymatic proteolysis. The clearing step may be performed before or after covalent immobilization of any target molecules or derivatives thereof.

In some cases, the clearing step is performed after covalent immobilization of target molecules (e.g., RNA or DNA), primers, derivatives of target molecules (e.g., cDNA or amplicons), or intermediate probes (e.g., padlock probes or adapters) to a synthetic 3D matrix. Performing the clearing step after immobilization can enable any subsequent nucleic acid hybridization reactions to be performed under conditions where the sample has been substantially deproteinated, as by enzymatic proteolysis ("protein clearing"). This method can have the benefit of removing ribosomes and other RNA- or nucleic-acid-target-binding proteins from the target molecule (while maintaining spatial location), where the protein component may impede or inhibit probe binding, or may impede or inhibit migration of spatial probes into the sample.

The clearing step can comprise removing non-targets from the 3D matrix. The clearing step can comprise degrading the non-targets. The clearing step can comprise exposing the sample to an enzyme (e.g., a protease) able to degrade a protein. The clearing step can comprise exposing the sample to a detergent.

Proteins may be cleared from the sample using enzymes, denaturants, chelating agents, chemical agents, and the like, which may break down the proteins into smaller components and/or amino acids. These smaller components may be easier to remove physically, and/or may be sufficiently small or inert such that they do not significantly affect the background. Similarly, lipids may be cleared from the sample using surfactants or the like. In some cases, one or more of these agents are used, e.g., simultaneously or sequentially. Non-limiting examples of suitable enzymes include proteinases such as proteinase K, proteases or peptidases, or digestive enzymes such as trypsin, pepsin, or chymotrypsin. Non-limiting examples of suitable denaturants include guanidine HCl, acetone, acetic acid, urea, or lithium perchlorate. Non-limiting examples of chemical agents able to denature proteins include solvents such as phenol, chloroform, guanidinium isocyananate, urea, formamide, etc. Non-limiting examples of surfactants include Triton X-100 (polyethylene glycol p-(1,1,3,3-tetramethylbutyl)-phenyl ether), SDS (sodium dodecyl sulfate), Igepal CA-630, or poloxamers. Non-limiting examples of chelating agents include ethylenediaminetetraacetic acid (EDTA), citrate, or polyaspartic acid. In some embodiments, compounds such as these may be applied to the sample to clear proteins, lipids, and/or other components. For instance, a buffer solution (e.g., containing Tris or tris(hydroxymethyl)aminomethane) may be applied to the sample, then removed.

In some cases, nucleic acids that are not target molecules of interest may also be cleared. These non-target nucleic acids may not be captured and/or immobilized to the 3D matrix, and therefore can be removed with an enzyme to degrade nucleic acid molecules. Non-limiting examples of DNA enzymes that may be used to remove DNA include DNase I, dsDNase, a variety of restriction enzymes, etc. Non-limiting examples of techniques to clear RNA include RNA enzymes such as RNase A, RNase T, or RNase H, or chemical agents, e.g., via alkaline hydrolysis (for example, by increasing the pH to greater than 10). Non-limiting examples of systems to remove sugars or extracellular matrix include enzymes such as chitinase, heparinases, or other glycosylases. Non-limiting examples of systems to remove lipids include enzymes such as lipidases, chemical agents such as alcohols (e.g., methanol or ethanol), or detergents such as Triton X-100 or sodium dodecyl sulfate. In this way, the background of the sample may be removed, which may facilitate analysis of the nucleic acid probes or other targets, e.g., using fluorescence microscopy, or other techniques as described herein.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or padlock probe. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a padlock probe.

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed, e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). In some aspects, the embedding material can be applied to the sample one or more times. Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 µm to about 2 mm.

Additional methods and aspects of hydrogel embedding of biological samples are described for example in Chen et al., *Science* 347(6221):543-548, 2015, the entire contents of which are incorporated herein by reference.

(v) Staining

To facilitate visualization, biological samples can be stained using a wide variety of stains and staining techniques. In some embodiments, for example, a sample can be stained using any number of stains, including but not limited to, acridine orange, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, propidium iodide, rhodamine, or safranine.

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample are known in the art, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347(6221):543-548, 2015.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, Mass.), Label-IT Amine (available from MirusBio, Madison, Wis.) and Label X (described for example in Chen et al., *Nat. Methods* 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly or irreversibly cross-linked prior to, during, or after an assay step disclosed herein. A cross-linking agent includes a chemical agent, or even light, that facilitates the attachment of one molecule to another molecule. Cross-linking agents can be protein-nucleic acid cross-linking agents, nucleic acid-nucleic acid cross-linking agents, and/or protein-protein cross-linking agents. Examples of such agents are known in the art. In some embodiments, a cross-linking agent is a reversible cross-linking agent. In some embodiments, a cross-linking agent is a non-reversible cross-linking agent.

In some embodiments, the sample to be analyzed is contacted with a protein-nucleic acid cross-linking agent, a nucleic acid-nucleic acid cross-linking agent, a protein-protein cross-linking agent or any combination thereof. In some examples, a cross-linker is a reversible cross-linker, such that the cross-linked molecules can be easily separated. In some examples, a cross-linker is a non-reversible cross-linker, such that the cross-linked molecules cannot be easily separated. In some examples, a cross-linker is light, such as UV light. In some examples, a cross linker is light activated. These cross-linkers include formaldehyde, disuccinimidyl glutarate, UV-254, psoralens and their derivatives such as aminomethyltrioxsalen, glutaraldehyde, ethylene glycol bis [succinimidylsuccinate], and other compounds known to those skilled in the art, including those described in the Thermo Scientific Pierce Cross-linking Technical Handbook, Thermo Scientific (2009) as available on the world wide web at piercenet.com/files/1601673_Crosslink_HB_Intl.pdf.

In some embodiments, target molecules can be present within a three dimensional matrix material and covalently attached to the three dimensional matrix material such that the relative position of each target molecule is fixed, i.e. immobilized, within the three dimensional matrix material. In this manner, a three-dimensional matrix of covalently bound target molecules of any desired sequence is provided. Each target molecule has its own three dimensional coordinates within the matrix material and each target molecule represents information. In this manner, a large amount of information can be stored in a three dimensional matrix.

In some embodiments, a cross-linkable probe is used to anchor target molecules to a three dimensional matrix such that the relative position of each target molecule is fixed. In embodiments, the sample is contacted with a poly-dT anchor probe to bind and anchor polyadenylated (polyA) RNAs to the matrix. In some embodiments, the anchor probe (e.g., the poly-dT anchor probe) comprises a terminal acrydite moiety or other crosslinkable moiety, which can be covalently incorporated into the matrix (e.g., during matrix polymerization). In some embodiments, the poly-dT anchor probe can be about 10 to 20 nucleotides in length (e.g., about 15-nucleotides in length). In some embodiments, the anchor probe can comprise locked-nucleic acid bases to stabilize the hybridization of the poly-dT anchor probe to polyA tails of the RNAs.

According to a further aspect, the target molecules can be amplified products of an analyte, such as amplicons produced within the three dimensional matrix material. The amplicons can then be covalently attached to the matrix, for example, by copolymerization or cross-linking. This results in a structurally stable and chemically stable three dimensional matrix of target molecules. According to this aspect, the three dimensional matrix of target molecules allows for prolonged information storage and read-out cycles. Furthermore, the position of the target molecules in the sample can be stable through one or more migration steps (e.g., active migration) during which spatial probes are migrated into the sample (e.g., electrophoretic migration).

In some aspects, the analytes, polynucleotides and/or amplification product (e.g., amplicon) of an analyte or a probe bound thereto can be anchored to a polymer matrix. For example, the polymer matrix can be a hydrogel. In some embodiments, the polymer matrix comprises functional moieties. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, crosslinking chemistry may be used to anchor functional moieties of the one or more of the polynucleotide probe(s) and/or amplification product (e.g., amplicon) to other molecules and/or to the polymer matrix. For example, any suitable functional moieties can be used, such as an amine, acrydite, alkyne, biotin, azide, and thiol. In some embodiments for crosslinking, the functional moiety may be cross-linked to modified dNTP or dUTP or both. In some cases, a combination of anchoring approaches (e.g., functional moieties) can be used, e.g., to anchor one or more types of molecules to the polymer matrix.

In some embodiments, the anchoring may comprise using an acrylamide group or click chemistry moiety. In some aspects, one or more of the polynucleotide probe(s) and/or amplification product (e.g., amplicon) thereof can comprise modified nucleotides that may have the functional group directly (e.g., acrylamide, click chemistry) or be further modified (e.g., amine modified with an NHS ester chemistry) to contain the functional group. In some embodiments, click reaction chemistry may be used to couple one or more of the target molecules (or a product or derivative thereof), polynucleotide probe(s), and/or amplification product (e.g., amplicon) to the matrix (e.g., hydrogel). Any suitable click reaction and click reactive groups may be used. In some cases, a molecule may be tethered via a click reaction to a click reactive group functionalized hydrogel matrix (e.g., click gel). For example, the 5'azidomethyl-dUTP can be incorporated into a product or derivative of the target molecule, polynucleotide probe(s), and/or amplification product (e.g., amplicon) and then immobilized to the hydrogel matrix functionalized with alkyne groups. In some embodiments, a buffer can be used for click reaction catalyzation, e.g., a Cu(I)-catalyzed alkyne-azide cycloaddition (abbreviated as CuAAC) click reaction catalyzing buffer, which catalyzes the alkyne-azide bond in the click reaction.

In some embodiments, a product or derivative of the target molecule, polynucleotide probe(s), and/or amplification product (e.g., amplicon) may be functionalized by adding nucleotide triphosphate analogs comprising functional moieties for immobilization. In some examples, the nucleotide triphosphate analogs include, but are not limited to, amino-allyl dUTP, 5-TCO-PEG4-dUTP, C8-Alkyne-dUTP, 5-Azidomethyl-dUTP, 5-Vinyl-dUTP, 5-Ethynyl dUTP, and other nucleotide triphosphate analogs comprising a functional moiety for immobilization by cross-linking, or forming a chemical bond between the molecule and the matrix.

In some embodiments, the matrix comprises a cellular or synthetic matrix that contains chemical moieties (e.g., reactive groups) that can react with the functional moieties in the product or derivative of the target molecule, polynucleotide probe(s), and/or amplification product (e.g., amplicon) through functionalization reactions. For example, amino-allyl dUTP may be cross-linked to endogenous free amine groups present in proteins and other biomolecules present within the endogenous or exogenous cellular matrix, or present in a modified synthetic hydrogel matrix, such as an amine-functionalized polyacrylamide hydrogel formed by copolymerization of polyacrylamide and N-(3-aminopropyl)-methacrylamide. In some cases, nucleoside analogs containing azide functional moieties may be cross-linked to a synthetic hydrogel matrix comprising alkyne functional moieties, such as that formed by copolymerization of acrylamide and propargyl acrylamide.

In some embodiments, the biological sample is immobilized in a hydrogel via cross-linking of the polymer material that forms the hydrogel. Cross-linking can be performed chemically and/or photochemically, or alternatively by any other hydrogel-formation method known in the art. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used.

In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of analytes out of the sample, and/or to facilitate transfer of species (such as probes) into the sample. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods are known in the art. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to opening up DNA in a cell for hybridization by a probe. For example, proteinase K treatment may be used to free up DNA with proteins bound thereto.

B. Analytes

The methods and compositions disclosed herein can be used to detect and analyze a wide variety of different analytes. In some embodiments, any of the target molecules described herein can correspond to an analyte. For instance, a target nucleic acid molecule can be an endogenous nucleic acid analyte (e.g., DNA or RNA), a product of an endogenous nucleic acid analyte, a probe that directly or indirectly binds to an endogenous nucleic acid analyte, or a product of a probe that directly or indirectly binds to an endogenous nucleic acid analyte. In some aspects, an analyte can include any biological substance, structure, moiety, or component to be analyzed. In some aspects, a target disclosed herein may similarly include any analyte of interest. In some examples, a target or analyte can be directly or indirectly detected.

Analytes can be derived from a specific type of cell and/or a specific subcellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template (e.g. a padlock or other circularizable probe). Alternatively, the specific binding partner may be coupled to a nucleic acid, which may be detected using an RCA strategy, e.g. in an assay which uses or generates a circular nucleic acid molecule which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

(i) Endogenous Analytes

In some embodiments, a target molecule herein corresponds to an analyte that is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte comprises a target sequence. In some embodiments, the target sequence may be endogenous to the sample, generated in the sample, added to the sample, or associated with an analyte in the sample. In some embodiments, the target sequence is a single-stranded target sequence. In some embodiments, the analytes comprises one or more single-stranded target sequences. In one aspect, a first single-stranded target sequence is not identical to a second single-stranded target sequence. In another aspect, a first single-stranded target sequence is identical to one or more second single-stranded target sequence. In some embodiments, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

(ii) Labelling Agents

In some embodiments, provided herein are methods and compositions for analyzing endogenous analytes (e.g., RNA, ssDNA, and cell surface or intracellular proteins and/or metabolites) in a sample using one or more labelling agents. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labelling agents are the same. In some embodiments in which the plurality of analytes includes a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

(iii) Products of Endogenous Analyte and/or Labelling Agent

In some embodiments, a target molecule herein is a product of an endogenous analyte and/or a labelling agent in a biological sample. In some embodiments, provided herein are methods and compositions for analyzing one or more products of an endogenous analyte and/or a labelling agent in a biological sample. In some embodiments, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product) or derivative thereof is analyzed. In some embodiments, a labelling agent (or a reporter oligonucleotide attached thereto) that directly or indirectly binds to an analyte in the biological sample is analyzed. In some embodiments, a product (e.g., a hybridization product, a ligation product, an extension product (e.g., by a DNA or RNA polymerase), a replication product, a transcription/reverse transcription product, and/or an amplification product) or derivative of a labelling agent that directly or indirectly binds to an analyte in the biological sample is analyzed.

a. Hybridization

In some embodiments, a product of an endogenous analyte and/or a labelling agent is a hybridization product comprising the pairing of substantially complementary or complementary nucleic acid sequences within two different molecules, one of which is the endogenous analyte or the labelling agent (e.g., reporter oligonucleotide attached thereto). The other molecule can be another endogenous molecule or another labelling agent such as a probe. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

Various intermediate probes and intermediate probe sets can be hybridized to an endogenous analyte and/or a labelling agent (e.g., a reporter oligonucleotide attached thereto) and each probe may comprise one or more barcode sequences. In some embodiments, intermediate probes comprise one or more sequences complementary to a targeting domain of a spatial probe disclosed herein. Exemplary barcoded probes or probe sets may be based on a padlock probe, a gapped padlock probe, a SNAIL (Splint Nucleotide Assisted Intramolecular Ligation) probe set, a PLAYR (Proximity Ligation Assay for RNA) probe set, a PLISH (Proximity Ligation in situ Hybridization) probe set, RNA-templated ligation probes, L-shaped probes (e.g., a probe comprising a target-hybridizing sequence and a 5' or 3' overhang upon hybridization to its target sequence), or U-shaped probes (e.g., a probe comprising a target-hybridizing sequence and a 5' overhang and a 3' overhang upon hybridization to its target sequence). The specific probe or probe set design can vary.

b. Ligation

In some embodiments, a product of an endogenous analyte and/or a labelling agent is a ligation product that can be detected by any of the probes provided herein. In some embodiments, the ligation product is formed between two or more endogenous analytes. In some embodiments, the ligation product is formed between an endogenous analyte and a labelling agent. In some embodiments, the ligation product is formed between two or more labelling agent. In some embodiments, the ligation product is an intramolecular ligation of an endogenous analyte. In some embodiments, the ligation product is an intramolecular ligation of a labelling agent, for example, the circularization of a circularizable probe or probe set upon hybridization to a target sequence. The target sequence can be comprised in an endogenous analyte (e.g., nucleic acid such as genomic DNA or mRNA) or a product thereof (e.g., cDNA from a cellular mRNA transcript), or in a labelling agent (e.g., the reporter oligonucleotide) or a product thereof.

In some embodiments, provided herein is a probe or probe set capable of DNA-templated ligation, such as from a cDNA molecule. See, e.g., U.S. Pat. No. 8,551,710, which is hereby incorporated by reference in its entirety. In some embodiments, provided herein is a probe or probe set capable of RNA-templated ligation. See, e.g., U.S. Pat. Pub. 2020/0224244 which is hereby incorporated by reference in its entirety. In some embodiments, the probe set is a SNAIL probe set. See, e.g., U.S. Pat. Pub. 20190055594, which is hereby incorporated by reference in its entirety.

In some embodiments, the ligation herein is a proximity ligation of ligating two (or more) nucleic acid sequences that are in proximity with each other, e.g., through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

c. Primer Extension and Amplification

In some embodiments, a product is a primer extension product of an analyte, a labelling agent, a probe or probe set bound to the analyte, or a probe or probe set bound to the labelling agent.

A primer is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A 'primer' may, in some cases, refer to a primer binding sequence. A primer extension reaction generally refers to any method where two nucleic acid sequences become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

In some embodiments, a product of an endogenous analyte and/or a labelling agent is an amplification product of one or more polynucleotides, for instance, a circular probe or circularizable probe or probe set. In some embodiments, the amplifying is achieved by performing rolling circle amplification (RCA). In other embodiments, a primer that hybridizes to the circular probe or circularized probe is added and used as such for amplification. In some embodiments, the RCA comprises a linear RCA, a branched RCA, a dendritic RCA, or any combination thereof.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (i.e., amplicon) containing multiple copies of the cDNA. Techniques for rolling circle amplification (RCA) are known in the art such as linear RCA, a branched RCA, a dendritic RCA, or any combination thereof (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29:e1 18, 2001; Dean et al. Genome Res. 11:1095-1099, 2001; Schweitzer et al, Nature Biotech. 20:359-365, 2002; U.S. Pat. Nos. 6,054, 274, 6,291,187, 6,323,009, 6,344,329 and 6,368,801). Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix. Exemplary modification and polymer matrix that can be employed in accordance with the provided embodiments comprise those described in, for example, US 2016/0024555, US 2018/0251833, US 2016/0024555, US 2018/0251833 and US 2017/0219465. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

In some embodiments, the RCA template may comprise the target analyte, or a part thereof, where the target analyte is a nucleic acid, or it may be provided or generated as a proxy, or a marker, for the analyte. As noted above, many assays are known for the detection of numerous different analytes, which use a RCA-based detection system, e.g., where the signal is provided by generating a RCP from a circular RCA template which is provided or generated in the assay, and the RCP is detected to detect the analyte. The RCP may thus be regarded as a reporter which is detected to detect the target analyte. However, the RCA template may also be regarded as a reporter for the target analyte; the RCP is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (i.e. a reagent in a detection assay), which is used as a reporter for the assay, or a part of a reporter, or signal-generation system. The RCA template used to generate the RCP may thus be a circular (e.g. circularized) reporter nucleic acid molecule, namely from any RCA-based detection assay which uses or generates a circular nucleic acid molecule as a reporter for the assay. Since the RCA template generates the RCP reporter, it may be viewed as part of the reporter system for the assay.

In some embodiments, a product herein includes a molecule or a complex generated in a series of reactions, e.g., hybridization, ligation, extension, replication, transcription/reverse transcription, and/or amplification (e.g., rolling circle amplification), in any suitable combination. For example, a product comprising a target sequence for a probe disclosed herein (e.g., a spatial probe comprising a targeting domain and a migration domain) may be a hybridization complex formed of a cellular nucleic acid in a sample and an exogenously added nucleic acid probe. The exogenously added nucleic acid probe may be optionally ligated to a cellular nucleic acid molecule or another exogenous nucleic acid molecule. In other examples, a product comprising a target sequence for a probe disclosed herein (e.g., a spatial probe comprising a targeting domain and a migration domain) may be an RCP of a circularizable probe or probe set which hybridizes to a cellular nucleic acid molecule (e.g., genomic DNA or mRNA) or product thereof (e.g., a transcript such as cDNA, a DNA-templated ligation product of two probes, or an RNA-templated ligation product of two probes). In other examples, a product comprising a target sequence for a probe disclosed herein (e.g., a spatial probe comprising a targeting domain and a migration domain) may be a probe hybridizing to an RCP. The probe may comprise an overhang that does not hybridize to the RCP but hybridizes to another probe (e.g., a probe comprising a second overhang for attachment of one or more modified nucleotides).

C. Target Sequences and Barcodes

A target sequence for a probe disclosed herein (e.g., a spatial probe comprising a targeting domain and a migration domain) may be comprised in any analyte disclose herein, including an endogenous analyte (e.g., a viral or cellular nucleic acid), a labelling agent (e.g., a reporter oligonucleotide attached thereto), or a product of an endogenous analyte and/or a labelling agent.

In some aspects, one or more of the target sequences includes one or more barcode(s), e.g., at least two, three, four, five, six, seven, eight, nine, ten, or more barcodes. In some embodiments, one or more of the target molecules or intermediate probes comprises a barcode sequence adjacent to the target sequence hybridized by a targeting domain of a spatial probe. In some embodiments, extension of the spatial probe using a polymerase using the barcode as a template enables incorporation of a sequence complementary to the barcode into a product of the spatial probe. Barcodes can spatially-resolve molecular components found in biological samples, for example, within a cell or a tissue sample. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In any of the preceding embodiments, barcodes (e.g., primary and/or secondary barcode sequences) can be analyzed (e.g., detected or sequenced) using any suitable methods or techniques, including those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), in situ sequencing, hybridization-based in situ sequencing (HybISS), targeted in situ sequencing, fluorescent in situ sequencing (FISSEQ), sequencing by synthesis (SBS), sequencing by ligation (SBL), sequencing by hybridization (SBH), or spatially-resolved transcript amplicon readout mapping (STARmap). In any of the preceding embodiments, the methods provided herein can include analyzing the barcodes by sequential hybridization and detection with a plurality of labelled probes (e.g., detection oligos).

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. In some embodiments, the barcode sequences corresponding to the target molecules are detected, rather than endogenous sequences, which can be an efficient readout in terms of information per cycle of sequencing. Because the barcode sequences are pre-determined, they can also be designed to feature error detection and correction mechanisms, see, e.g., U.S. Pat. Pub. 20190055594 and WO2019199579A1, which are hereby incorporated by reference in their entirety.

In some embodiments, a common target sequence can be used for analysis of one or more target molecules. In some embodiments, the targeting domains of first-dimension spatial probes for two or more different target molecules can share a common sequence, optionally wherein the target domains of first-dimension spatial probes for two or more different target molecules are identical. The common sequence in the targeting domains of first-dimension spatial probes may hybridize to a common adapter sequence (e.g., in a 3' or 5' overhang) shared by intermediate probes that recognize different target molecules.

In some embodiments, a common target sequence can be a polyA tail (e.g., of an mRNA molecule). In some embodiments, the common sequence of first-dimension spatial probes for two or more different target molecules can comprise an oligo(dT) sequence (e.g., about 10,11, 12, 13, 14, 15, 16, 17, 18, 19, or 20 nucleotides in length). In some embodiments, the targeting domain is an oligo(dT) sequence. In some embodiments, the spatial probe can be extended using the mRNA as a template to form an extension product, thereby incorporating sequence information corresponding to an individual mRNA into the extension product of the spatial probe.

III. PROBES FOR THREE-DIMENSIONAL ANALYSIS

Disclosed here are methods for dispersing, migrating or separating oligonucleotides (e.g., spatial probes) throughout a three-dimensional space. In some examples, the three-dimensional space is a medium. The medium may be a polymer substance. In some examples the medium may be capable of conducting electricity. In some examples, the medium contains tissues, cells and/or RNAs. In some examples, the oligonucleotides dispersed throughout the three-dimensional space are of different lengths or sizes, are separated through the three-dimensional space based on their different sizes, and/or are migrated through the three-dimensional space using electrophoresis. As described in more detail later in the application, these methods can be used to determine locations of cells and/or target molecules (e.g., target nucleic acid molecules such as RNAs) in a three-dimensional space.

In some aspects of the methods disclosed herein, methods for facilitating migration can be passive (e.g., diffusion) and/or active (e.g., electrophoretic migration of nucleic acids). Non-limiting examples of passive migration can include simple diffusion and osmotic pressure created by the rehydration of dehydrated objects.

Passive migration by diffusion uses concentration gradients. Diffusion is movement of untethered objects toward equilibrium. Therefore, when there is a region of high object concentration and a region of low object concentration, the object (e.g., probe, the analyte, etc.) moves to an area of lower concentration. In some embodiments, untethered probes move down a concentration gradient. In some embodiments, a population of oligonucleotides (e.g., splints or intermediate probes) is migrated into the sample by passive diffusion and then immobilized (e.g., via cross-linking) before another population of probes (e.g., any of the spatial probes described herein) is migrated into the sample by active migration (e.g., electrophoretic migration of nucleic acids).

Migration of a population of nucleic acid molecules of different sizes or lengths through a medium and separation of the molecules according to size, is well known in the art. In some examples, the nucleic acids are migrated through a polymer medium like agarose or polyacrylamide using an electric field. The method is known as a type of electrophoresis.

In FIG. 1A, an example of electrophoresis of nucleic acid molecules of different lengths through a single dimension, here an X-dimension, is shown. In FIG. 1, the square represents a horizontal agarose slab gel. In the example, a population of nucleic acid molecules of different lengths is loaded onto the gel, along the entire y-dimension of the gel (i.e., the height of the gel in FIG. 1A), and electrophoresed in the X-dimension. Each vertical line in the square represents a subset of nucleic molecules of the same length that was contained in the population originally loaded onto the gel and separated by size during the electrophoresis. The left-most line (designated "L" for large), represents the subset of nucleic molecules within the total population that were of the largest or longest relative size. These molecules migrated the shortest distance through the agarose gel when the electric field was applied. The right-most line (designated "S" for small), represents the subset of nucleic acid molecules within the total population that are of the smallest or shortest relative size. These molecules migrated through the agarose gel the largest distance.

In FIG. 1A, the nucleic acid molecules in the original population were of 7 discrete lengths. Each vertical line in the square represents a subset of the original population of molecules having one of the 7 lengths. Had the original population contained more than 7 subsets—100 subsets for example—there may have been 100 vertical lines in the same physical space where currently there are 7. As the number of subsets increases, separation between the individual subpopulations would decrease in the same physical space. At some point, there would be too many subsets for the gel system to provide distinct separation between the subsets. Instead, there would be dispersal of oligonucleotides throughout the entirety of the x-dimension of the gel slab. That is, there would not be areas of the gel that did not contain oligonucleotides.

In some embodiments, the properties of the migration domain influences separation of the spatial probes through the sample, for example, the length differences between oligonucleotides in the separate subsets influences separation in this system. For example, if the oligonucleotides of each adjacent subset of the 7 subpopulations shown in FIG. 1A differed in length by at least 10%, then adding subsets that differ in length by only 5%, 2%, 1%, or less than 1% would decrease separation between different subsets until, at some point, there would not be distinct separation. Again, there would be dispersal of oligonucleotides throughout the entirety of the X-dimension of the gel. Separation of subsets of oligonucleotides of different lengths in this system may also depend on the concentration of the medium, the buffer used for the electrophoresis, and other factors. Therefore, this system can be manipulated to disperse oligonucleotides throughout the entire x-dimension of the gel slab with little or no areas of the slab that do not contain oligonucleotide molecules.

Figure 1B:
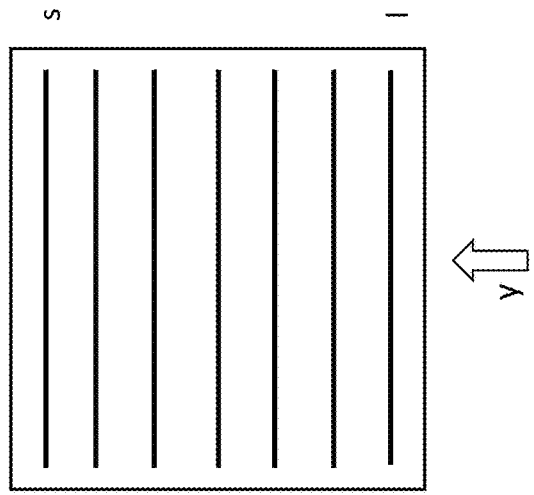
FIG. 1B illustrates exemplary oligonucleotides of different lengths that have been migrated through a medium in a y-dimension and have been separated based on size.

FIG. 1B illustrates a similar electrophoresis experiment, except that the population of nucleic acid molecules of different lengths was loaded onto the gel along the entirety of the x-dimension (i.e., the width of the gel) and electrophoresed in the y-dimension. In this illustration, the line at the bottom of the square, designated "1" for large, represents the subset of molecules within the total population that are of the largest or longest relative size and migrated the shortest distance through the gel in the y-dimension. The line at the top of the square, designated "s" for small, represents the subpopulation of molecules within the total population that were of the smallest or shortest relative size and migrated the shortest distance through the gel.

Figure 1C:
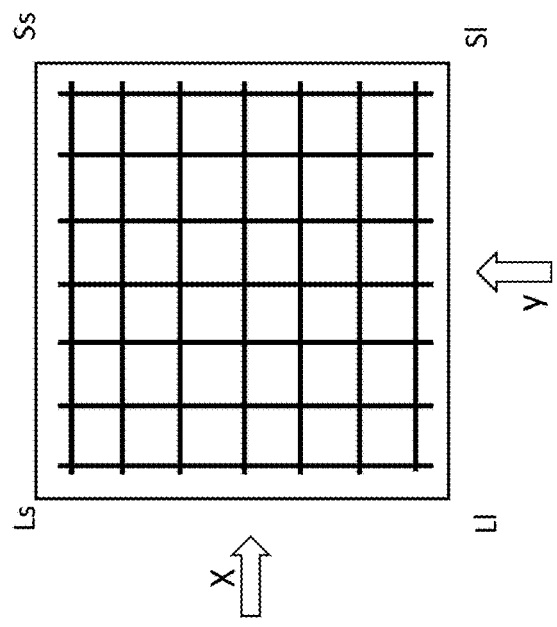
FIG. 1C illustrates an exemplary first population of oligonucleotides of different lengths that have been migrated through a medium in an X-dimension, separated based on size and immobilized in the medium, and an exemplary second population of oligonucleotides of different lengths that have been migrated through the medium in a y-dimension, separated based on size and immobilized in the medium.

FIG. 1C illustrates a combination of electrophoresis of the population of nucleic acids in an x-dimension and in a y-dimension. In this experiment, the population of nucleic acid molecules of different lengths was first electrophoresed in the X-dimension, as was shown in FIG. 1A. At the conclusion of electrophoresis in the X-dimension, the separated subsets of molecules are fixed or immobilized in the gel so that further application of an electric field does not result in these molecules, which have already been separated based on size in the X-dimension, migrating any further. Then, the same gel was used to separate a distinct population of oligonucleotides of different lengths in the y-dimension.

Immobilization of oligonucleotides in the medium through which they have migrated can be accomplished in various ways. Functionally, immobilization involves making the oligonucleotides unable to migrate further, for example when an electric field is applied during electrophoresis. In some examples, the oligonucleotides in the medium may be anchored to substances that do not migrate during electrophoresis. Oligonucleotides may be chemically and/or enzymatically linked or crosslinked to the medium, components of the medium or to substances added to the medium. The medium may contain chemical groups that can be activated, for example, which results in linking the oligonucleotides to these groups in the medium. Oligonucleotides may contain functional groups that can be activated, resulting in linking oligonucleotides to the medium, to each other, or to substances in the medium. Oligonucleotides may be chemically and/or enzymatically linked or crosslinked to other oligonucleotides or other nucleotide sequences. Oligonucleotides may be ligated to other oligonucleotides or other nucleotide sequences. The oligonucleotides may be anchored to substances that do not migrate during electrophoresis (e.g., components of the medium) and/or to other like or dissimilar molecules in the vicinity of the oligonucleotides to create larger molecules that do not readily move through the medium when an electric field is applied. In some examples, the oligonucleotides may be linked or crosslinked to the medium, to each other, or to other nucleic acid molecules in the medium that are in the vicinity of the oligonucleotides (e.g., RNAs, RNA capturing probes, amplification/ligation products derived from the RNA or RNA capturing probes, and the like; these are discussed later in the application).

One example of the result of this two-dimensional electrophoresis experiment is illustrated in FIG. 1C. After completion of both dimensions of electrophoresis, locations of oligonucleotides within the two-dimensional space can be defined by X- and y-dimension coordinates. For example, oligonucleotides in the upper left corner of the agarose slab can be defined by "Ls" which represents the longest subset of oligonucleotides in the population that was electrophoresed in the X-dimension, and the shortest subset of oligonucleotides in the population that was electrophoresed in the y-dimension. The oligonucleotides in the lower right corner of the agarose slab can be defined by "Sl" which represents the shortest subset of oligonucleotides in the population that was electrophoresed in the X-dimension, and the longest subset of oligonucleotides in the population that was electrophoresed in the y-dimension. Similarly, the oligonucleotides in the upper right corner can be defined by "Ss" and the oligonucleotides in the lower left corner can be defined by "Ll." As described above, by adding more subsets and/or by decreasing the magnitude of the oligonucleotide length differences between subsets, in both the populations of oligonucleotides electrophoresed in the X-dimension and in the y-dimension, it is possible to disperse and populate all locations of the two-dimensional space with oligonucleotides. That is, there would not be a location within the two-dimensional space that did not contain both an oligonucleotide that was electrophoresed in the X-dimension and an oligonucleotide that was electrophoresed in the y-dimension.

Figure 2:
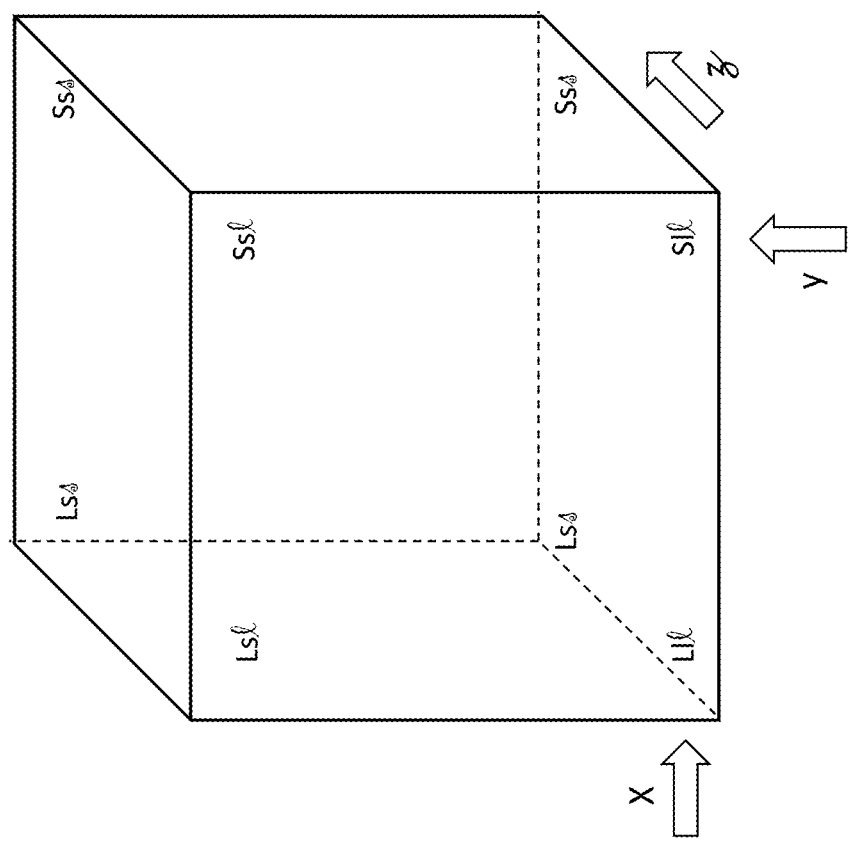
FIG. 2 illustrates an exemplary volume in which a first population of oligonucleotides of different lengths that have been migrated through a medium in an X-dimension, separated based on size and immobilized in the medium; an exemplary second population of oligonucleotides of different lengths that have been migrated through the medium in a y-dimension, separated based on size and immobilized in the medium; and an exemplary third population of oligonucleotides of different lengths that have been migrated through the medium in a $\mathcal{Z}$-dimension, separated based on size and immobilized in the medium. The oligonucleotide molecules and the "bands" in which they migrate are not shown.

FIG. 2 extends the experiment to three-dimensional space. In this experiment, a population of oligonucleotides was first electrophoresed in the X-dimension of the space. After electrophoresis in the x-dimension, the separated oligonucleotides are immobilized in the three-dimensional gel so that they will not migrate when additional electric fields are applied. Next, a population of oligonucleotides was similarly electrophoresed in the y-dimension of the space and immobilized. Then, a population of oligonucleotides was similarly electrophoresed in the $z$-dimension of the space.

Note that, because this space is three dimensional, a sample to be electrophoresed may be applied to the entire surface of the gel that is perpendicular to the dimension of electrophoresis. For example, to electrophorese in the X-dimension, the sample containing the oligonucleotides to be separated is applied to the entire area of a y-$z$ plane at the left-most edge of the cube shown in FIG. 2. Electrophoresis in the y- and $z$-dimensions is performed similarly. Example devices that provide for such sample application are described later in this application. In some embodiments, the migrating or separating of the oligonucleotides (e.g., probes) in each dimension may be performed separately and/or sequentially (e.g., in one direction followed by another).

Location of oligonucleotides within three-dimensions of the space can be defined by X-, y- and $z$- -coordinates. FIG. 2 defines locations of subsets oligonucleotides located in the 8 corners of illustrated cube. For example, the location of oligonucleotides in the front, upper left corner of the cube can be defined by "Lsl" which represents the longest subset of oligonucleotides electrophoresed in the x-dimension, the shortest subset of oligonucleotides electrophoresed in the y-dimension and the longest subset of oligonucleotides electrophoresed in the z-dimension. The other 7 corners of the cube can be defined similarly. As in the discussion of the experiment illustrated in FIG. 1C, the three-dimensional system of FIG. 2 can be manipulated to populate the entire space with oligonucleotides (e.g., by adding oligonucleotide subsets, decreasing length differences between subsets, changing medium concentration and/or electrophoresis buffer, and the like).

Figure 3A:
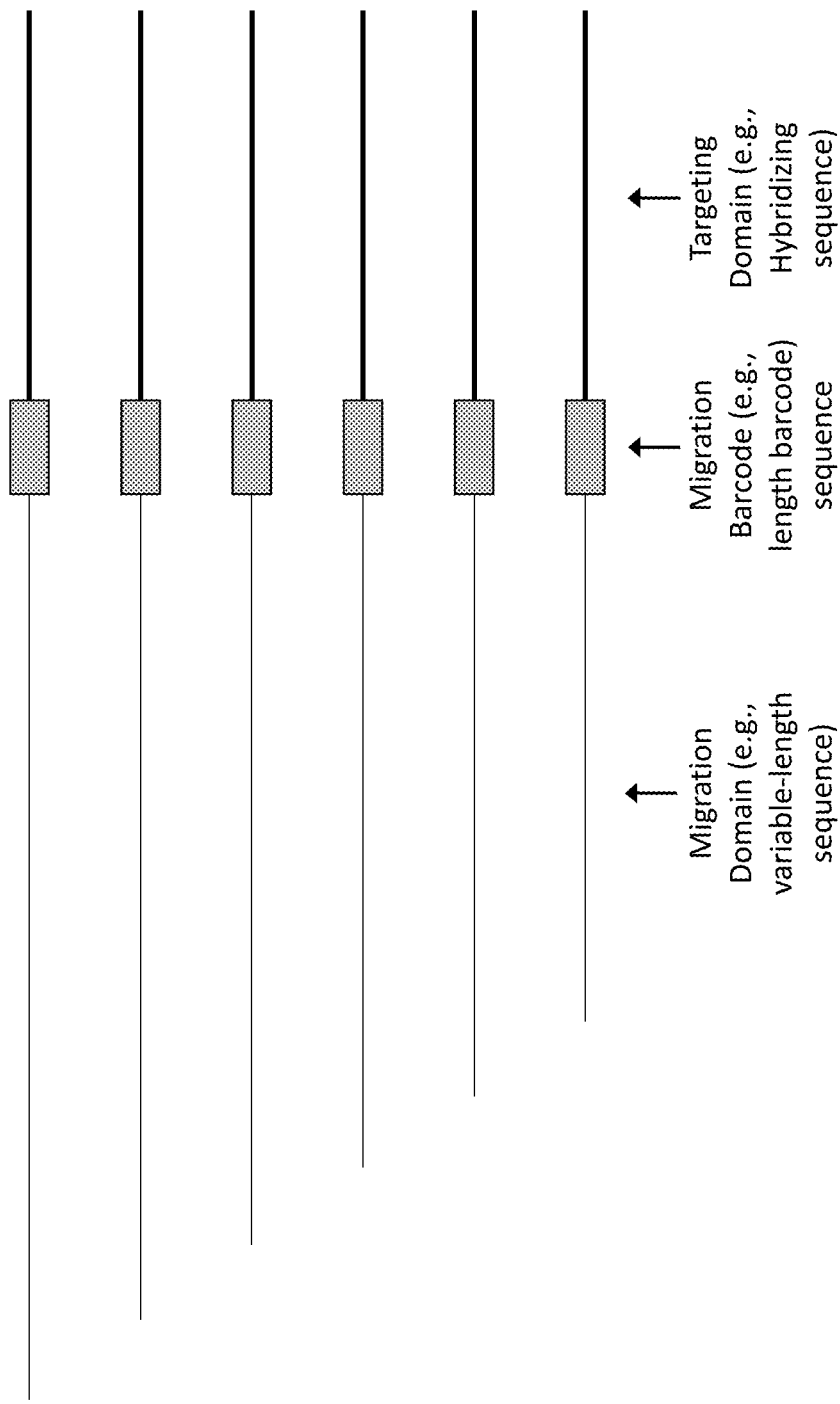
FIG. 3A illustrates an exemplary population of oligonucleotides of different lengths, containing migration domains (e.g., variable-length sequences), migration barcode (e.g., length barcode) sequences, and targeting domains (e.g., hybridizing sequences). Optionally, an oligonucleotide can comprise one or more other barcode sequences, such as a hybridizing barcode sequence (not shown) that corresponds to the targeting domain (e.g., hybridizing sequence) of the oligonucleotide. The hybridizing barcode sequence can be located anywhere in the oligonucleotide and can overlap with any one or more of the migration domain, the migration barcode sequence, and the targeting domain.
Figure 4A:
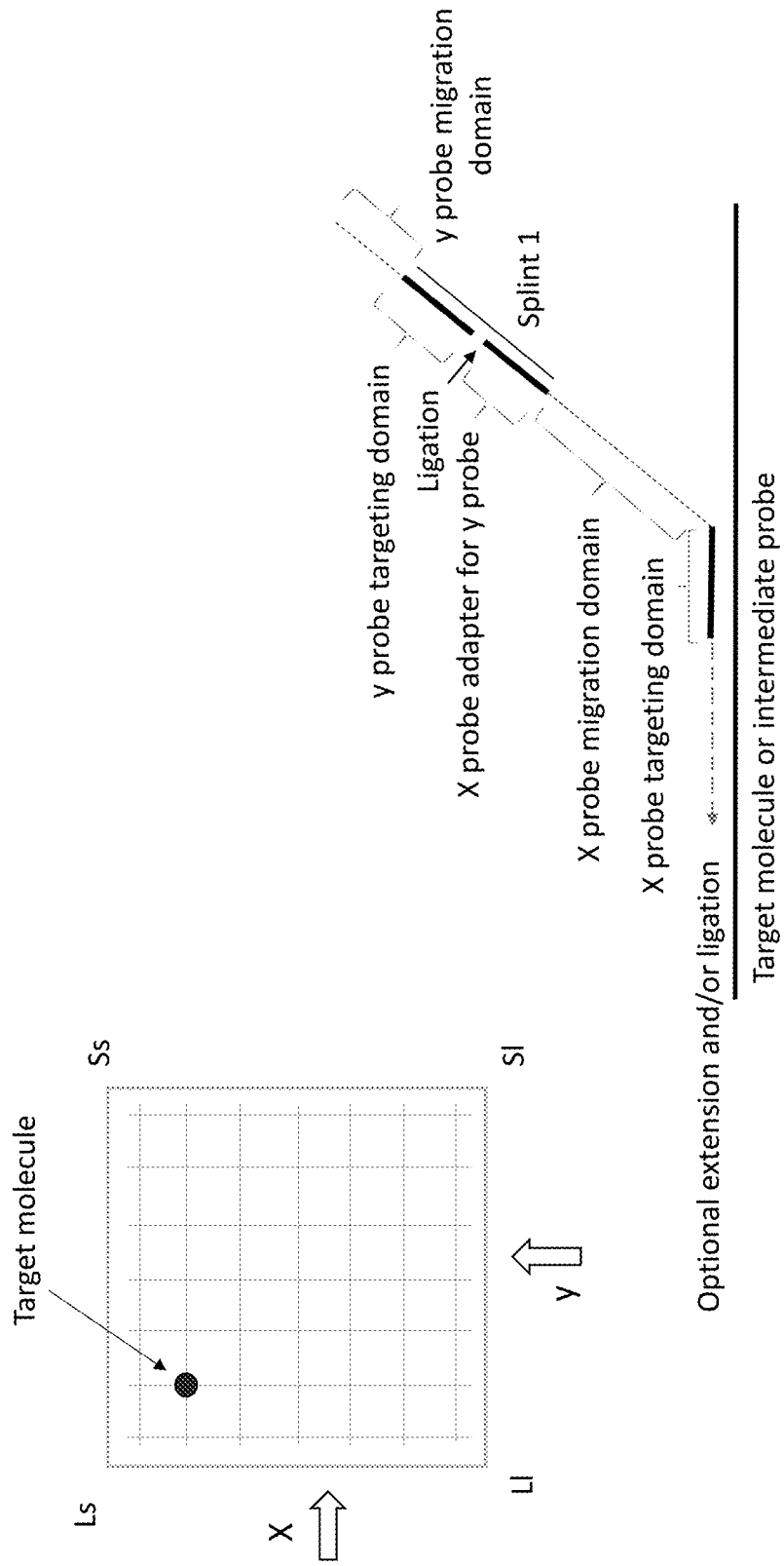
FIGS. 4A-4C show exemplary hybridization complexes formed by X, y, and $\mathcal{Z}$ probes with a target molecule or intermediate probe that is directly or indirectly hybridized to the target molecule. Splints can be used to connect the X, y, and $\mathcal{Z}$ probes (FIGS. 4A-4B). Alternatively, an X probe or y probe can comprise a sequence that serves as a splint for probe hybridization and subsequent ligation (FIG. 4C). For simplicity, the migration barcode sequences are not labeled.
Figure 4B:
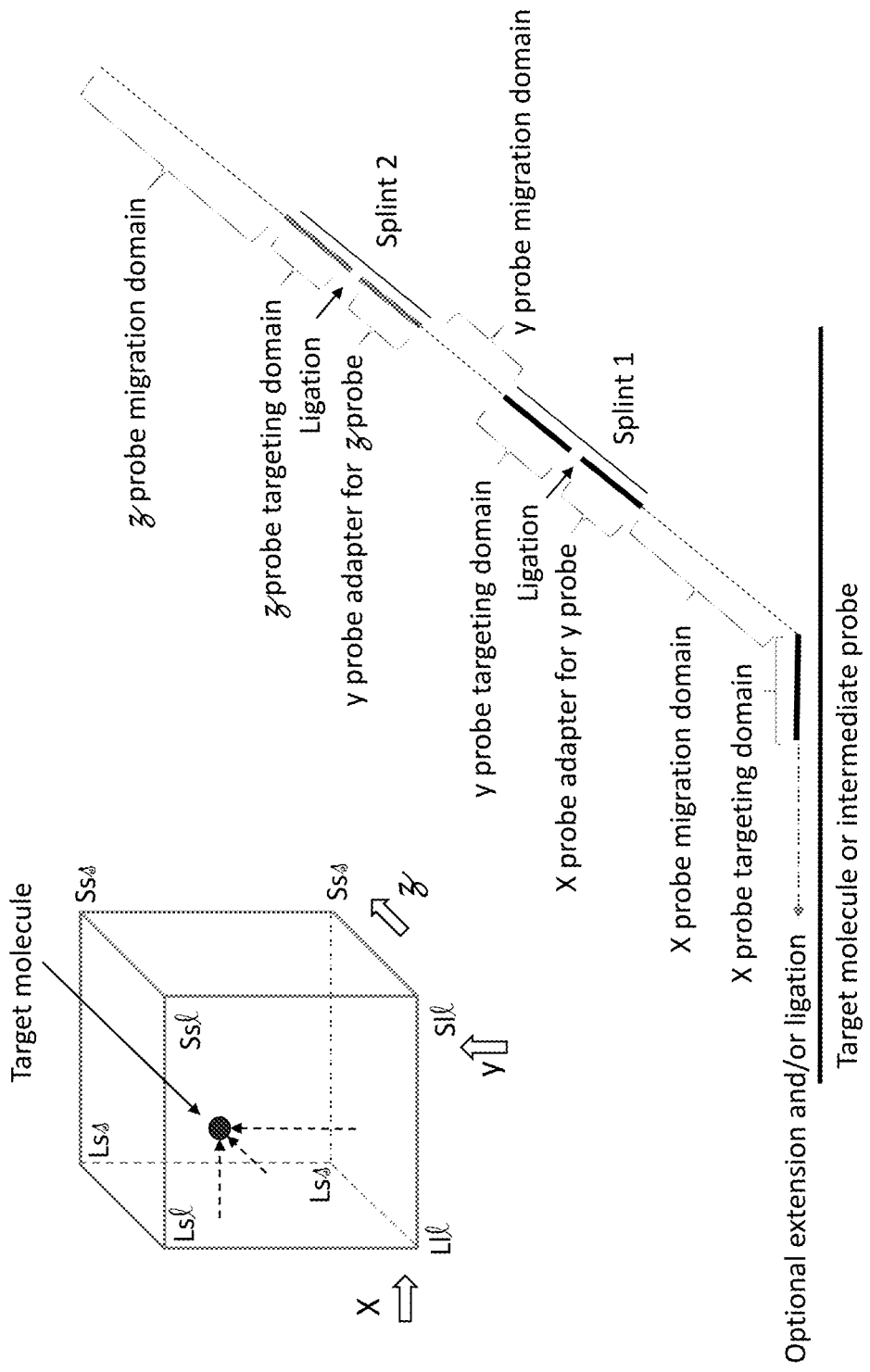
Figure 4C:
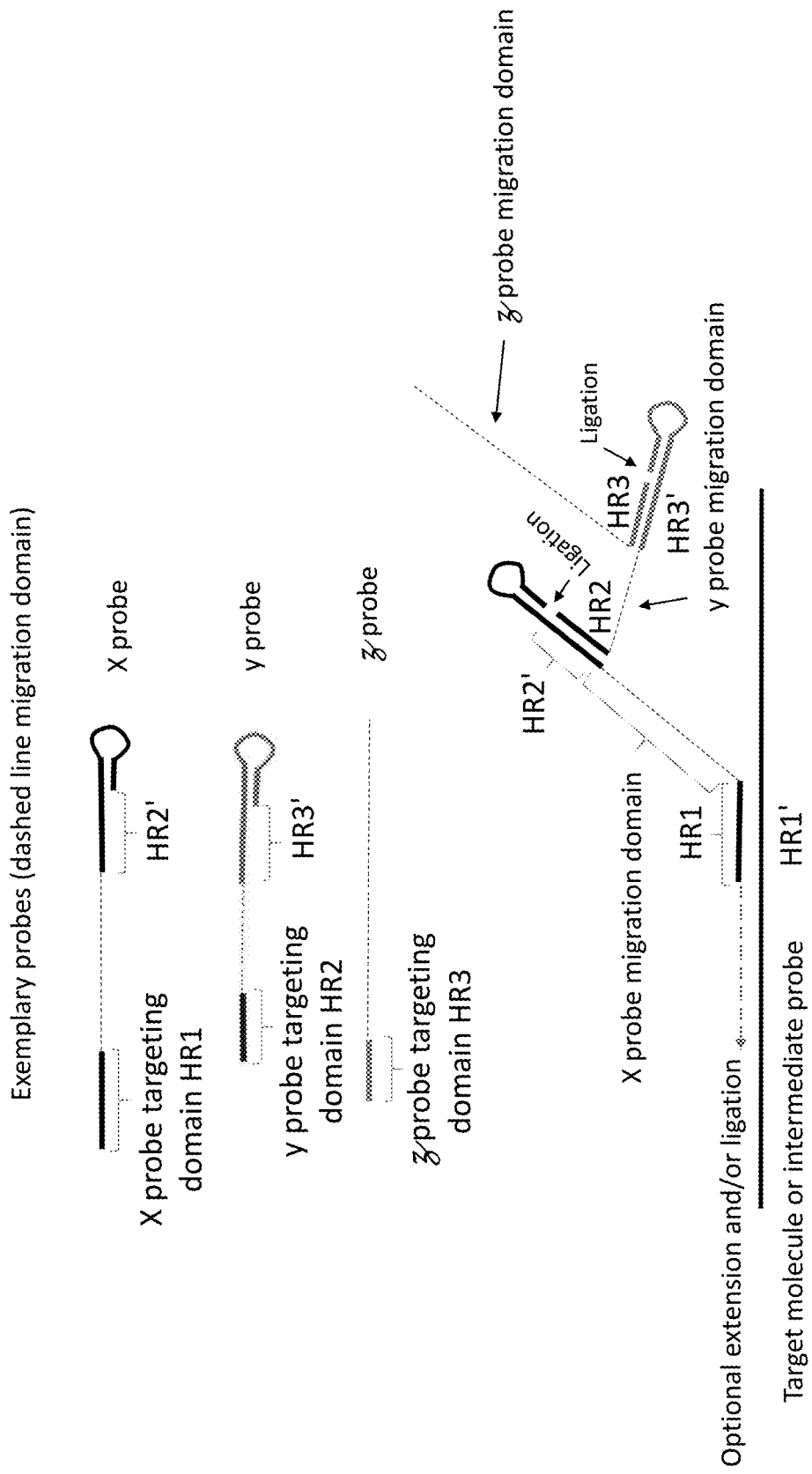

FIGS. 4A-4C show exemplary hybridization complexes between X, y, and/or $z$ probes and a target molecule or intermediate probe. The migration domains (e.g., variable-length sequences) and/or migration barcode (e.g., length barcode) can be used to identify the position of the target molecule in the x- and y-dimensions. The thick lines indicate targeting domains (e.g., hybridizing sequences), and the dashed lines indicate variable length sequences of the X, y, and $z$ probes. The migration barcode (e.g., length barcode) can be positioned in the probes according to any of the configurations illustrated in FIGS. 3A-3C.

FIG. 4A shows an exemplary hybridization complex comprising an X probe hybridized to a target molecule or intermediate probe, a y probe, and a splint, wherein the X probe and y probe can be ligated together using the splint. Optionally, the X probe can be extended using the target molecule or intermediate probe as a template. In some embodiments, the X probe comprises a targeting domain and an adapter sequence, wherein the targeting domain (e.g., hybridizing sequence) of the X probe hybridizes to the target molecule or intermediate probe and the adapter sequence of the X probe hybridizes to a first splint (Splint 1 as shown in FIG. 4B). In some embodiments, all or a portion of the targeting domain (e.g., hybridizing sequence) of the y probe hybridizes to the first splint. In some embodiments, the X, and y probes can be connected by chemical or enzymatic ligation. The sequenced X and y probe complex can provide the identity of the target molecule (e.g., via the sequence of a targeting domain (e.g., hybridizing sequence) complementary to the target molecule, which can optionally be extended using the target molecule as a template) and the localization of the target molecule in two-dimensional space (e.g., via the length of the variable-length sequences of the X and y probes).

FIG. 4B shows an exemplary hybridization complex comprising an X probe hybridized to a target molecule or intermediate probe, a y probe, a $z$ probe, and splints, wherein the X probe, y probe, and $z$ probes can be ligated together using the splints. Optionally, the X probe can be extended using the target molecule or intermediate probe as a template. In some embodiments, the X probe comprises a targeting domain and an adapter sequence, wherein the targeting domain (e.g., hybridizing sequence) of the X probe hybridizes to the target molecule or intermediate probe and the adapter sequence of the X probe hybridizes to a first splint (Splint 1 as shown in FIG. 4B). In some embodiments, y probe comprises a targeting domain and an adapter sequence, wherein the targeting domain (e.g., hybridizing sequence) of the y probe hybridizes to the first splint, and the adapter sequence of the y probe hybridizes to a second splint (Splint 2 as shown in FIG. 4B). In some embodiments, all or a portion of the targeting domain (e.g., hybridizing sequence) of the 3′ probe hybridizes to the second splint. In some embodiments, the X, y, and 3′ probes can be connected by chemical or enzymatic ligation. The sequenced X, y, and 3′ probe complex can provide the identity of the target molecule (e.g., via the sequence of a targeting domain (e.g., hybridizing sequence) complementary to the target molecule, which can optionally be extended using the target nucleic acid as a template), and the localization of the target molecule in three-dimensional space (e.g., via the length of the variable-length sequences of the X, y, and 3′ probes). In some embodiments, the X probe can be a U-shaped probe instead of an L-shaped probe as shown in FIG. 4B. For example, the X probe may comprise a target-hybridizing sequence flanked by sequences of the variable-length sequence (e.g., similar to the second probe shown in FIG. 3C). Thus, upon hybridization to the target molecule, the X probe has a 3' overhang and a 5' overhang, either of which may serve as an adapter for the y probe or the 3′ probe.

In some embodiments, the splint(s) can be an integral part of the X, y, and/or 3′ probes. For example, as shown in FIG. 4C, the X, y, and/or 3′ probes can be designed with a terminal hairpin region, such that a portion of the targeting domain (e.g., hybridizing sequence) or adapter sequence that hybridizes to another probe can be used as a splint to template ligation. In the illustrated embodiment, the targeting domain (e.g., hybridizing sequence) of the X probe (labelled HR1) hybridizes to a region of the target molecule or intermediate probe (labelled HR1') and portion of the adapter sequence of the X probe forms a hairpin loop, wherein part of the adapter sequence (labelled HR2') binds to the first portion of a targeting domain (e.g., hybridizing sequence) of the y probe (labelled HR2). Thus, the X probe provides a template for ligation of the X and y probes. Similarly, a portion of the adapter sequence of the y probe can form a hairpin loop, wherein a portion of the adapter sequence (labelled HR3') binds to a targeting domain (e.g., hybridizing sequence) of the 3′ probe. Thus, the y probe provides a template for ligation of the y and 3′ probes.

In any of the embodiments described herein, the X, y, and/or 3′ probes can hybridize to an adapter (e.g., an intermediate probe) that hybridizes to the target molecule, rather than hybridizing directly to the target molecule. In some embodiments, a plurality of adapters can be used to hybridize to a plurality of target molecules, wherein each adapter (e.g., an intermediate probe) comprises a hybridizing region that specifically hybridizes to a sequence of the target nucleic acid, and one or more landing pads (e.g., adapter sequences) for hybridization of X, y, and/or 3′ probes. In some embodiments, each adapter of the plurality comprises different targeting sequences that hybridize to the target nucleic acid. In some embodiments, each adapter of the plurality comprises the same landing pad sequences (e.g., adapter sequences) for hybridization to X, y, and/or 3′ probes or to splints. In some embodiments, the adapter(s) can be hybridized to target molecules in a sample prior to migration of the X, y, and/or 3′ probes. In some embodiments, the same set of X, y, and 3′ probes can be used to detect a plurality of target molecules, wherein the X, y, and/or 3′ probes hybridize to universal X, y, and/or 3′ probe landing sequences on the adapter. In some embodiments, the adapter can be L-shaped (e.g., with a region that hybridizes to the target molecule at one end and an overhang region at the other end). In some embodiments, the adapter can be U-shaped (e.g., with a central region that hybridizes to the target molecule and two overhang portions). In some embodiments, the intermediate probes are delivered to the biological sample without electrophoresis and allowed to hybridize to the target molecules. In some embodiments, upon specific hybridization to the target molecules, the intermediate probes are anchored to the target molecules and/or other endogenous or exogenous molecules in the locations of the target molecules, such that the anchored intermediate probes do not migrate during electrophoresis of the X, y, and/or 3′ probes.

Figure 5A:
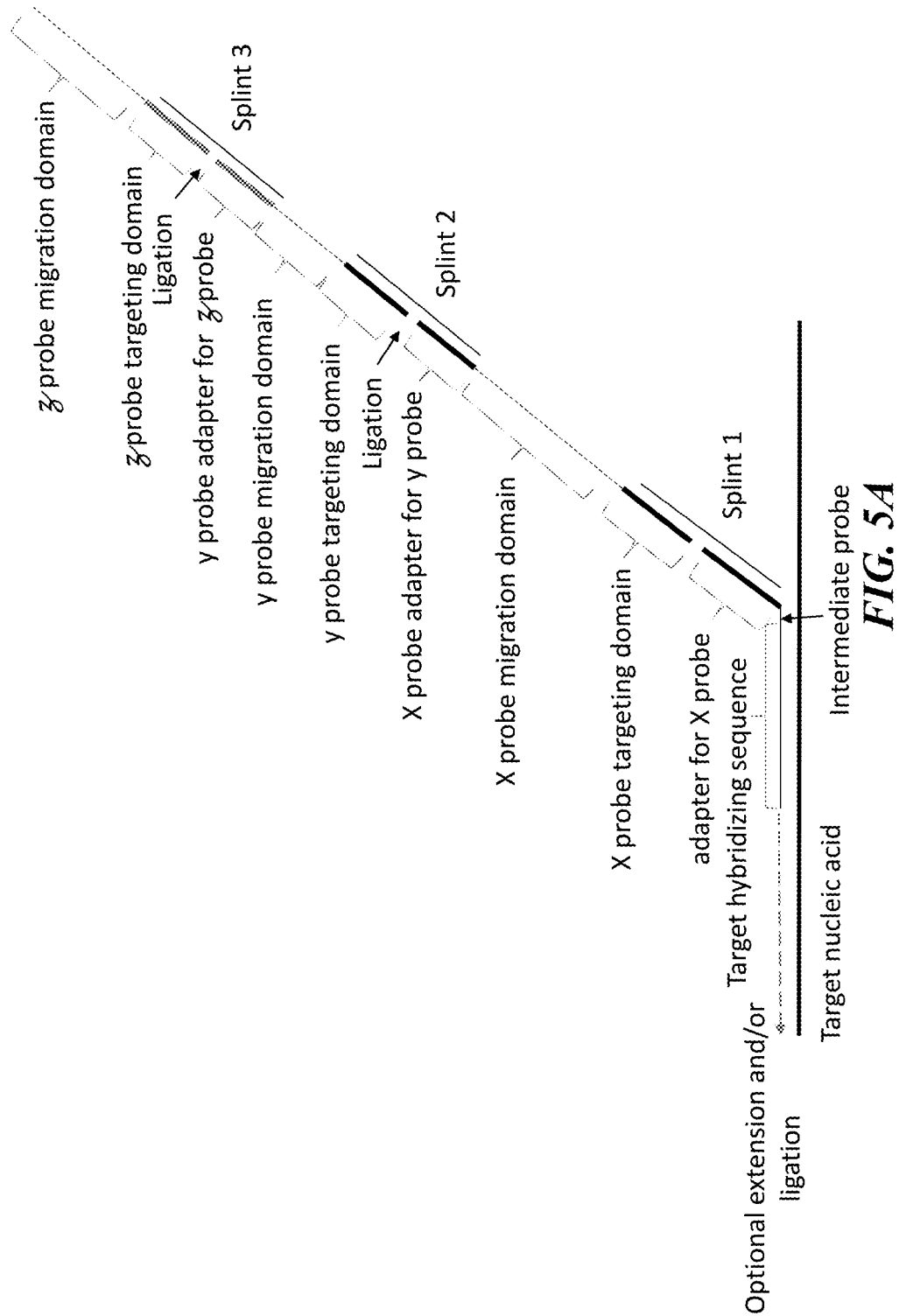
FIGS. 5A-5B show exemplary hybridization complexes formed by X, y, and $\mathcal{Z}$ probes with an L-shaped intermediate probe (FIG. 5A) or a U-shaped intermediate probe (FIG. 5B) hybridized to a target nucleic acid and comprising an adapter for an X probe. Optionally, the intermediate probe can be provided as two probes and ligated together. Splints can be used to connect the X, y, and $\mathcal{Z}$ probes. For simplicity, the migration barcode sequences are not labeled.
Figure 5B:
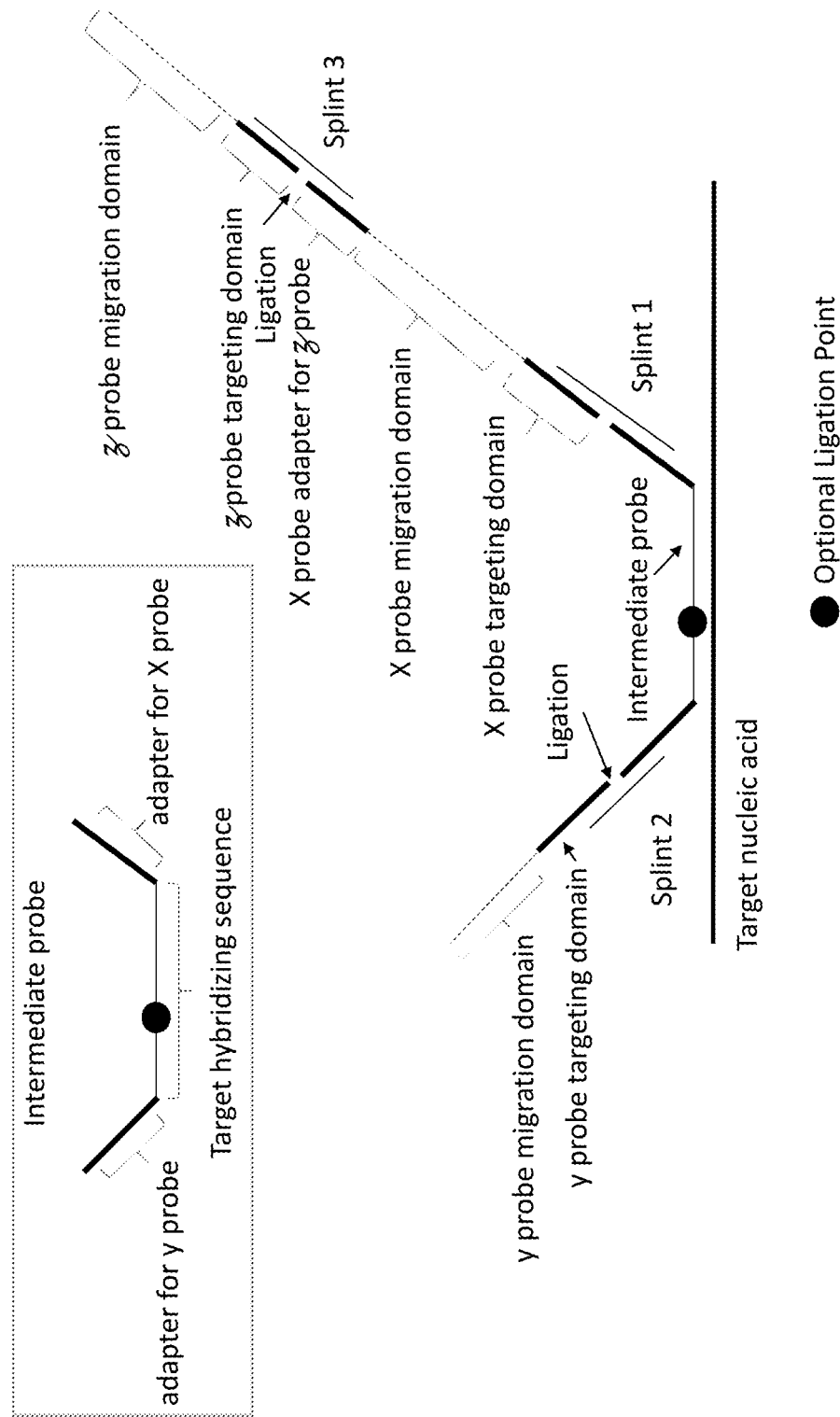

FIGS. 5A-5B show exemplary hybridization complexes formed by X, y, and 3′ probes with an intermediate probe and a target molecule. Optionally, splint oligonucleotides can be used to connect the X, y, and 3′ probes. As shown in FIG. 5A, a first, second, and third splint can be used to ligate together the L-shaped intermediate probe and the X, y, and 3′ probes. As shown in FIG. 5B, a first, second, and third splint can be used to ligate together the U-shaped intermediate probe and the X, y, and 3′ probes. Alternatively, portions of the intermediate probe and the X, y, and/or 3′ probes can be used to ligate together the intermediate probe and the X, y, and/or 3′ probes, in a variation of the splint configuration illustrated in FIG. 4C. In some embodiments, the intermediate probe may be a ligation product of two probes that are ligated together upon specific hybridization to adjacent sequences in the target molecule. In further embodiments, the overhang region of the intermediate probe may comprise landing pad sequences for multiple probes (e.g., for an X probe, a y probe, and a 3′ probe), and the intermediate probe can be used as a splint for ligation of the X probe, the y probe, and the 3′ probe. In some embodiments, the overhang region may comprise a barcode sequence that is used as a template for a primer extension reaction to extend the end of one of the X, y, or 3′ probes hybridized thereto, thereby incorporating a sequence complementary to the barcode into the extended probe. Any of the variations in probe hybridization complexes described herein may be between probes and an intermediate probe rather than between probes and a target nucleic acid molecule.

Figure 6A:
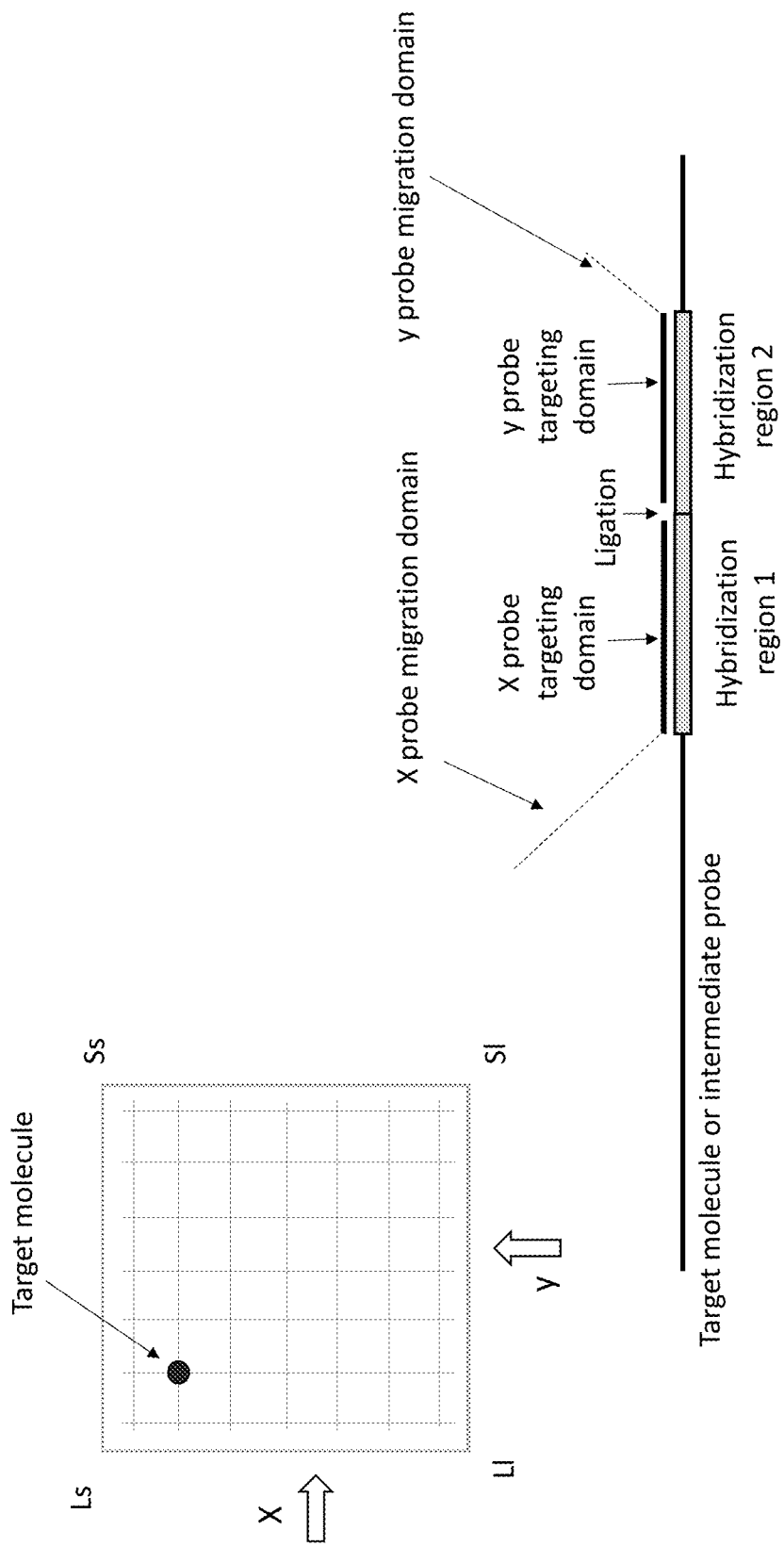
FIGS. 6A-6D show exemplary hybridization complexes formed by X, y, and $\mathcal{Z}$ probes with a target molecule or intermediate probe. Optionally, the target molecule, one of the X, y or $\mathcal{Z}$ probes, or an intermediate probe can be used as a splint to connect the X, y, and $\mathcal{Z}$ probes.

In some embodiments, the target nucleic acid (or an intermediate probe) can serve as a splint for ligation of X, y, and/or 3′ probes. FIG. 6A shows an exemplary hybridization complex wherein an X probe and a y probe hybridize to adjacent hybridization regions of a target nucleic acid, and the target nucleic acid serves as a template for ligation of the X and y probes. In some embodiments, only X and y probes that are hybridized to the target nucleic acid will be ligated. The sequenced X, and y probe complex can provide the identity of the target nucleic acid (e.g., via the sequence of a targeting domain (e.g., hybridizing sequence) complementary to the target nucleic acid) and the localization of the target nucleic acid in three-dimensional space (e.g., via the length of the variable-length sequences of the X and y probes).

Figure 6B:
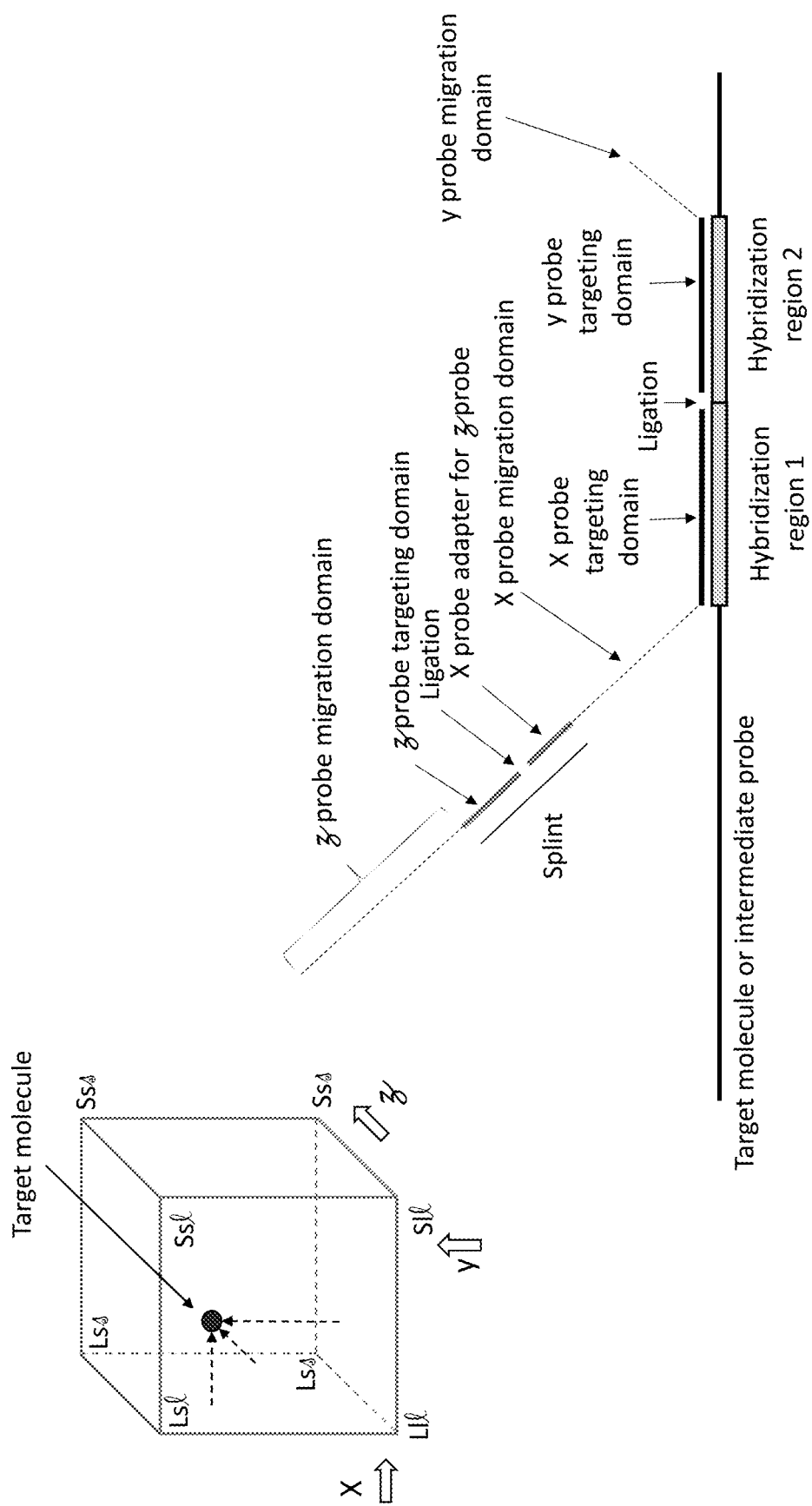
Figure 6C:
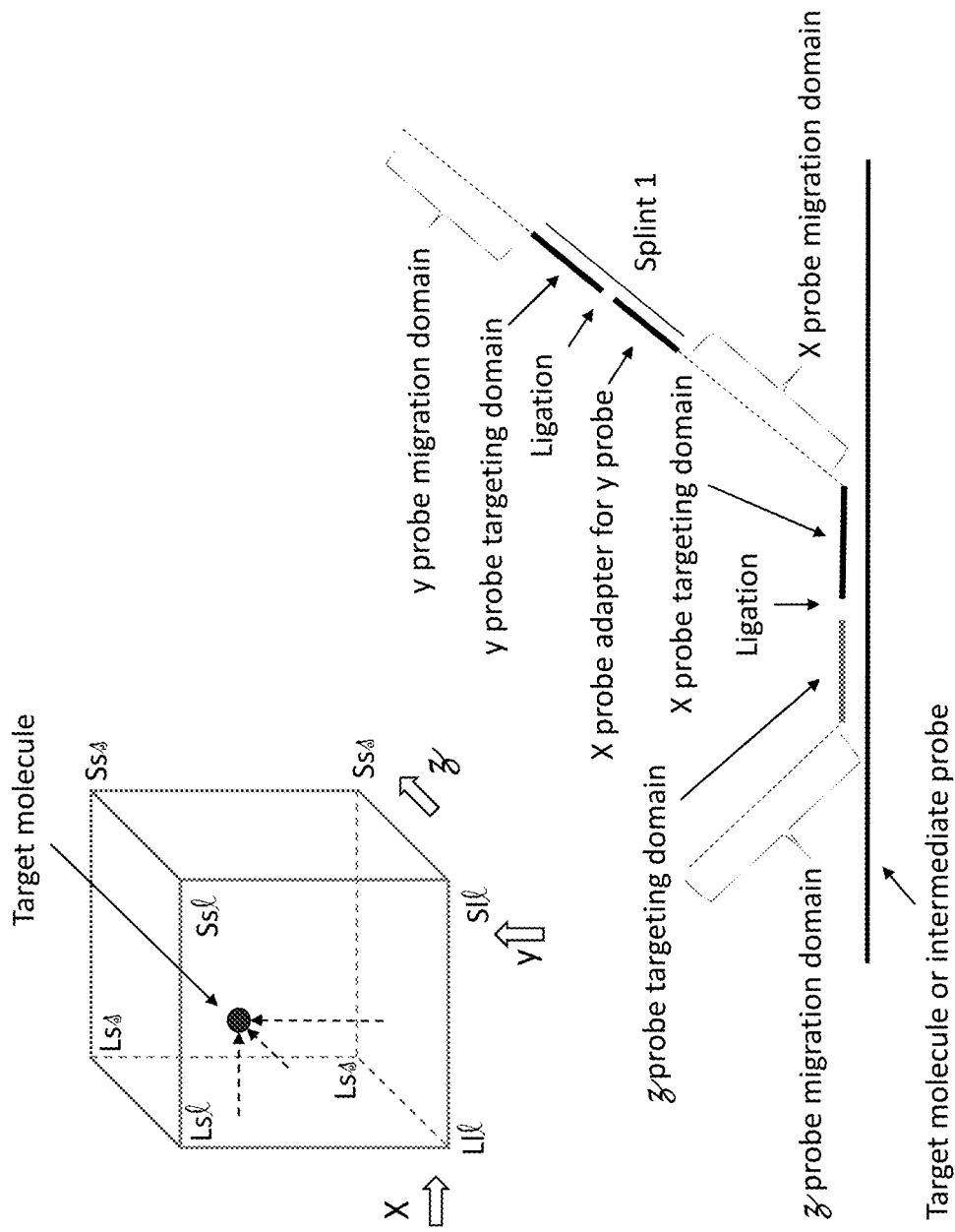

FIG. 6B shows an exemplary hybridization complex comprising X probe, a y probe, a 3′ probe, and a splint, wherein target nucleic acid serves as a splint for ligation of the X probe and the y probe, and the splint brings the X probe and the 3′ probe in proximity for ligation. In some embodiments, the 3′ probe is targeted to the y probe instead of the X probe. As will readily be appreciated by one of ordinary skill in the art, other variations are also possible, for example, wherein the X and 3′ probes hybridize to the target nucleic acid and the y probe hybridizes to a splint that is used to ligate it to one of the X or 3′ probes. The sequenced X, y, and 3′ probe complex can provide the identity of the target nucleic acid (e.g., via the sequence of a targeting domain (e.g., hybridizing sequence) complementary to the target nucleic acid) and the localization of the target nucleic acid in three-dimensional space (e.g., via the length of the variable-length sequences of the X, y, and ɜ́ probes). As shown in FIG. 6C, in another variation, the X probe and the ɜ́ probe may be ligated using the target nucleic acid as a splint.

Figure 6D:
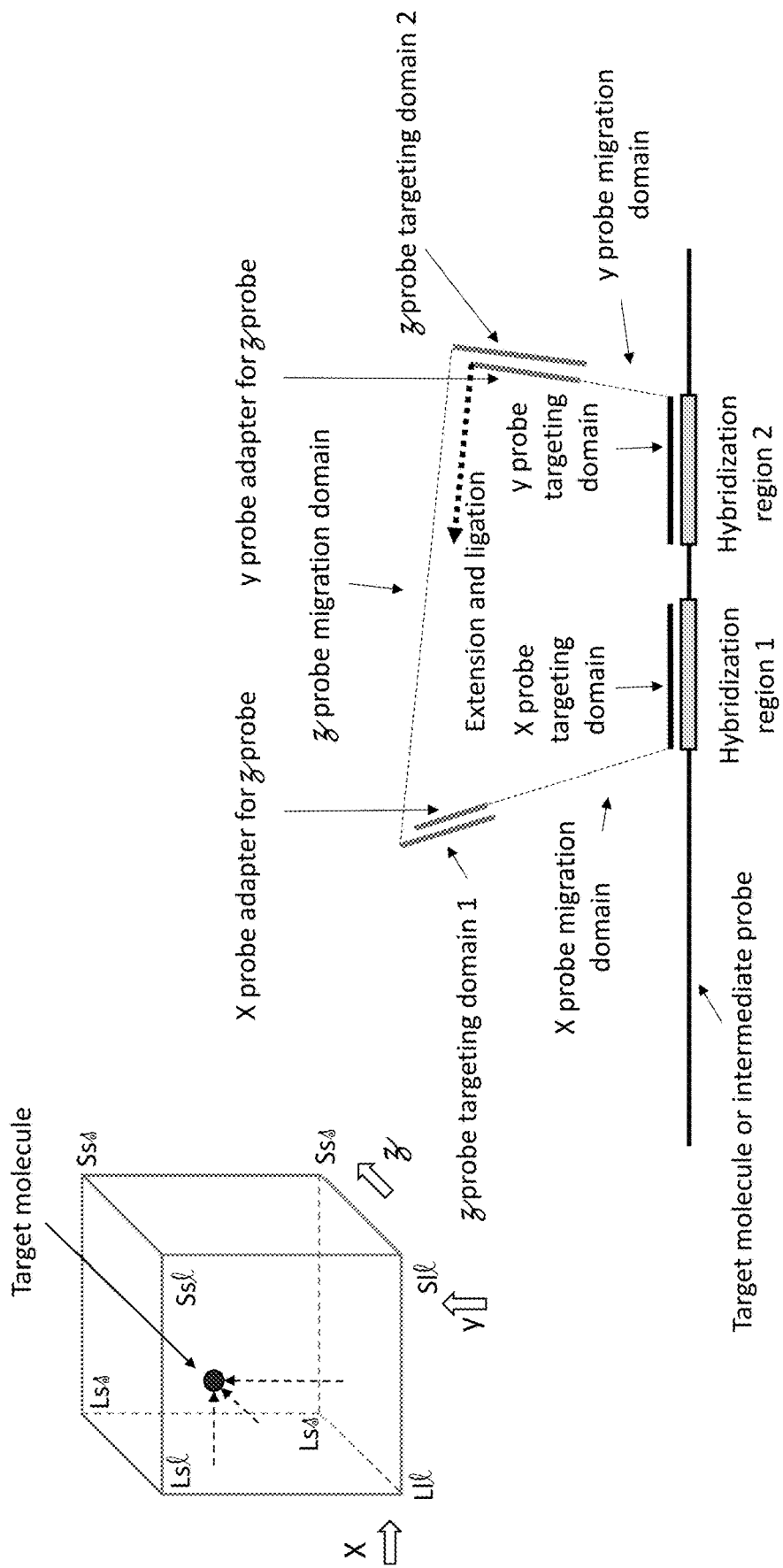

In some embodiments, one probe of the X, y and ɜ́ probes can serve as a template for extension and/or ligation of the other two probes. For example, as shown in FIG. 6D, an X probe and a y probe can hybridize to hybridization regions in a target nucleic acid, and a ɜ́ probe can hybridize to regions at the end of the X probe and at the end of the y probe. In some embodiments, the ɜ́ probe can serve as a template for extension of the X probe or y probe using a polymerase. In some embodiments, the ɜ́ probe can serve as a template for ligation of the X probe and the y-probe. In some embodiments, extension of the X probe or y probe using the ɜ́ probe as a template incorporates information regarding the sequence of the ɜ́ probe into the X or y probe.

Figure 7A:
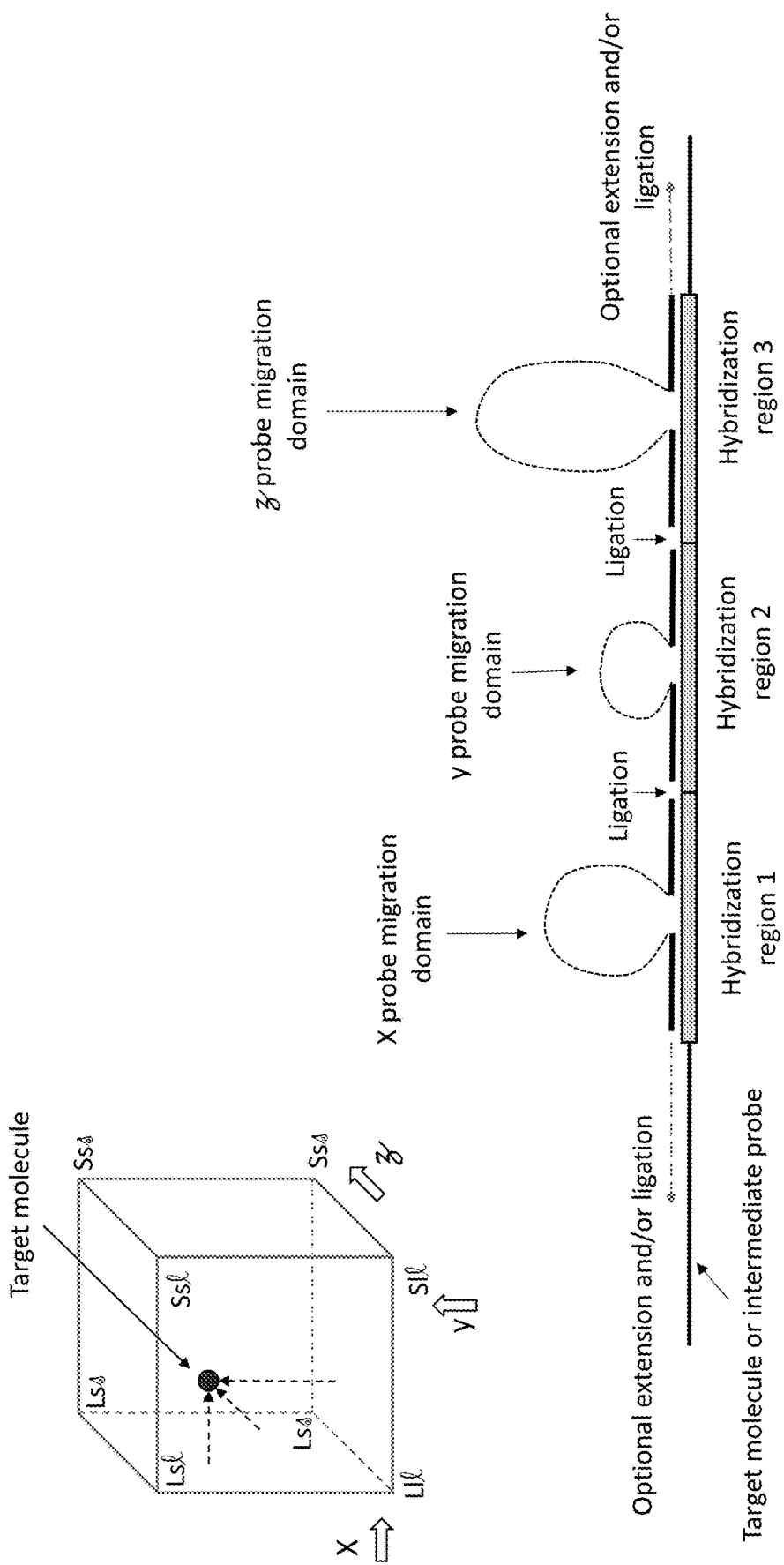
FIGS. 7A-7B show exemplary hybridization complexes formed by X, y, and $\mathcal{Z}$ probes with a target molecule or intermediate probe. Optionally, the targeting domains (e.g., hybridizing sequences) of the X, y and/or $\mathcal{Z}$ probes, can be split regions of the probe, and the migration domain (e.g., variable-length sequence) and/or migration barcode (e.g., length barcode) can form a loop that does not bind to the target molecule or intermediate probe. In some embodiments, the target molecule or intermediate probe can comprise adjacent hybridization regions that hybridize to the targeting domains (e.g., hybridizing sequences) of the X, y, and ¾ probes, and can serve as a template for ligation of the X, y, and/or ¾ probes.
Figure 7B:
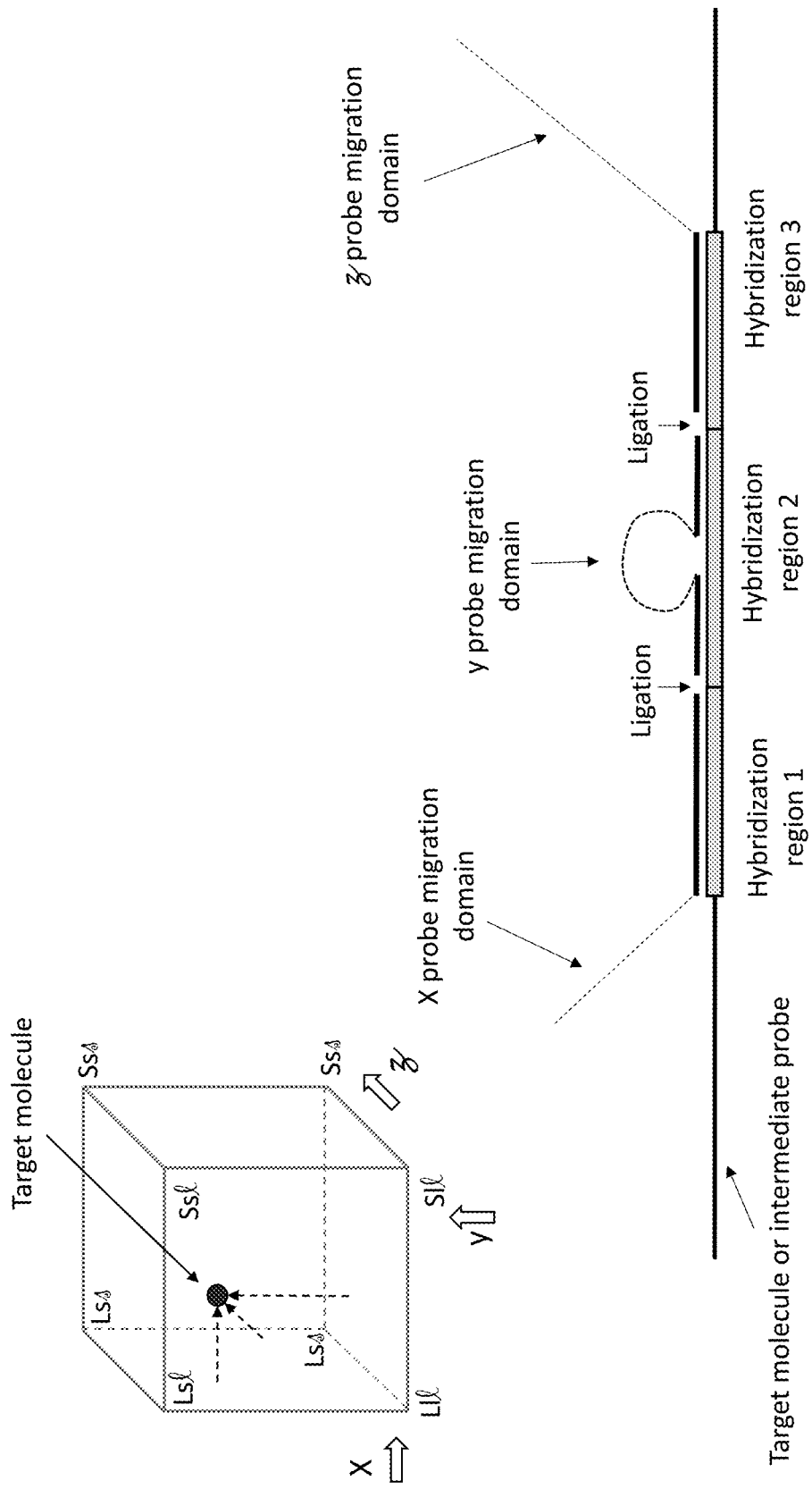

FIG. 7A shows an exemplary hybridization complex wherein an X probe, y, probe, and ɜ́ probe hybridize to adjacent hybridization regions of a target nucleic acid. In some embodiments as shown in FIG. 7A, each of the X probes, y probes, and ɜ́ probes can comprise a split hybridizing sequence, wherein the migration domain (e.g., variable-length sequence) (and optionally, the migration barcode) are located within the hybridizing sequence, and form a loop that does not hybridize to the target nucleic acid. In some embodiments, the hybridization regions for the X, y and ɜ́ probes are the same, and the same set of probes can be used for the target nucleic acid molecule in the x-, y-, and z-directions. In some embodiments, the hybridization regions for the X, y and ɜ́ probes can be different. In some embodiments, the target nucleic acid molecule can be used as a template for ligation of the hybridized X, y, and ɜ́ probes. In some embodiments, only X, y and ɜ́ probes that have hybridized to the target nucleic acid can be ligated together to form an X, y, and ɜ́ probe complex. As shown in FIG. 7B, alternative probe designs can also be used, wherein one or more of the X, y, and/or ɜ́ probes shows an exemplary hybridization complex formed by X, y, and ɜ́ probes with a target nucleic acid. Optionally, the targeting domains (e.g., hybridizing sequences) of the X, y and/or ɜ́ probes, can be split regions of the probe, and the migration domain (e.g., variable-length sequence) and/or migration barcode (e.g., length barcode) can form a loop that does not bind to the target nucleic acid. In some embodiments, the target nucleic acid (or intermediate probe) can comprise adjacent hybridization regions that bind to the targeting domains (e.g., hybridizing sequences) of the X, y, and ɜ́ probes, and can serve as a template for ligation of the X, y, and/or ɜ́ probes.

Figure 8:
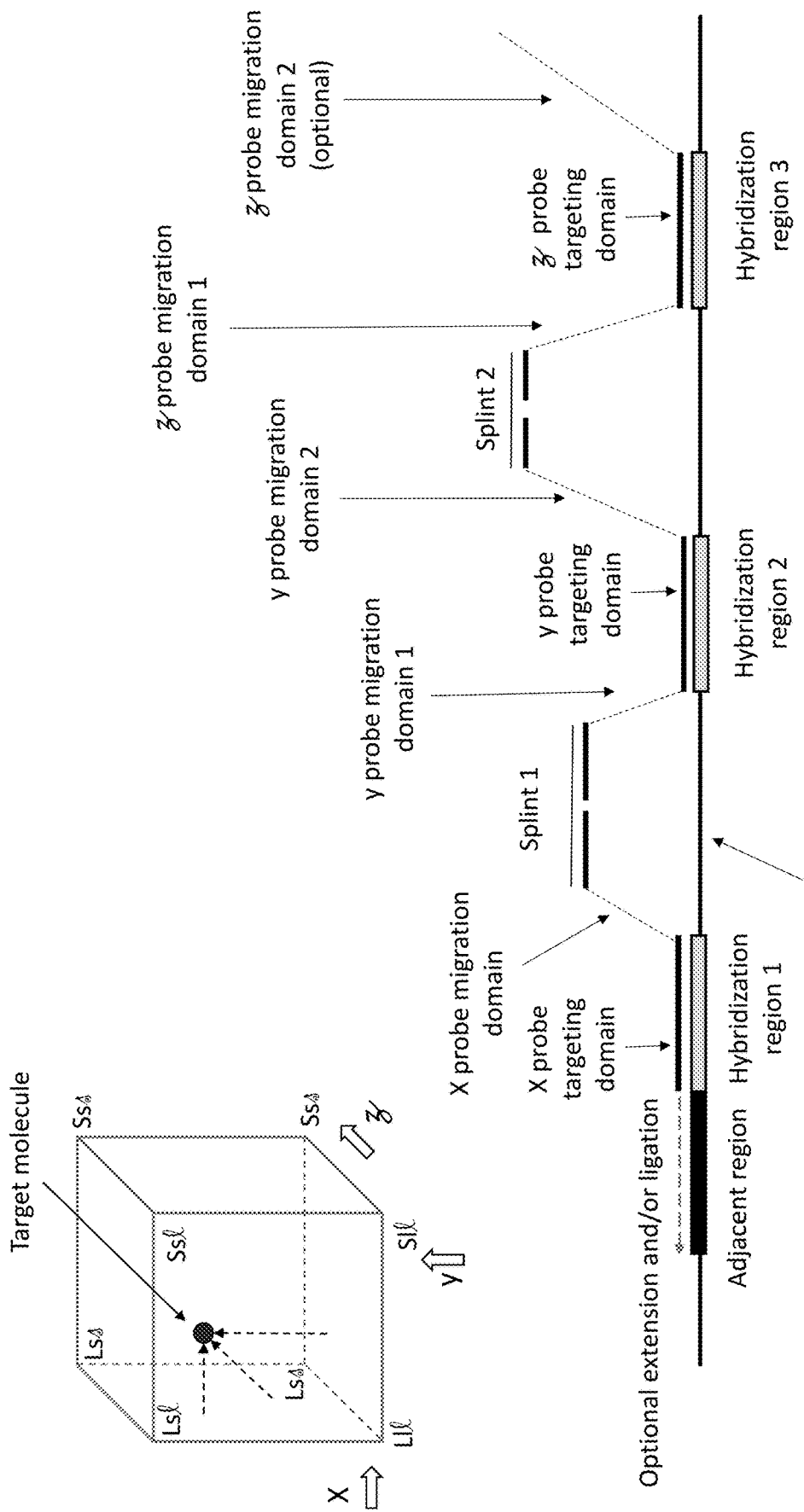
FIG. 8 shows an exemplary hybridization complex formed by X, y, and ¾ probes with a target molecule or intermediate probe and splints. In any of the depicted hybridization complexes, any of the probes may comprise a migration barcode sequence.

In some embodiments, the X, y, and ɜ́ probes may each hybridize to a target molecule or an intermediate probe. FIG. 8 shows an exemplary hybridization complex formed by X, y, and ɜ́ probes with a target nucleic acid and splints that can be used to connect the X, y, and ɜ́ probes. The connected X, y, and ɜ́ probes can be extended using the target molecule or the intermediate probe as a template, and the extended probe complex can provide information regarding the location and identity of the analyte of interest.

Although the above describes dispersal of oligonucleotides throughout a three-dimensional space by migration (e.g., by electrophoresis) in an x-, y- and z-dimension, there may be other ways to disperse oligonucleotides throughout a multidimensional space. In some examples, the oligonucleotides may be migrated through two dimensions instead of three dimensions. In some examples, oligonucleotides may be migrated through one dimension instead of two or three dimensions. In some examples, the dimensions through which the oligonucleotides are migrated may not be at right angles to one another as, for example, the x-dimension is to the y-dimension. In some examples, migration of oligonucleotides through a space may use multiple migrations of oligonucleotides through the same or closely related directions or dimensions. For example, oligonucleotides may be migrated through an x-dimension two, three, four, five or more times. In some examples, oligonucleotides may be electrophoresed through an x-dimension of a medium, the separated oligonucleotides immobilized in the medium, then oligonucleotides electrophoresed through the x-dimension a second time and immobilized, then a third time and immobilized, and so on. In some examples, the conditions of electrophoresis may be varied between the different electrophoresis runs to facilitate dispersal of the oligonucleotides throughout the entirety of a multidimensional space.

In some examples, a preformed medium may contain oligonucleotides, or some other markers of location, already dispersed throughout the preformed medium. The preformed medium containing location markers may be assembled around and/or throughout a tissue sample. Interrogation of the location markers, in relation to nucleic acid molecules and/or cells in the tissue sample, may provide spatial information related to the nucleic acid molecules and/or cells. In some examples, assembly of a medium around/throughout a tissue sample may involve sequential polymerization to create polymers.

A. Oligonucleotides (e.g., Probes)

Disclosed here are oligonucleotides (e.g., probes such as a first-dimension spatial probe, second-dimension spatial probe, and third-dimension spatial probe) for use in the methods described in this application. In some embodiments, the oligonucleotides (e.g., probes) comprise a migration domain which influences the migration of the oligonucleotide through the sample (e.g., the polymer matrix containing the target molecules). For example, a spatial probe (influenced by the migration properties of the migration domain) is migrated to a location in the biological sample in the respective dimension. In some aspects, the property of the migration domain (e.g., size or length) can be used to identify a corresponding location in the biological sample in the respective dimension that the spatial probe is migrated to. In some examples, the disclosed oligonucleotides of a population may have different lengths (e.g., as the migration domain). In some examples, the disclosed oligonucleotides comprise a nucleotide sequence that correlates with, identifies, or is linked to length or size of the oligonucleotide. These sequences, when determined in an oligonucleotide by nucleotide sequencing, can be used to identify the length of the oligonucleotide. These nucleotide sequences may be barcode nucleotide sequences, as known in the art. The nucleotide sequences that are linked to or correlate with oligonucleotide length may be called migration barcode (e.g., length barcode) sequences. In some embodiments, any of the probes may comprise an optional migration barcode sequence that identifies or is associated with the migration domain.

In some embodiments, the oligonucleotides (e.g., probes) comprises a targeting domain for associating with or binding to a target molecule in the sample. In some examples, the oligonucleotides disclosed here comprise a targeting domain comprising a nucleotide sequence that is capable of hybridizing to or identifying another nucleic acid molecule. These sequences within the disclosed oligonucleotides may be referred to as hybridizing nucleotide sequences and may be used to identify specific target nucleic acid molecules by specifically hybridizing to complementary sequences within the molecules. In some examples, the specific target nucleic acid molecules identified are RNA molecules. These hybridizing nucleotide sequences in an oligonucleotide, in various examples, may be designed to hybridize to a specific RNA molecule, to a probe that has specifically hybridized to the RNA molecule, and/or to a nucleic acid molecule that has been synthesized, amplified or ligated using the specific RNA molecule as a template.

In other embodiments, the hybridizing nucleotide sequences may be designed to hybridize to a reporter oligonucleotide that corresponds to a labelling agent. The labeling agent may be a protein binding agent that comprises a reporter oligonucleotide (e.g., an antibody conjugated to a reporter oligonucleotide which identifies the antibody) or a cell labeling agent that comprises a reporter oligonucleotide (e.g., either an antibody that specifically binds an extracellular protein or a lipid-based molecule conjugated to a reporter oligonucleotide). The cell labelling agent may be added to the tissue sample prior to the migration of oligonucleotides as described herein (e.g., one or more different cell labelling agent(s) having different reporter oligonucleotides may be added to specific region(s) of a tissue sample) and the reporter oligonucleotides may be detected downstream. Other cell labelling agents include, without limitation, a lipophilic moiety (e.g., cholesterol), a nanoparticle, a cell-penetrating peptide, a peptide-based chemical vector, a dye, and a fluorophore. Those of ordinary skill in the art will appreciate that other labeling agents with reporter oligonucleotides that are suitable for use in the present invention (see US Published Patent Application Nos. US20200002763 A1, US20190367969 A1, US 20190323088 A1, each of which is incorporated herein by reference in its entirety). In some examples, specific hybridizing nucleotide sequences may correlate with or be linked to a nucleotide sequence within the oligonucleotide. These sequences, when ascertained in an oligonucleotide by nucleotide sequencing, can be used to identify the specific hybridizing nucleotide sequence within an oligonucleotide (or a derivative thereof), and/or to identify a cellular analyte (e.g., an RNA) to which the hybridizing nucleotide sequence has hybridized, a probe that has hybridized to the cellular analyte (e.g., a specific RNA), and/or a nucleic acid molecule that has been synthesized, amplified or ligated using the cellular analyte (e.g., a specific RNA molecule) as a template, and/or a reporter oligonucleotide that identifies a labeling agent (as described herein). These nucleotide sequences may be barcode nucleotide sequences, as known in the art.

In some examples, the disclosed oligonucleotides may comprise a barcode nucleotide sequence (e.g., migration barcode sequence) linked to length of the oligonucleotides, a hybridizing nucleotide sequence (e.g., targeting domain), and barcode nucleotide sequence linked to the specific hybridizing nucleotide sequence.

Also disclosed here are populations of oligonucleotides as described above. Some example populations of oligonucleotides contain oligonucleotides of different lengths. An example of such a population of oligonucleotides is shown in FIG. 3A. The illustrated population of oligonucleotides contains oligonucleotides of 6 different lengths. As shown the oligonucleotides in the example population may comprise a migration barcode (e.g., length barcode) sequence, which correlates with or is linked to length of individual oligonucleotides. Because each of the 6 oligonucleotides in the population shown in FIG. 3A have different lengths, the migration barcode (e.g., length barcode) nucleotide sequence for each of the oligonucleotides shown will be different. Also, as shown in FIG. 3A, the oligonucleotides comprise a hybridizing nucleotide sequence, used for identifying other nucleic acid molecules. Optionally, the hybridizing nucleotide sequence may be linked to a hybridizing barcode nucleotide sequence. In some example populations of oligonucleotides, the hybridizing nucleotide sequence is the same in individual oligonucleotides of a population. In such populations, the optional hybridizing barcode nucleotide sequence will be the same in the oligonucleotides of the population.

In some examples, oligonucleotides in a population of oligonucleotides, or in a combination of populations, may comprise an additional barcode sequence. This barcode sequence may be used to determine in which dimension the oligonucleotides in the population, or in a combination of populations, were migrated. For example, oligonucleotides migrated through a multidimensional space in a x-dimension may comprise a common first barcode nucleotide sequence. Oligonucleotides migrated through the multidimensional space in a y-dimension may comprise a common second barcode nucleotide sequence. Oligonucleotides migrated through the multidimensional space in a z-dimension may comprise a common third barcode nucleotide sequence. After the migration, identification of these barcodes in an oligonucleotide provides information on the dimension through which the oligonucleotide was migrated.

In some examples, the oligonucleotides of different lengths within a population may rely on a particular region of the oligonucleotides to provide the different lengths. In some examples, the oligonucleotides of a population may be of identical length, except for a specific part of each oligonucleotide that provides the different lengths. FIG. 3A illustrates such an example population of oligonucleotides. In the oligonucleotides of FIG. 3A, the sum of the lengths of the migration barcode (e.g., length barcode) sequence and the hybridizing nucleotide sequence are the same in the different oligonucleotides. A sequence designated as a migration domain (e.g., variable-length sequence) provides for different lengths of the oligonucleotides of the population. In some examples, the migration domain (e.g., variable-length sequence) may be part of the 5'end of the oligonucleotides in the population. In some examples, the migration domain (e.g., variable-length sequence) may be part of the 3'end of the oligonucleotides in the population. In some examples, the migration domain (e.g., variable-length sequence) may be internal to the ends of the oligonucleotides in the population.

In any of the embodiments herein, the migration domain can comprise moieties besides nucleic acids. The migration domain can comprise nucleic acid variants or analogues (regardless of whether genetic information in these variants or analogues can be read and duplicated by a natural polymerase) and/or non-nucleic acid moieties. In some embodiments, the migration domain comprises a charged domain, a size-specific domain, an electromagnetic domain, or any combination thereof. In some embodiments, the migration domain comprises a folded oligonucleotide domain. In some embodiments, the folded oligonucleotide domain is a folded three-dimensional oligonucleotide domain. In some embodiments, the migration domain comprises a protein domain. In some embodiments, the protein domain comprises multiple subunits. In some embodiments, the protein domain comprises biotin, avidin, or streptavidin.

In some embodiments, the migration domain comprises a polyethylene glycol. The migration domains of a population of oligonucleotides disclosed herein (e.g., the first-dimension spatial probes, the second-dimension spatial probes, and/or the third-dimension spatial probes) can be programmed such that the migration barcode sequence of a spatial barcode in the population corresponds to the size of the migration domain and/or the relative location of the spatial probe among spatial probes in that population migrating in the sample (e.g., under the same electrophoresis conditions).

In any of the embodiments herein, the first-dimension, second-dimension, and/or third-dimension spatial probe can be processed. In any of the embodiments herein, the migration domain or a portion thereof can be cleaved from its spatial probe once the spatial probe is migrated to a location in the respective dimension. In any of the embodiments herein, the migration domain or a portion thereof can be cleaved from its spatial probe once the spatial probe is targeted to the target molecule, the first-dimension spatial probe targeted thereto, and/or the second-dimension spatial probe targeted thereto. In any of the embodiments herein, the migration domain or a portion thereof can be cleaved from the product once it is generated in the biological sample, for instance, in order to reduce the size of the product for sequencing analysis but without separating spatial information encoded in the sequences of the spatial probes from information of the target molecule. Thus, nucleic acid variants or analogues (especially those that cannot be read and duplicated by a natural polymerase) and/or non-nucleic acid moieties, if present in the migration domain when the spatial probes are migrated and distributed in the sample, may be removed from the spatial probe once the spatial probe reaches its destination, once the spatial probe binds to a target molecule or a previous spatial probe linked to the target molecule, or once a product comprising information of three-dimensional spatial probes and the target molecule is generated. In some embodiments, processing one or more of the spatial barcodes and/or the products may also help reduce the lengths of nucleic acid sequences that need to be sequenced in order to associate target molecule information with its three-dimensional spatial information.

B. Methods

Having described oligonucleotides and populations of oligonucleotides in the previous section, and referring back to the earlier section of this application related to dispersing oligonucleotides in three-dimensional space, it can be understood that a population of oligonucleotides of different lengths, where individual oligonucleotides of the population comprise the same hybridizing nucleotide sequence, can be used to interrogate a three-dimensional space for presence of a cellular analyte (e.g., an RNA) that is complementary to the hybridizing nucleotide sequence in the oligonucleotides and to quantitatively describe the relative locations of those cellular analytes (e.g., RNAs) in the three-dimensional space.

For example, in the experiment described in FIG. 2, consider that the cube through which oligonucleotides were electrophoresed contained a tissue sample that had been interrogated for cellular analytes (e.g., specific RNAs). In some examples, interrogation of the tissue sample for specific RNAs may involve fixing the tissue, probing the tissue for specific RNAs using RNA capturing probes that hybridize to a complementary sequence in the RNA, amplification of the RNA sequence using synthesis (e.g., PCR, RT-PCR) or ligation, and the like. Such techniques are known in the art (see Wang et al., *Science* 361, 380, 2018).

Also consider that the tissue sample that had been interrogated for cellular analytes (e.g., specific RNAs), as above, may be embedded in a medium, such as a conductive polymer. A type of conductive polymer may be a conductive hydrogel. Conductive hydrogels, and embedding tissue or cell samples within conductive hydrogels, are known in the art. U.S. Pat. Publ. No. 2011/0256183 (Frank et al.), U.S. Pat. No. 10,138,509 (Church et al.), U.S. Pat. No. 10,545,075 (Deisseroth et al.) and U.S. Pat. Publ. No. 2019/0233878 (Delaney, et al.) which are herein incorporated by reference, describe hydrogels and their use for embedding tissues and cells. In some examples, the target nucleic acid molecules (e.g., RNAs, RNA capturing probes, and extended or amplified sequences from the RNA or capturing probes), as described in the previous paragraph, are cross-linked to the hydrogel and/or to each other.

Then, consider that the population of oligonucleotides that has been migrated through the x-dimension, through the y-direction and through the z-dimension of the hydrogel-embedded tissue sample in FIG. 2 are the same populations (the oligonucleotides all comprise the same hybridizing nucleotide sequence). At the conclusion of this electrophoresis experiment, an oligonucleotide encoding the same hybridizing nucleotide sequence would be present throughout the three-dimensional space of the hydrogel-embedded tissue sample.

By placing the hydrogel-embedded tissue sample under conditions such that the hybridizing nucleotide sequence in the oligonucleotides can hybridize to their complementary nucleotide sequence in a target nucleic acid molecule (e.g., an RNA, RNA capturing probe or amplification/ligation product of an RNA or RNA capturing probe), and then obtaining the nucleotide sequence of oligonucleotides that have hybridized to their complementary nucleotide sequence, information can be obtained as discussed below.

First, because the oligonucleotides dispersed throughout the hydrogel contained hybridizing nucleotide sequences capable of hybridizing to or identifying the target nucleic acid molecule (e.g., the same RNA, oligonucleotides that have hybridized and formed duplexes with the RNA or products thereof) indicate presence of that target nucleic acid molecule (e.g., specific RNA).

Second, by obtaining the nucleotide sequences of the duplexed oligonucleotides, the length of specific oligonucleotides would be known. In some examples, the nucleotide sequence of a migration barcode (e.g., length barcode) nucleotide sequence present in the oligonucleotide would provide this information. Because the original populations of oligonucleotides that were electrophoresed through the x-, y- and z-dimensions of the hydrogel were separated according to size in each of the three dimensions, location of the sequenced oligonucleotide in the hydrogel can be determined from its size. Knowledge of the dimension (x, y or z) in which the sequenced oligonucleotide was originally electrophoresed is helpful here. This can be obtained by including a common nucleotide sequence barcode among oligonucleotides that were electrophoresed in the x-dimension, a common, different barcode sequence among oligonucleotides that were electrophoresed in the y-dimension, and a common, different barcode sequence among oligonucleotides that were electrophoresed in the z-dimension. From knowledge of oligonucleotide length in combination with the dimension in which the oligonucleotide was electrophoresed, the relative location of the oligonucleotide (x-, y- and z-dimensions, as already discussed for FIG. 2) can be determined.

By combining knowledge of the target nucleic acid molecule (e.g., specific RNA) detected with the information on its three-dimensional location, a high-density, quantitative, three-dimensional map of relative distribution of the target nucleic acid molecule (e.g., the specific RNA) throughout the three-dimensional space is obtained.

Further, in the above-described experiment, the populations of oligonucleotides that are electrophoresed in the x-, y- and z-dimensions and are dispersed throughout the hydrogel comprise the same hybridizing nucleotide sequence. The single hybridizing nucleotide sequence generally hybridizes only to target nucleic acid molecules (e.g., RNAs or amplification/ligation products thereof) that contain a complementary sequence. Thus, in many cases, this experiment would identify a single target nucleic acid molecule (e.g., a single RNA).

Now consider that individual oligonucleotides in the populations of oligonucleotides that were electrophoresed in the x-, y- and z-dimensions contained hybridizing nucleotide sequences that were different from one another, and that the different sequences were capable of identifying different target nucleic acid molecules (e.g., RNAs or amplification/ligation products thereof). In some examples, oligonucleotides containing the same hybridizing nucleotide sequences comprise a common barcode nucleotide sequence. Using such oligonucleotide populations, expression of multiple target nucleic acid molecules (e.g., multiple RNAs) in the tissue would be determined in the experiment. In some examples, the number of RNAs that could be interrogated may be no less than 50, 100, 500, 1,000, 10,000, 50,000, or more. In this way, a high-density, quantitative, three-dimensional map of relative distribution of the target nucleic acid molecules (e.g., specific RNA) throughout the three-dimensional space is obtained.

Some features of the methods disclosed here are now described. First, the spatial information obtained from the methods does not depend on visual observation of an intact three-dimensional hydrogel. In the inventive method, oligonucleotides that have hybridized to target nucleic acid molecules (e.g., RNA-derived extension products or amplicons) in the hydrogel are extracted from the hydrogel, libraries are constructed and sequenced. Cellular analyte information (e.g., RNA expression) and spatial information come from the nucleotide sequences. Second, cellular analyte information (e.g., expression of many RNAs) can be determined in a single experiment. In some examples, expression of a tissue's complete transcriptome, a tissue's targeted transcriptome and/or aspects of a tissue's proteome may be studied in an experiment. A complete transcriptome experiment avoids bias that may occur when only subsets of the transcriptome are chosen for study.

In some embodiments, the method comprises generating a product in the biological sample, the product comprising: (1) a sequence or complement thereof of the migration domains and/or the migration barcode sequences of the first-dimension spatial probe, the second-dimension spatial probe, and the third-dimension spatial probe; and (2) a sequence corresponding to the target molecule; and (e) determining a sequence of the product, thereby identifying the location of the target molecule in a three-dimensional space in the biological sample.

In some embodiments, the product is a ligation product comprising: (1) a sequence or complement thereof of the migration domains and/or the migration barcode sequences of the first-dimension spatial probe, the second-dimension spatial probe, and the third-dimension spatial probe; and (2) a sequence corresponding to the target molecule. In some embodiments, the ligation product is a ligation product of the first-dimension spatial probe, the second-dimension spatial probe, and the third-dimension spatial probe. In some embodiments, the ligation product further comprises a ligated intermediate probe (e.g., an adapter) that hybridized to the target molecule. In some embodiments, the ligation product can be further extended using a polymerase (e.g., to incorporate a sequence or an additional sequence corresponding to the target molecule).

In some embodiments, the ligation herein is a proximity ligation of ligating two (or more) nucleic acid sequences that are in proximity with each other, e.g., through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

In some embodiments, the ligation involves chemical ligation. In some embodiments, the chemical ligation involves click chemistry. In some embodiments, the ligation involves template dependent ligation. In some embodiments, the ligation involves template independent ligation. In some embodiments, the ligation involves enzymatic ligation. In some embodiments, the ligation product is generated using one or more splint nucleic acid molecules comprising one or more sequences complementary to any of the spatial probes).

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has a DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides (e.g., spatial probes) hybridize immediately adjacently to one another to form a substrate for a ligase enzyme resulting in their ligation to each other (intramolecular ligation). Alternatively, "indirect" means that the ends of the polynucleotides (e.g., spatial probes) hybridize non-adjacently to one another, i.e., separated by one or more intervening nucleotides or "gaps". In some embodiments, said ends are not ligated directly to each other, but instead occurs either via the intermediacy of one or more intervening (so-called "gap" or "gap-filling" (oligo)nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, padlock probe, or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the spatial probes produces polynucleotides with melting temperature higher than that of spatial probes. Thus, in some aspects, ligation stabilizes the hybridization complex containing the ligated spatial probes prior to subsequent steps (e.g., subsequent migration steps).

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some embodiments, the method comprises generating an extension product in the biological sample, the product comprising: (1) a sequence or complement thereof of the migration domains and/or the migration barcode sequences of the first-dimension spatial probe, the second-dimension spatial probe, and/or the third-dimension spatial probe; and (2) a sequence corresponding to the target molecule. In some embodiments, the extension product is generated using a polymerase (e.g., to extend the 3' end of a spatial probe). In some embodiments, an extension product is generated for the first-dimension spatial probe, the second-dimension spatial probe, and the third-dimension spatial probe. In some embodiments, the target molecule or an intermediate probe bound directly or indirectly to the target molecule is used as the template for an extension reaction, thereby incorporating a sequence corresponding to the target molecule into the hybridized spatial probes. In some embodiments, the target molecule or intermediate probe comprises a barcode sequence that is used as the template for the extension reaction, wherein the barcode sequence corresponds to the target molecule.

Note that, nucleotide sequence information is obtained from migrated oligonucleotides after the medium in which the oligonucleotides have been separated is dissolved or depolymerized. A library resulting from oligonucleotides released from the medium in this process is subjected to nucleotide sequencing. In some embodiments, an extension reaction can be performed using the ligation product (or a portion thereof) as a template to further generate products for analysis (e.g., sequencing). Information on the location of the oligonucleotides within the three-dimensional medium is encoded by the oligonucleotides. The oligonucleotides contain a barcode that identifies the length of the oligonucleotide. In some embodiments, the oligonucleotides for analysis comprises a combination of sequences that identifies the length of spatial probes in two or three dimensions. Oligonucleotide migration through the medium is based on oligonucleotide size. The oligonucleotides also may also contain a barcode that identifies the dimension through which the oligonucleotide has been migrated. Each of these two pieces of information allow inference of the location of an oligonucleotide within a three-dimensional medium.

C. Devices and Systems

Disclosed here are devices for dispersing oligonucleotides throughout a three-dimensional space. In some examples, the devices may be used for electrophoresis of oligonucleotides throughout a multidimensional space to populate the space with the oligonucleotides. The devices may be configured to enable sequential generation of electric fields in multiple dimensions to distribute oligonucleotides throughout a multidimensional space.

In some examples, the device may include a chamber that can accommodate a three-dimensional tissue sample. The chamber of the device is generally configured to hold a volume of electrophoresis buffer into which a three-dimensional tissue sample can be submerged.

In some embodiments, electrophoresis can be applied to a biological sample while in contact with a permeabilization buffer. In some embodiments, electrophoresis can be applied to a biological sample while in contact with an electrophoresis buffer (e.g. a buffer that lacks permeabilization reagents). In some embodiments, the permeabilization buffer can be replaced with an electrophoresis buffer after a desired amount of time. In some embodiments, electrophoresis can be applied simultaneously with the permeabilization buffer or electrophoresis buffer. In some embodiments, electrophoresis can be applied after a desired amount of time of contact between the biological sample and the permeabilization buffer or electrophoresis buffer.

In some examples, the tissue sample may be fixed after placement in the chamber. In some examples, therefore, the chamber of the device is suitable for tissue fixation. In some examples, the chamber will be suitable for hybridizing nucleotide probes to nucleic acids contained within the tissue sample. In some examples, the chamber will be suitable for hybridizing nucleic acid probes (e.g., RNA capturing probes) to specific nucleic acid molecules (e.g., specific RNAs) that may be present within the tissue sample. The chamber may also be suitable for amplification reactions that produce complementary nucleotide sequences using the nucleic acid molecules and/or nucleic acid probes (e.g., RNA and/or RNA capturing probes) as templates. The chamber may also be suitable for performing ligation reactions that ligate molecules that hybridize to the nucleic acid molecules (e.g., RNA), nucleic acid probes (e.g., RNA capturing probes), or nucleic acid products (e.g., extension or amplification products), into larger molecules.

In some examples, the chamber of the device may be suitable for embedding a tissue sample in a medium, such as a hydrogel. In some examples, a liquid hydrogel solution may be poured into a chamber that contains the tissue sample. The hydrogel solution will polymerize, embedding the tissue sample in a polymerized hydrogel. The chamber will be configured so that the polymerized hydrogel that forms will provide for electrophoresis of oligonucleotides through the entirety of the embedded tissue sample.

Generally, the chamber of the device will also be suitable for performing steps to immobilize oligonucleotides in the hydrogel after the oligonucleotides have been electrophoresed through each dimension of the sample.

Generally, the chamber of the device may also be suitable for performing steps to retrieve complexes of oligonucleotides hybridized to target nucleic acid molecules described herein (e.g., RNAs, RNA capturing probes, amplification products to the RNAs/capturing probes, and the like), from the hydrogel so the complexes can be subjected to nucleotide sequencing.

The device may generally be configured to provide sample chambers to hold liquid samples of oligonucleotides in such a way that application of an electric field in, for example, the x-dimension through the hydrogel, results in oligonucleotides contacting the hydrogel and migrating through the entire area of a y-z plane drawn through one end of the x-dimension of the tissue sample. Similarly, sample chambers are provided to electrophorese through a y-dimension and a z-dimension of the tissue sample in the chamber. One possible configuration of sample chambers is illustrated in FIG. 9, as described below.

The device is generally configured so that electric fields can be generated by activating poles oriented in multiple directions. In some examples, the device is configured with electrodes so that electric fields can be separately and sequentially generated through an x-dimension, y-dimension and z-dimension of a hydrogel-embedded tissue located in the chamber of the device.

Figure 9:
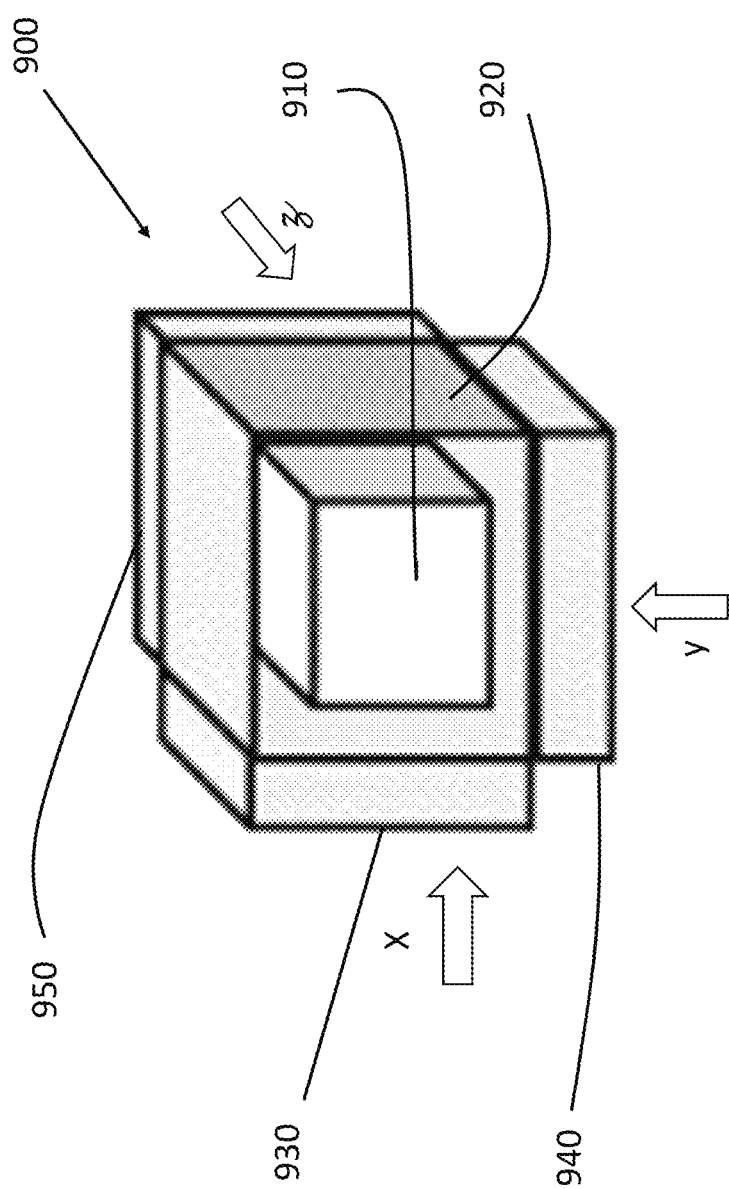
FIG. 9 illustrates an example electrophoresis apparatus.

One example of such a device is illustrated in FIG. 9. The device 900 may be configured to accommodate a three-dimensional tissue sample 910 in a chamber 920 that is part of the device. The device may have oligonucleotide sample chambers at one end of the chamber, in each of the x-, y- and z-dimensions (930, 940 and 950, respectively). The oligonucleotide sample chambers may provide for contacting a liquid sample containing oligonucleotides with the entire area of a plane perpendicular to the x-dimension, y-dimension and z-dimension of the device. This configuration of the oligonucleotide sample chambers provides for electrophoresis of oligonucleotides of different sizes through the three dimensions of the tissue sample such that the oligonucleotides populate the entire three-dimensional space of the tissue sample.

In some examples, the device may be configured to be repositioned between electrophoresis in each of the x-, y- and z-dimensions. For example, when electrophoresing in the x-dimension, the device may be positioned so the sample chamber for x-dimension electrophoresis is at the top of the device (not shown in FIG. 9). In this position, gravity may provide for oligonucleotides in the sample chamber to enter the tissue sample uniformly. Additionally, the device may be configured to be alternatively positioned such that the sample chamber for y-dimension electrophoresis is at the top of the device, and that the sample chamber for z-dimension electrophoresis is at the top of the device.

Generally, the devices disclosed herein may be part of systems for performing the disclosed methods. The systems are configured to perform various steps of the disclosed methods automatically. Some examples of automated steps may include loading and/or embedding a tissue sample in a polymer, loading a sample of oligonucleotides and migrating the oligonucleotides in the sample through the polymer, hybridizing the oligonucleotides to cellular RNAs and/or amplification products thereof that are present in the polymer, depolymerization and/or dissolution of the polymer to release the oligonucleotides, nucleotide sequencing of the oligonucleotides, data collection, data analysis, and others.

D. Analysis of Spatial Probes and Products Thereof

In some embodiments, the product is generated in the biological sample and comprises a sequence or complement thereof of the migration domains and/or the migration barcode sequences of the first-dimension spatial probe, the second-dimension spatial probe, and the third-dimension spatial probe; and a sequence corresponding to the target molecule. The product that results from the hybridization/association described herein can be analyzed via sequencing to identify the analytes and their relative locations in the three-dimensions in the biological sample.

In some embodiments, the product is released, removed, or isolated from the biological sample and then sequenced. In some embodiments, the product is not released, removed, or isolated from the biological sample, which is processed as a whole for sequencing analysis. In some cases, the product may be subjected to one or more processing steps to prepare the product for analysis. In some embodiments, the product for analysis may include one or more functional sequences that can be used in subsequent processing and/or analysis, such as an adapter sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

A wide variety of different sequencing methods can be used to analyze the generated products. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and any combinations thereof.

Sequence analysis of the nucleic acid molecules (including generated products described herein, barcoded nucleic acid molecules or derivatives thereof) can be direct or indirect. Thus, the sequence analysis substrate (which can be viewed as the molecule which is subjected to the sequence analysis step or process) can directly be the generated products described herein (e.g., comprising a sequence or complement thereof of the migration domains and/or the migration barcode sequences of the first-dimension spatial probe, the second-dimension spatial probe, and the third-dimension spatial probe; and a sequence corresponding to the target molecule) or it can be a molecule which is derived therefrom (e.g., a complement thereof). Thus, for example, in the sequence analysis step of a sequencing reaction, the sequencing template can be the generated product or it can be a molecule derived therefrom. For example, a first and/or second strand DNA molecule can be directly subjected to sequence analysis (e.g. sequencing), i.e., can directly take part in the sequence analysis reaction or process (e.g. the sequencing reaction or sequencing process, or be the molecule which is sequenced or otherwise identified). Alternatively, the nucleic acid molecule (e.g., generated product) can be subjected to a step of second strand synthesis or amplification before sequence analysis (e.g. sequencing or identification by another technique). The sequence analysis substrate (e.g., template) can thus be an amplicon or a second strand of a nucleic acid molecule.

In some embodiments, both strands of a double stranded molecule can be subjected to sequence analysis (e.g., sequenced). In some embodiments, single stranded molecules (e.g. generated product) can be analyzed (e.g. sequenced). To perform single molecule sequencing, the nucleic acid strand can be modified at the 3' end.

Massively parallel sequencing techniques can be used for sequencing nucleic acids, as described above. In one embodiment, a massively parallel sequencing technique can be based on reversible dye-terminators. As an example, DNA molecules are first attached to primers on, e.g., a glass or silicon substrate, and amplified so that local clonal colonies are formed (bridge amplification). Four types of ddNTPs are added, and non-incorporated nucleotides are washed away. Unlike pyrosequencing, the DNA is only extended one nucleotide at a time due to a blocking group (e.g., 3' blocking group present on the sugar moiety of the ddNTP). A detector acquires images of the fluorescently labelled nucleotides, and then the dye along with the terminal 3' blocking group is chemically removed from the DNA, as a precursor to a subsequent cycle. This process can be repeated until the required sequence data is obtained.

As another example, massively parallel pyrosequencing techniques can also be used for sequencing nucleic acids. In pyrosequencing, the nucleic acid is amplified inside water droplets in an oil solution (emulsion PCR), with each droplet containing a single nucleic acid template attached to a single primer-coated bead that then forms a clonal colony. The sequencing system contains many picolitre-volume wells each containing a single bead and sequencing enzymes. Pyrosequencing uses luciferase to generate light for detection of the individual nucleotides added to the nascent nucleic acid and the combined data are used to generate sequence reads.

As another example application of pyrosequencing, released PPi can be detected by being immediately converted to adenosine triphosphate (ATP) by ATP sulfurylase, and the level of ATP generated can be detected via luciferase-produced photons, such as described in Ronaghi, et al., Anal. Biochem. 242(1), 84-9 (1996); Ronaghi, Genome Res. 11(1), 3-11 (2001); Ronaghi et al. Science 281 (5375), 363 (1998); and U.S. Pat. Nos. 6,210,891, 6,258,568, and 6,274,320, the entire contents of each of which are incorporated herein by reference.

In some embodiments, sequencing is performed by detection of hydrogen ions that are released during the polymerization of DNA. A microwell containing a template DNA strand to be sequenced can be flooded with a single type of nucleotide. If the introduced nucleotide is complementary to the leading template nucleotide, it is incorporated into the growing complementary strand. This causes the release of a hydrogen ion that triggers a hypersensitive ion sensor, which indicates that a reaction has occurred. If homopolymer repeats are present in the template sequence, multiple nucleotides will be incorporated in a single cycle. This leads to a corresponding number of released hydrogen ions and a proportionally higher electronic signal.

In some embodiments, where the intermediate probe as shown in FIG. 5B) do not contain a spatial barcode, the spatial barcode can be added after the intermediate probe binds the analytes from a biological sample and before analysis of the analytes. In some embodiments, the barcode can be added after amplification of the analyte. In some embodiments, a spatial barcode is added after amplification of a nucleic acid (e.g., DNA or RNA) sequence in an analyte, and the analyte may include an endogenous nucleic acid (e.g., DNA or RNA) molecule in the sample, a DNA or RNA molecule added to the sample, a DNA or RNA molecule generated in the sample (e.g., a reverse transcription product, a polymerase extension product, a ligation product such as a templated ligation product, and/or an amplification product such as an RCA product). In some embodiments, a spatial barcode is added after reverse transcription of an RNA and polymerase amplification of a cDNA). In some embodiments, the analysis may comprise direct sequencing of an endogenous nucleic acid (e.g., DNA or RNA) molecule in the sample, a DNA or RNA molecule added to the sample (e.g., a probe or labelling agent that directly or indirectly hybridizes/binds to an analyte), a DNA or RNA molecule generated in the sample (e.g., a reverse transcription product, a polymerase extension product, a ligation product such as a templated ligation product, and/or an amplification product such as an RCA product). In some embodiments, direct sequencing is performed after reverse transcription of a target RNA and attachment of the x-, y-, and z-spatial barcodes. In some embodiments direct sequencing is performed after amplification of a reverse transcript of a target RNA and attachment of the x-, y-, and z-spatial barcodes to the amplification product or a probe recognizing the amplification product.

In some embodiments, direct sequencing is performed by sequencing-by-synthesis (SBS). In some embodiments, a sequencing primer is complementary to a functional sequence added to or comprised by the generated products comprising a sequence or complement thereof of the migration domains and/or the migration barcode sequences of the first-dimension spatial probe, the second-dimension spatial probe, and the third-dimension spatial probe; and a sequence corresponding to the target molecule) (e.g., or a derivative thereof). In such embodiments, sequencing-by-synthesis can include reverse transcription and/or amplification in order to generate a template sequence (e.g., functional sequence) from which a primer sequence can bind.

SBS can involve hybridizing an appropriate primer, sometimes referred to as a sequencing primer, with the nucleic acid template to be sequenced, extending the primer, and detecting the nucleotides used to extend the primer. Preferably, the nucleic acid used to extend the primer is detected before a further nucleotide is added to the growing nucleic acid chain, thus allowing base-by-base in situ nucleic acid sequencing. The detection of incorporated nucleotides is facilitated by including one or more labelled nucleotides in the primer extension reaction. To allow the hybridization of an appropriate sequencing primer to the nucleic acid template to be sequenced, the nucleic acid template should normally be in a single stranded form. If the nucleic acid templates making up the nucleic acid spots are present in a double stranded form these can be processed to provide single stranded nucleic acid templates using methods well known in the art, for example by denaturation, cleavage etc. The sequencing primers which are hybridized to the nucleic acid template and used for primer extension are preferably short oligonucleotides, for example, 15 to 25 nucleotides in length. The sequencing primers can be provided in solution or in an immobilized form. Once the sequencing primer has been annealed to the nucleic acid template to be sequenced by subjecting the nucleic acid template and sequencing primer to appropriate conditions, primer extension is carried out, for example using a nucleic acid polymerase and a supply of nucleotides, at least some of which are provided in a labelled form, and conditions suitable for primer extension if a suitable nucleotide is provided.

Preferably after each primer extension step, a washing step is included in order to remove unincorporated nucleotides which can interfere with subsequent steps. Once the primer extension step has been carried out, the nucleic acid colony is monitored to determine whether a labelled nucleotide has been incorporated into an extended primer. The primer extension step can then be repeated to determine the next and subsequent nucleotides incorporated into an extended primer. If the sequence being determined is unknown, the nucleotides applied to a given colony are usually applied in a chosen order which is then repeated throughout the analysis, for example dATP, dTTP, dCTP, dGTP.

SBS techniques which can be used are described for example, but not limited to, those in U.S. Patent App. Pub. No. 2007/0166705, U.S. Patent App. Pub. No. 2006/0188901, U.S. Pat. No. 7,057,026, U.S. Patent App. Pub. No. 2006/0240439, U.S. Patent App. Pub. No. 2006/0281109, PCT Patent App. Pub. No. WO 05/065814, U.S. Patent App. Pub. No. 2005/0100900, PCT Patent App. Pub. No. WO 06/064199, PCT Patent App. Pub. No. WO07/010, 251, U.S. Patent App. Pub. No. 2012/0270305, U.S. Patent App. Pub. No. 2013/0260372, and U.S. Patent App. Pub. No. 2013/0079232, the entire contents of each of which are incorporated herein by reference.

In some embodiments, direct sequencing of a nucleic acid (DNA or RNA) is performed by sequential fluorescence hybridization (e.g., sequencing by hybridization). In some embodiments, a hybridization reaction is performed on the generated products described herein. In some embodiments, the generated products are not amplified prior to hybridization with a sequencing probe. In some embodiments, RNA is amplified prior to hybridization with sequencing probes (e.g., reverse transcription to cDNA and amplification of cDNA). In some embodiments, amplification is performed using single-molecule hybridization chain reaction. In some embodiments, amplification is performed using rolling chain amplification.

Sequential fluorescence hybridization can involve sequential hybridization of probes including degenerate primer sequences and a detectable label. A degenerate primer sequence is a short oligonucleotide sequence which is capable of hybridizing to any nucleic acid fragment independent of the sequence of said nucleic acid fragment. For example, such a method could include the steps of: (a) providing a mixture including four probes, each of which includes either A, C, G, or T at the 5'-terminus, further including degenerate nucleotide sequence of 5 to 11 nucleotides in length, and further including a functional domain (e.g., fluorescent molecule) that is distinct for probes with A, C, G, or T at the 5'-terminus; (b) associating the probes of step (a) to the target polynucleotide sequences, whose sequence needs will be determined by this method; (c) measuring the activities of the four functional domains and recording the relative spatial location of the activities; (d) removing the reagents from steps (a)-(b) from the target polynucleotide sequences; and repeating steps (a)-(d) for n cycles, until the nucleotide sequence of the spatial domain for each bead is determined, with modification that the oligonucleotides used in step (a) are complementary to part of the target polynucleotide sequences and the positions 1 through n flanking the part of the sequences. Because the barcode sequences are different, in some embodiments, these additional flanking sequences are degenerate sequences. The fluorescent signal from each spot on the array for cycles 1 through n can be used to determine the sequence of the target polynucleotide sequences.

In some embodiments, direct sequencing of nucleic acid (DNA or RNA) using sequential fluorescence hybridization is performed in vitro. In some embodiments, nucleic acid (DNA or RNA) is amplified prior to hybridization with a sequencing probe (e.g., reverse transcription to cDNA and amplification of cDNA). In some embodiments, a nucleic acid is exposed to the sequencing probe targeting coding regions of RNA. In some embodiments, one or more sequencing probes are targeted to each coding region. In some embodiments, the sequencing probe is designed to hybridize with sequencing reagents (e.g., a dye-labeled readout oligonucleotides). A sequencing probe can then hybridize with sequencing reagents. In some embodiments, output from the sequencing reaction is imaged. In some embodiments, a specific sequence of cDNA is resolved from an image of a sequencing reaction. In some embodiments, reverse transcription of a target RNA is performed prior to hybridization to the sequencing probe. In some embodiments, the sequencing probe is designed to target complementary sequences of the coding regions of RNA (e.g., targeting cDNA).

In some embodiments, a nucleic acid (DNA or RNA) is directly sequenced using a nanopore-based method. In some embodiments, direct sequencing is performed using nanopore direct sequencing in which the nucleic acid (DNA or RNA) is translocated through a nanopore. A nanopore current can be recorded and converted into a base sequence. In some embodiments, the nucleic acid (DNA or RNA)

remains attached to a substrate during nanopore sequencing. In some embodiments, the nucleic acid (DNA or RNA) is released from the substrate prior to nanopore sequencing. In some embodiments, where the analyte of interest is a protein, direct sequencing of the protein can be performed using nanopore-based methods. Examples of nanopore-based sequencing methods that can be used are described in Deamer et al., Trends Biotechnol. 18, 14 7-151 (2000); Deamer et al., Acc. Chem. Res. 35:817-825 (2002); Li et al., Nat. Mater. 2:611-615 (2003); Soni et al., Clin. Chem. 53, 1996-2001 (2007); Healy et al., Nanomed. 2, 459-481 (2007); Cockroft et al., J. Am. Chem. Soc. 130, 818-820 (2008); and in U.S. Pat. No. 7,001,792. The entire contents of each of the foregoing references are incorporated herein by reference.

In some embodiments, direct sequencing of a nucleic acid (DNA or RNA) is performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309: 1728-1732, and in U.S. Pat. Nos. 5,599,675; 5,750,341; 6,969,488; 6,172,218; and 6,306,597, the entire contents of each of which are incorporated herein by reference.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., Genome Research 14:870-877 (2004), the entire contents of each of which are incorporated herein by reference.

In some embodiments, commercial high-throughput digital sequencing techniques can be used to analyze barcode sequences, in which DNA templates are prepared for sequencing not one at a time, but in a bulk process, and where many sequences are read out preferably in parallel, or alternatively using an ultra-high throughput serial process that itself may be parallelized. Examples of such techniques include Illumina® sequencing (e.g., flow cell-based sequencing techniques), sequencing by synthesis using modified nucleotides (such as commercialized in TruSeq™ and HiSeq™ technology by Illumina, Inc., San Diego, Calif.), HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.), and sequencing of DNA nanoballs (Complete Genomics, Inc., Mountain View, Calif.).

In some embodiments, detection of a proton released upon incorporation of a nucleotide into an extension product can be used in the methods described herein. For example, the sequencing methods and systems described in U.S. Patent Application Publication Nos. 2009/0026082, 2009/0127589, 2010/0137143, and 2010/0282617, can be used to directly sequence barcodes.

In some embodiments, real-time monitoring of DNA polymerase activity can be used during sequencing. For example, nucleotide incorporations can be detected through fluorescence resonance energy transfer (FRET), as described for example in Levene et al., Science (2003), 299, 682-686, Lundquist et al., Opt. Lett. (2008), 33, 1026-1028, and Korlach et al., Proc. Natl. Acad. Sci. USA (2008), 105, 1176-1181. The entire contents of each of the foregoing references are incorporated herein by reference herein.

In some embodiments, the methods described herein can be used to assess analyte levels and/or expression in a cell or a biological sample over time (e.g., before or after treatment with an agent or different stages of differentiation). In some examples, the methods described herein can be performed on multiple similar biological samples or cells obtained from the subject at a different time points (e.g., before or after treatment with an agent, different stages of differentiation, different stages of disease progression, different ages of the subject, or before or after development of resistance to an agent).

In some embodiments, a lookup table (LUT) can be used to associate one property with another property of a feature. These properties include, e.g., locations, barcodes (e.g., nucleic acid barcode molecules), spatial barcodes, optical labels, molecular tags, and other properties.

In some embodiments, a lookup table can associate the plurality of nucleic acid barcode molecules with the features. In some embodiments, the optical label of a feature can permit associating the feature with the biological particle (e.g., cell or nuclei). The association of the feature with the biological particle can further permit associating a nucleic acid sequence of a nucleic acid molecule of the biological particle to one or more physical properties of the biological particle (e.g., a type of a cell or a location of the cell). For example, based on the relationship between the barcode and the optical label, the optical label can be used to determine the location of a feature, thus associating the location of the feature with the barcode sequence of the feature. Subsequent analysis (e.g., sequencing) can associate the barcode sequence and the analyte from the sample. Accordingly, based on the relationship between the location and the barcode sequence, the location of the biological analyte can be determined (e.g., in a specific type of cell, in a cell at a specific location of the biological sample).

In some embodiments, the feature can have a plurality of nucleic acid barcode molecules attached thereto. The plurality of nucleic acid barcode molecules can include barcode sequences. The plurality of nucleic acid molecules attached to a given feature can have the same barcode sequences, or two or more different barcode sequences. Different barcode sequences can be used to provide improved spatial location accuracy.

As discussed above, analytes obtained from a sample, such as RNA, DNA, peptides, lipids, and proteins, can be further processed. In particular, the contents of individual cells from the sample can be provided with unique spatial barcode sequences such that, upon characterization of the analytes, the analytes can be attributed as having been derived from the same cell. More generally, spatial barcodes can be used to attribute analytes to corresponding spatial locations in the sample. For example, hierarchical spatial positioning of multiple pluralities of spatial barcodes can be used to identify and characterize analytes over a particular spatial region of the sample. In some embodiments, the spatial region corresponds to a particular spatial region of interest previously identified, e.g., a particular structure of cytoarchitecture previously identified. In some embodiments, the spatial region corresponds to a small structure or group of cells that cannot be seen with the naked eye. In some embodiments, a unique molecular identifier can be used to identify and characterize analytes at a single cell level.

The analyte can include a nucleic acid molecule, which can be barcoded with a barcode sequence of a nucleic acid barcode molecule. In some embodiments, the barcoded analyte can be sequenced to obtain a nucleic acid sequence. In some embodiments, the nucleic acid sequence can include genetic information associate with the sample. The nucleic acid sequence can include the barcode sequence, or a complement thereof. The barcode sequence, or a complement thereof, of the nucleic acid sequence can be electronically associated with the property (e.g., color and/or intensity) of the analyte using the LUT to identify the associated feature in an array.

In some embodiments, the three-dimensional spatial profiling of one or more analytes present in a biological sample can be performed using a proximity capture reaction, which is a reaction that detects two analytes that are spatially close to each other and/or interacting with each other. For example, a proximity capture reaction can be used to detect sequences of DNA that are close in space to each other, e.g., the DNA sequences can be within the same chromosome, but separated by about 700 bp or less. As another example, a proximity capture reaction can be used to detect protein associations, e.g., two proteins that interact with each other. A proximity capture reaction can be performed in situ to detect two analytes that are spatially close to each other and/or interacting with each other inside a cell. Non-limiting examples of proximity capture reactions include DNA nanoscopy, DNA microscopy, and chromosome conformation capture methods. Chromosome conformation capture (3C) and derivative experimental procedures can be used to estimate the spatial proximity between different genomic elements. Non-limiting examples of chromatin capture methods include chromosome conformation capture (3-C), conformation capture-on-chip (4-C), 5-C, ChIA-PET, Hi-C, targeted chromatin capture (T2C). Examples of such methods are described, for example, in Miele et al., Methods Mol Biol. (2009), 464, Simonis et al., Nat. Genet. (2006), 38(11): 1348-54, Raab et al., Embo. J. (2012), 31(2): 330-350, and Eagen et al., Trends Biochem. Sci. (2018) 43(6): 469-478, the entire contents of each of which is incorporated herein by reference.

In some embodiments, the proximity capture reaction includes proximity ligation. In some embodiments, proximity ligation can include using antibodies with attached DNA strands that can participate in ligation, replication, and sequence decoding reactions. For example, a proximity ligation reaction can include oligonucleotides attached to pairs of antibodies that can be joined by ligation if the antibodies have been brought in proximity to each oligonucleotide, e.g., by binding the same target protein (complex), and the DNA ligation products that form are then used to template PCR amplification, as described for example in Soderberg et al., Methods. (2008), 45(3): 227-32, the entire contents of which are incorporated herein by reference. In some embodiments, proximity ligation can include chromosome conformation capture methods.

In some embodiments, the proximity capture reaction is performed on analytes within about 400 nm distance (e.g., about 300 nm, about 200 nm, about 150 nm, about 100 nm, about 50 nm, about 25 nm, about 10 nm, or about 5 nm) from each other. In general, proximity capture reactions can be reversible or irreversible.

The probes described herein may be used for analyzing a sequence of an extension product (e.g., RCA product) associated with a target nucleic acid or target analyte. In some embodiments, the sequence to be analyzed is a nucleic acid barcode sequence. For example, the nucleic acid barcode sequence may correspond to an analyte or a portion (e.g., a nucleic acid sequence) thereof or a labelling agent for the analyte or portion thereof in the biological sample.

In some embodiments, a method disclosed herein further comprises imaging the product comprising sequences of the spatial probes and a target nucleic acid or target analyte (e.g., or a product or derivative thereof), e.g., by optical imaging. In some embodiments, the imaging is performed prior to sequencing the product. For example, the one or more probes may be barcoded probes comprising one or more nucleic acid barcode sequences, which can be directly or indirectly bound by detectably-labeled detection probes (e.g., fluorescently labeled detection probes). A detectable signal or a series of signals such as fluorescence comprising a spatial pattern and/or a temporal pattern may be analyzed to reveal the presence/absence, distribution, location, amount, level, expression, or activity of the one or more analytes in the sample. In some embodiments, the one or more analytes (e.g., target sequences) are analyzed (e.g., by imaging) in situ in a tissue sample without migrating out of a cell of the tissue sample. In some embodiments, the one or more protein analytes are analyzed (e.g., by imaging) in situ in a tissue sample without migrating out of the tissue sample, e.g., onto a substrate.

In some cases, the analysis is performed on one or more images captured, and may comprise processing the image(s) and/or quantifying signals observed. For example, the analysis may comprise processing information of one or more cell types, one or more types of biomarkers, a number or level of a biomarker, and/or a number or level of cells detected in a particular region of the sample. In some embodiments, the analysis comprises detecting a sequence e.g., a barcode present in the sample. In some embodiments, the analysis includes quantification of puncta (e.g., if amplification products are detected). In some cases, the analysis includes determining whether particular cells and/or signals are present that correlate with one or more biomarkers from a particular panel. In some embodiments, the obtained information may be compared to a positive and negative control, or to a threshold of a feature to determine if the sample exhibits a certain feature or phenotype. In some cases, the information may comprise signals from a cell, a region, and/or comprise readouts from multiple detectable labels. In some case, the analysis further includes displaying the information from the analysis or detection step. In some embodiments, software may be used to automate the processing, analysis, and/or display of data.

IV. COMPOSITIONS AND KITS

In some embodiments, provided herein is a composition comprising a probe or library of spatial probes (e.g., X spatial probes, Y spatial probes, and/or Z spatial probes) as described in Section III. In some embodiments, the library of spatial probes comprises one or more population of spatial probes that can be separated and distributed in the biological sample based on properties of the migration domain of each spatial probe. In some embodiments, each population comprises a variety of spatial probes comprising different migration domains. In some embodiments, provided herein is a product of one or more spatial probes comprising a sequence corresponding to the migration domain(s) of the one or more spatial probes and a sequence corresponding to the target molecule. In some embodiments, the product is an extension product of one or more spatial probes. In some embodiments, the product is a ligation product of one or more spatial probes (e.g., a ligated X, Y, and Z probe complex, optionally further comprising a ligated intermediate probe). In some embodiments, the product is an extension product of a ligated X, Y and Z probe complex.

Also provided herein are kits, for example comprising a probe or a library of spatial probes (e.g., X spatial probes, Y spatial probes, and/or Z spatial probes) as described in Section III.

In some embodiments, provided herein is a kit, comprising: (1) a plurality of X spatial probes each comprising (i) an X targeting sequence for targeting a target nucleic acid molecule, (ii) an X migration domain (e.g., variable-length sequence), and optionally (iii) an X migration barcode (e.g., length barcode) corresponding to the X migration domain (variable-length sequence; (2) a plurality of Y spatial probes each comprising (i) a Y targeting sequence for targeting a target nucleic acid molecule and/or an X spatial probe, (ii) a Y migration domain (e.g., variable-length sequence), and optionally (iii) a Y migration barcode (e.g., length-barcode) sequence corresponding to the Y migration domain (e.g., variable-length sequence); and (3) a plurality of Z spatial probes each comprising (i) a Z targeting sequence for targeting a target nucleic acid molecule, an X spatial probe, and/or a Y spatial probe, (ii) a Z migration domain (e.g., variable-length sequence), and optionally (iii) a Z migration barcode (e.g., length-barcode) sequence corresponding to the Z variable-length sequence.

In some embodiments, the X, Y, and Z spatial probes are configured to distribute by size in the direction of electrophoresis (e.g., in the x-, y-, or z-direction, respectively) such that the migration barcode sequence of a spatial probe corresponds to the location of the spatial probe relative to other spatial probes of the same dimension in the direction of electrophoresis.

In some embodiments, spatial probes of the first plurality (X spatial probes) or a subset thereof can share a barcode sequence corresponding to the first population or subset thereof. In some embodiments, spatial probes of the second plurality (Y probes) or a subset thereof can share a barcode sequence corresponding to the second population or subset thereof. In some embodiments, spatial probes of the third plurality (Z probes) or a subset thereof can share a barcode sequence corresponding to the third population or subset thereof. In some embodiments, the first, second, and/or third pluralities (X, Y, and Z probes) can comprise spatial probes targeting different target molecules.

In some embodiments, the kit further comprises one or more intermediate probes capable of directly or indirectly binding (e.g., hybridizing) to the target molecule, wherein the intermediate probe(s) comprise(s) one or more adapter sequences complementary to a targeting domain of the spatial probes. In some embodiments, the adapter sequences can be common among intermediate probes designed to specifically hybridize to different target molecules.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and/or buffers for chemical or enzymatic ligation and/or amplification, such as click chemistry reagents, ligases and/or polymerases. In some aspects, the kit can also comprise any of the reagents described herein, e.g., wash buffer and ligation buffer. In some embodiments, the kits contain reagents for detection and/or sequencing, such as barcode detection probes or detectable labels. In some embodiments, the kits optionally contain other components, for example nucleic acid primers, enzymes and reagents, buffers, nucleotides, modified nucleotides, reagents for additional assays.

V. TERMINOLOGY

Herein, "automatically" means with little or no direct human control.

Herein, "barcode nucleotide sequence" refers to a nucleotide sequence that is associated with or linked to a property of a molecule containing the barcode nucleotide sequence. Herein, one type of barcode nucleotide sequence may be uniquely associated with length of the oligonucleotide. This barcode nucleotide sequence may be called a migration barcode (e.g., length barcode) sequence or a spatial barcode. Herein, another type of barcode nucleotide sequence may be uniquely associated with another sequence within the oligonucleotide, a hybridizing nucleotide sequence, in some examples. This barcode nucleotide sequence may be called a hybridizing barcode sequence. Barcode sequences that are associated with or linked to a property of an oligonucleotide, a targeting domain (e.g., hybridizing sequence) for example, may be sequences that are not comprised in the targeting domain (e.g., hybridizing sequence) or may be sequences comprised in the hybridizing sequence. That is, a barcode sequence may be separate from, for example, the targeting domain (e.g., hybridizing sequence) or may be part of the targeting domain (e.g., hybridizing sequence). In some examples, a sequence within an oligonucleotide may be used as a barcode nucleotide sequence if that sequence is associated with a property of the oligonucleotide or properties of a population of oligonucleotides.

Herein, "capturing" means to identify a target nucleic acid molecules (e.g., an RNA), generally by hybridization using a nucleic acid probe for the target nucleic acid molecule (e.g., RNA) and/or amplification of a target nucleic acid molecule or a nucleic acid probe hybridized to it (e.g., an RNA or a probe hybridized to the RNA) using, for example polymerase chain reactions (PCR) and/or nucleic acid extension of a target nucleic acid molecule or a nucleic acid probe hybridized to it (e.g., an RNA or a probe hybridized to the RNA) using, for example, reverse transcription reactions.

Herein, "cellular RNA" refers to RNA molecules encoded by genes of a cell.

Herein, "conductive" means capable of transporting an electric charge.

Herein, "crosslinking" means connecting or attaching two or more separate substances to each other. Herein, crosslinking is used to describe one or both of the acts of connecting or attaching nucleic acids in a hydrogel to the hydrogel, or connecting or attaching separate nucleic acid molecules in a hydrogel to one another, both for the purpose of preventing migration of the nucleic acid molecules in the hydrogel when an electric field is applied across the hydrogel.

Herein, "dimension" means a measurement of length in one direction. For example, a three-dimensional space (e.g., a cube) has three dimensions: width, height and depth. Dimensions in three-dimensional space, like in a cube, may be referred to as x-, y- and z-dimensions. Note that when oligonucleotides are herein stated to have been distributed throughout a three-dimensional space or medium, there may or may not have been separate migrations of oligonucleotides through the x-, y- and z-dimensions of the medium to obtain that distribution. In other words, there may be various approaches or techniques to disperse or distribute oligonucleotides throughout the entirety of a three-dimensional space.

Herein, "embed" means to surround and implant in a mass.

Herein, "hybridize" refers to a nucleotide sequence of single-stranded nucleic acid molecule forming a complex with a nucleic acid molecule having a complementary nucleotide sequence. Generally, the complex forms through hydrogen bonding between complementary nucleotide bases in separate nucleic acid molecules.

Herein, "hybridizing nucleotide sequence" refers to a nucleotide sequence, within an oligonucleotide for example, that is capable of hybridizing with a complementary nucleotide sequence in a target nucleic acid molecule present on or within a cell from a tissue sample (e.g., cellular RNA). When a hybridizing nucleotide sequence is of such a length that it hybridizes with a complementary nucleotide sequence that is unique to target nucleic acid molecule(s) (e.g., cellular RNA or family of RNAs), the hybridizing nucleotide sequence may be said to hybridize to the same target nucleic acid molecule (e.g., the same RNA).

Herein, "identifying," when referring to a nucleotide sequence capable of identifying a target nucleic acid molecule (e.g., an RNA), means that the nucleotide sequence can hybridize to a complementary nucleotide sequence in the identified target nucleic acid molecule (e.g., the identified RNA), in a molecule that can hybridize to the target nucleic acid molecule (e.g., the RNA), or in a molecule synthesized using the target nucleic acid molecule (e.g., the RNA), or the molecule that can hybridize to the target nucleic acid molecule (e.g., a probe that can hybridize to the RNA), as template.

Herein, "immobilize," when referring to immobilizing oligonucleotides in a medium, means that the oligonucleotides are prevented from moving in the medium.

Herein, "length," when referring to an oligonucleotide, means linear length as defined by the number of nucleotides in the oligonucleotide.

Herein, "ligation" means to join molecules containing nucleotide sequences, generally using an enzyme.

Herein, "linked to" refers to association or correlation of one nucleotide sequence within an oligonucleotide (e.g., a barcode nucleotide sequence) with another property or sequence of the oligonucleotide (e.g., length of the oligonucleotide or sequence of hybridizing sequence).

Herein, "medium" refers to a substance through which a population of oligonucleotides can be migrated to separate the oligonucleotides based on size. In some examples herein, the medium includes conductive hydrogels.

Herein, "migrate," when referring to migrating oligonucleotides through a medium, means causing oligonucleotides to move through the medium. Generally, herein, oligonucleotides move through a medium (e.g., hydrogel) because an electric field is applied across the medium.

Herein, a "nucleic acid product" refers to a nucleic acid produced using a target nucleic acid molecule (e.g., an RNA) as a template, and derivatives thereof. In some examples, nucleic acid probe (e.g., an RNA capturing probe) may act as a primer for a nucleic acid extension reaction (e.g., a reverse transcription reaction or a polymerase chain reaction) that extends (or amplifies) a nucleotide sequence of the target nucleic acid molecule, thus generating nucleic acid products based on the target nucleic acid molecule or the nucleic acid probe.

Herein, "nucleotide sequence" refers to a linear progression of nucleotide bases within a nucleic acid molecule (e.g., oligonucleotide).

Herein, "oligonucleotide" means a linear polymer of nucleotides, in some examples 2'-deoxyribonucleotides. Oligonucleotides are single stranded. Oligonucleotides can be of various lengths.

Herein, "polymer" refers to a molecule made of repeated units.

Herein, "population," when referring to oligonucleotides, means more than one oligonucleotide. In some examples, a population of oligonucleotides may be between 10 and $10^{10}$ oligonucleotides. A population of oligonucleotides of different lengths means that at least some of the oligonucleotides in the population are not of the same length.

Herein, "regimented" refers to differences in length of oligonucleotides within a population of oligonucleotides. A population of oligonucleotides having regimented lengths means that oligonucleotides in the population differ in length by multiples of a specified number of nucleotides. For example, a population of five oligonucleotides having lengths of 100, 105, 110, 115 and 120 nucleotides could be said to have a regimented length of 5 nucleotides.

Herein, "RNA capturing probe" refers to a nucleic acid molecule capable of hybridizing to an RNA.

Herein, "RNA-derived amplification product" refers to a nucleic acid produced using an RNA as template, and derivatives thereof. In some examples, an RNA capturing probe may act as a primer for a polymerase chain reaction that amplifies a nucleotide sequence of the RNA, thus producing amplification products derived from the RNA.

Herein, "sequence-specific amplification" describes amplification of a nucleic acid template to which a primer has hybridized. The amplification product contains a nucleotide sequence complementary to the template.

Herein, "tissue sample" means an aggregate of cells from a tissue or organ.

Herein, "variable-length nucleotide sequence," refers to a region of an oligonucleotide that contains nucleotide sequences responsible for different lengths of oligonucleotides in a population of oligonucleotides of different lengths.

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more." It should also be understood that, unless a term is expressly defined in this disclosure using the sentence "As used herein, the term '_____', refers to . . . " or a similar sentence, there is no intent to limit the meaning of that term, either expressly or by implication, beyond its plain or ordinary meaning, and such term should not be interpreted to be limited in scope based on any statement made in any section of this disclosure (other than the language of the claims). To the extent that any term recited in the claims is referred to in this disclosure in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

The term "about" or "approximately" as used herein refers to the usual error range for the respective value readily known to the skilled person in this technical field. Reference to "about" a value or parameter herein includes (and describes) embodiments that are directed to that value or parameter per se. For example, "about" can mean within 1 or more than 1 standard deviation, per the practice in the relevant field. Alternatively, "about" can mean a range of up to 20%, up to 10%, up to 5%, or up to 1% of a given value.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample, a bead, and/or a probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others.

Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vi) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(vii) Primer Extension

A "primer extension" refers to any method where two nucleic acid sequences become linked (e.g., hybridized) by an overlap of their respective terminal complementary nucleic acid sequences. Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(viii) Ligation

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. In some embodiments, ligations are carried out enzymatically to form a phosphodiester linkage between a 5' carbon terminal nucleotide of one oligonucleotide with a 3' carbon of another nucleotide. In some embodiments, ligations are carried out chemically (e.g., using click chemistry).

(ix) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(x) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: E. coli DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, Thermococcus sp. (strain 9oN) DNA ligase (9oN™ DNA ligase, available from New England Biolabs, Ipswich, Mass.), and Ampligase™ (available from Epicentre Biotechnologies, Madison, Wis.). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™ ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™ ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a probe for in situ assay, a capture probe or analyte. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a capture probe associated with a feature. For example, detectably labeled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, capture probe, or composition to be detected. For example, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18 (5)), DIDS, Dil (DilC18(3)), DiO (DiOC18(3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, *Lucifer* Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, Mito Tracker® Green, Mito Tracker® Orange, Mito Tracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

(xii) Subject

As used herein, the term "subject", generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

VI. EXEMPLARY EMBODIMENTS

Among the provided embodiments are:

Embodiment 1. An oligonucleotide comprising a first barcode nucleotide sequence that is linked to length of the oligonucleotide.

Embodiment 2. The oligonucleotide of Embodiment 1, comprising a nucleotide sequence capable of hybridizing to a cellular ribonucleic acid (RNA), a cellular RNA capturing probe, or a cellular RNA-derived amplification product.

Embodiment 3. The oligonucleotide of Embodiment 2, comprising a second barcode nucleotide sequence linked to the nucleotide sequence capable of hybridizing to a cellular RNA, a cellular RNA capturing probe, or a cellular RNA-derived amplification product.

Embodiment 4. A population of oligonucleotides of any one of Embodiments 1-3 having different lengths.

Embodiment 5. A population of oligonucleotides of any one of Embodiments 1-3 having different regimented lengths.

Embodiment 6. The population of oligonucleotides of Embodiment 4 or 5, where the oligonucleotides of the population comprise the same nucleotide sequence capable of hybridizing to a cellular RNA, a cellular RNA capturing probe, or a cellular RNA-derived amplification product.

Embodiment 7. A population of oligonucleotides of different lengths, where oligonucleotides in the population comprise a first barcode nucleotide sequence linked to length of the oligonucleotides.

Embodiment 8. The population of oligonucleotides of Embodiment 7, where oligonucleotides in the population differ in length by regimented lengths.

Embodiment 9. The population of oligonucleotides of Embodiment 7 or 8, where oligonucleotides in the population comprise a hybridizing nucleotide sequence capable of identifying the same cellular RNA.

Embodiment 10. The population of oligonucleotides of Embodiment 9, where the same cellular RNA is encoded by a common gene.

Embodiment 11. The population of oligonucleotides of Embodiments 9 or 10, where the oligonucleotides in the population comprise a second barcode nucleotide sequence linked to the hybridizing nucleotide sequence capable of identifying the same cellular RNA.

Embodiment 12. The population of oligonucleotides of any one of Embodiments 7-11, where oligonucleotides in the population comprise a nucleotide sequence capable of hybridizing to an RNA, an RNA capturing probe, or an RNA-derived amplification product; and where the RNA, an RNA to which the RNA capturing probe hybridizes, and an RNA from which the amplification product is derived, are the same RNA.

Embodiment 13. The population of oligonucleotides of Embodiment 12, where the oligonucleotides in the population comprise a second barcode nucleotide sequence linked to the nucleotide sequence capable of hybridizing to the RNA, the RNA capturing probe, or the RNA-derived amplification product.

Embodiment 14. The population of oligonucleotides of one of Embodiments 11 or 13, where the oligonucleotides in the population comprise a third barcode nucleotide sequence common to the oligonucleotides in the population.

Embodiment 15. A composition, comprising: two or more different populations of oligonucleotides of Embodiments 11 or 13, where the different populations of oligonucleotides comprise i) hybridizing nucleotide sequences capable of identifying different RNAs, or ii) nucleotide sequences capable of hybridizing to RNA, RNA capturing probes, or the RNA-derived amplification products that are different.

Embodiment 16. The composition of Embodiment 15, where oligonucleotides of the different populations comprise a third barcode nucleotide sequence common to the oligonucleotides.

Embodiment 17. A population of oligonucleotides, comprising: oligonucleotides of different lengths encoding the same hybridizing nucleotide sequence; and where the oligonucleotides comprise a first barcode nucleotide sequence linked to oligonucleotide length.

Embodiment 18. The population of oligonucleotides of Embodiment 17, where the oligonucleotides comprise the same second barcode nucleotide sequence that is linked to the hybridizing sequence.

Embodiment 19. The population of oligonucleotides of Embodiment 17 or 18, where a length of the first and/or second barcode nucleotide sequence is 4, 5, 6, 7, 9, 10, 11, 12, 13, 14, 15, 16, 17, 18, 19, 20, 21, 22, 23, 24 or 25 nucleotides.

Embodiment 20. The population of oligonucleotides of any one of Embodiments 17-19, where the oligonucleotides in the population range in length from 10 to 106 nucleotides.

Embodiment 21. The population of oligonucleotides of any one of Embodiments 17-19, where length between a shortest and a longest oligonucleotide in the population is about 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000 or 50,000 nucleotides.

Embodiment 22. The population of oligonucleotides of any one of Embodiments 17-19, where the oligonucleotides in the population have regimented lengths of between 1 and 100 nucleotides, 100 and 1000 nucleotides or 1000 and 10,000 nucleotides.

Embodiment 23. The population of oligonucleotides of Embodiment 18, where a total length of the hybridizing nucleotide sequence, first barcode nucleotide sequence, and second barcode nucleotide sequence is the same in oligonucleotides in the population; and where the oligonucleotides in the population additionally comprise one or more variable length nucleotide sequences between 2 and 10,000 nucleotides in length.

Embodiment 24. The population of oligonucleotides of Embodiment 23, where the variable length sequences comprise a 5' end or a 3' end of the oligonucleotides in the population.

Embodiment 25. The population of oligonucleotides of any one of Embodiments 18, 23 and 24 where the oligonucleotides comprise a third barcode nucleotide sequence common to the oligonucleotides in the population.

Embodiment 26. A composition, comprising at least two populations of oligonucleotides of one of Embodiments 18 or 25; where separate populations comprise different hybridizing nucleotide sequences capable of identifying different RNAs; and where the second barcode nucleotide sequence of separate oligonucleotide populations is different.

Embodiment 27. The composition of Embodiment 26, comprising at least 10, 50, 100, 150, 200, 250, 300, 350, 400, 450, 500, 600, 700, 800, 900, 1,000, 2,000, 3,000, 4,000, 5,000, 6,000, 7,000, 8,000, 9,000, 10,000, 15,000, 20,000, 25,000 or 30,000 separate populations of oligonucleotides.

Embodiment 28. The composition of one of Embodiments 26 or 27, where the oligonucleotides of the composition comprise a common third barcode nucleotide sequence.

Embodiment 29. A population of oligonucleotides, the oligonucleotides in the population comprising different lengths and including: an identical hybridizing nucleotide sequence; and a first barcode nucleotide sequence linked to individual oligonucleotide length.

Embodiment 30. The population of oligonucleotides of Embodiment 29, the oligonucleotides of the population additionally including: a second barcode nucleotide sequence linked to the hybridizing nucleotide sequence.

Embodiment 31. The population of oligonucleotides of one of Embodiments 29 or 30, where different lengths of the oligonucleotides in the population are due to variable-length nucleotide sequences at a 5' end or 3' end of the oligonucleotides.

Embodiment 32. A population of oligonucleotides of different lengths, oligonucleotides in the population comprising: a first sequence of nucleotides, variable in length, providing for the different lengths of oligonucleotides in the population; a second sequence of nucleotides, fixed in length, correlating with length of the first sequence of nucleotides; and a third sequence of nucleotides, identical between oligonucleotides in the population and capable of identifying the same RNA or amplification product thereof.

Embodiment 33. The population of oligonucleotides of Embodiment 32, comprising: a fourth sequence of oligonucleotides, fixed in length, and linked to the third sequence of nucleotides.

Embodiment 34. A method, comprising: migrating a first population of oligonucleotides of any one of Embodiments 7-14, or a first composition of any one of Embodiments 15-16, through a three-dimensional medium in a first dimension to separate individual oligonucleotides in the first population by size and immobilizing the separated oligonucleotides of the first population in the medium.

Embodiment 35. The method of Embodiment 34, comprising: migrating a second population of oligonucleotides of any one of Embodiments 7-14, or a second composition of any one of Embodiments 15-16, through the three-dimensional medium in a second dimension to separate individual oligonucleotides in the second population by size and immobilizing the separated oligonucleotides of the second population in the medium.

Embodiment 36. The method of Embodiment 35, comprising: migrating a third population of oligonucleotides of any one of Embodiments 7-14, or a third composition of any one of Embodiments 15-16, through the three-dimensional medium in a third dimension to separate individual oligonucleotides in the third population by size and immobilizing the separated oligonucleotides of the third population in the medium.

Embodiment 37. The method of Embodiment 36, where individual oligonucleotides of the first, second and third populations comprise a barcode nucleotide sequence common to oligonucleotides of each population.

Embodiment 38. The method of one of Embodiments 36 or 37, comprising: analyzing the three-dimensional medium to determine relative locations of the oligonucleotides of the three populations.

Embodiment 39. A method for separating oligonucleotides, comprising: migrating a first population of oligonucleotides in a first dimension through a medium to separate the oligonucleotides of the first population; and immobilizing the oligonucleotides of the first population in the medium.

Embodiment 40. The method of Embodiment 39, comprising: migrating a second population of oligonucleotides in a second dimension through the medium to separate the oligonucleotides of the second population; and immobilizing the oligonucleotides of the second population in the medium.

Embodiment 41. The method of Embodiment 40, comprising: migrating a third population of oligonucleotides in a third dimension through the medium to separate the oligonucleotides of the third population; and immobilizing the oligonucleotides of the third population in the medium.

Embodiment 42. The method of any one of Embodiments 39, 40 or 41, where the oligonucleotides in the populations are not all the same length.

Embodiment 43. The method of any one of Embodiments 39-42, where the oligonucleotides in the populations are separated based on size or length by migration through the medium.

Embodiment 44. The method of any one of Embodiments 39-43, where the medium includes a hydrogel.

Embodiment 45. The method of any one of Embodiments 39-44, where an electric field is applied across the medium to migrate the oligonucleotides through the medium.

Embodiment 46. The method of any one of Embodiments 39-45, where the medium contains cellular RNAs.

Embodiment 47. The method of Embodiment 46, where the oligonucleotides of the first, second and third populations comprise a hybridizing nucleotide sequence capable of identifying the same cellular RNA.

Embodiment 48. The method of any one of Embodiments 39-47, comprising: prior to the migrating and the immobilizing of the first population of oligonucleotides, capturing cellular RNAs in the medium using RNA capturing probes and/or production of RNA-derived amplification products.

Embodiment 49. The method of any one of Embodiments 48, comprising: subjecting the medium containing the separated oligonucleotides to conditions where the hybridizing nucleotide sequence of the separated oligonucleotides hybridizes to the captured cellular RNAs, RNA capturing probes and/or RNA-derived amplification products present in the medium that have a nucleotide sequence complementary to the hybridizing nucleotide sequence of the oligonucleotides.

Embodiment 50. The method of Embodiment 49, comprising: determining nucleotide sequences from oligonucleotides that have hybridized to captured cellular RNAs, RNA capturing probes and/or RNA-derived amplification products, to ascertain location of cellular RNAs in the medium that have nucleotide sequences complementary to the hybridizing nucleotide sequence of the oligonucleotides.

Embodiment 51. A method for separating oligonucleotides, comprising: electrophoresing a population of oligonucleotides of any one of Embodiments 7-14 through one or more dimensions of a three-dimensional conductive polymer to separate the oligonucleotides; and after electrophoresis in each dimension, immobilizing the separated oligonucleotides within the conductive polymer.

Embodiment 52. A method, comprising: capturing cellular RNAs in a three-dimensional tissue sample using RNA capturing probes and/or sequence-specific amplification of the cellular RNAs; embedding the tissue sample in a conductive polymer; electrophoresing a first composition of one of Embodiments 15 or 16 through a first dimension of the conductive polymer to separate individual oligonucleotides of the first composition by size, and immobilizing the separated oligonucleotides of the first composition in the polymer; electrophoresing a second composition of one of Embodiments 14-15 through a second dimension of the conductive polymer to separate individual oligonucleotides of the second composition by size, and immobilizing the separated oligonucleotides of the second composition in the polymer; electrophoresing a third composition of one of Embodiments 14-15 through a third dimension of the conductive polymer to separate individual oligonucleotides of the third composition by size, and immobilizing the separated oligonucleotides of the third composition in the polymer; subjecting the conductive polymer to conditions providing for hybridization of oligonucleotides in the polymer to the captured RNAs, RNA capturing probes and/or RNA-derived amplification products; nucleotide sequencing of the hybridized oligonucleotides and captured RNAs, RNA capturing probes and/or RNA-derived amplification products; and integrating sizes of the sequenced oligonucleotides with identity of the captured cellular RNAs to determine relative location of the cellular RNAs in the three-dimensions of the polymer.

Embodiment 53. The method of Embodiment 52, where immobilizing includes at least one of: (i) chemical and/or enzymatic crosslinking of oligonucleotides to the conductive polymer, (ii) chemical and/or enzymatic crosslinking of oligonucleotides to substances in the conductive polymer, (iii) chemical and/or enzymatic crosslinking of oligonucleotides to other oligonucleotides or nucleotide molecules, (iv) linking of oligonucleotides to substances added to the conductive polymer, (v) ligation of oligonucleotides to other oligonucleotides or nucleotide molecules, or (vi) hybridization of oligonucleotides to other oligonucleotides or nucleotide molecules.

Embodiment 54. An electrophoresis apparatus, comprising: a main chamber that can accommodate a three-dimensional tissue sample; oligonucleotide chambers positioned on one side of, and in communication with, the chamber in each of an x-, y- and z-dimensions of the chamber; and electrodes positioned at each end of the main chamber in each of its x-, y- and z-dimensions and configured to direct separate electric fields across a length of each dimension.

Embodiment 55. An apparatus for electrophoresis, comprising: a central chamber enclosing a volume configured to accept a tissue sample, the chamber additionally configured to hold a volume of electrophoresis buffer into which the tissue sample is submerged; three oligonucleotide sample chambers, one positioned adjacent to and contiguous with one side of the central chamber in each of its x-, y- and z-dimensions, the oligonucleotide sample chambers configured to hold an oligonucleotide sample solution that can be migrated into the entire area of, and across the length, of each dimension of the central chamber; and electrodes positioned to separately and sequentially direct an electric field across each of the x-, y- and z-dimensions of the central chamber to migrate the oligonucleotides in the sample solution from the oligonucleotide sample chambers into and through the dimensions of the central chamber containing the tissue sample.

Embodiment 56. The apparatus of Embodiment 55, where the central chamber is configured to accept a volume of liquid hydrogel solution to embed the tissue sample in the hydrogel after the hydrogel solution polymerizes.

Embodiment 57. The apparatus of Embodiment 55, where the apparatus can be repositioned so that sequential electrophoresis of a sample in each of an x-, y- and z-dimension is performed vertically.

Embodiment 58. An electrophoresis apparatus, comprising: a means for separately electrophoresing nucleic acids across the area, and through the length, of each of an x-, y- and z-dimension of a three-dimensional space.

Embodiment 59. A system comprising the apparatus of any one of Embodiments 54, 55 and 58, where the system is configured to automatically perform one or more of: (i) load a tissue sample into a chamber; (ii) embed a tissue sample in a polymer; (iii) load a sample of oligonucleotides into a chamber of the device; (iv) electrophorese the oligonucleotides in the sample to distribute the oligonucleotides throughout the polymer; (v) subject the polymer containing the distributed oligonucleotides to conditions favorable for hybridization of the oligonucleotides to complementary sequences in the polymer, (vi) depolymerize or dissolve the polymer to release the oligonucleotides; and (vii) determine a nucleotide sequence of oligonucleotides released from the polymer.

Embodiment 60. A method, comprising migrating populations of oligonucleotides of different lengths through a three-dimensional medium to separate the oligonucleotides and disperse the oligonucleotides throughout the three-dimensional space.

Embodiment 61. The method of Embodiment 60, wherein migrating the populations of oligonucleotides through the medium includes electrophoresis.

Embodiment 62. A method, comprising: submerging a tissue sample in a solution capable of forming a polymer; polymerizing the solution to form a polymer; migrating a population of oligonucleotides of different lengths through the polymer to distribute the oligonucleotides throughout the polymer; subjecting the polymer to conditions conducive for hybridization of the distributed oligonucleotides to RNA from cells in the tissue sample; depolymerizing or dissolving the polymer to release oligonucleotides hybridized to the RNA; and determining a nucleotide sequence of the released oligonucleotides.

Embodiment 63. The method of Embodiment 62, where the polymer is a conductive polymer.

Embodiment 64. The method of Embodiment 63, where the conductive polymer includes a hydrogel.

Embodiment 65. The method of Embodiment 62, where the population of oligonucleotides is migrated through the polymer by electrophoresis.

Embodiment 66. The method of Embodiment 65, where the electrophoresis is performed in multiple dimensions.

Embodiment 67. A three-dimensional medium, comprising oligonucleotides dispersed throughout the volume of the three-dimensional medium.

Embodiment 68. The three-dimensional medium of Embodiment 67, where the oligonucleotides are oligonucleotides from any one of Embodiments 1-3, are populations of oligonucleotides from any one of Embodiments 4-14, 17-25 or 29-33, or are compositions from any one of Embodiments 15-16 or 26-28.

Embodiment 69. The oligonucleotide of Embodiment 1, comprising a nucleotide sequence capable of hybridizing to a reporter oligonucleotide, wherein the reporter oligonucleotide is conjugated to a cell labelling agent.

Embodiment 70. The oligonucleotide of Embodiment 69, wherein the cell labeling agent is selected from the group consisting of a protein binding agent, a lipophilic moiety, a nanoparticle, a cell-penetrating peptide, a peptide-based chemical vector, a dye, and a fluorophore.

Embodiment 71. The oligonucleotide of Embodiment 70, wherein the protein binding agent is an antibody.

Embodiment 72. The oligonucleotide of Embodiment 1, comprising a nucleotide sequence capable of hybridizing to a nucleic acid molecule corresponding to a cellular analyte or a derivative thereof.

Embodiment 73. The oligonucleotide of Embodiment 72, wherein the cellular analyte is RNA or deoxy-ribonucleic acid (DNA).

Embodiment 74. The population of oligonucleotides of Embodiment 7, wherein oligonucleotides in the population comprise nucleotide sequences capable of hybridizing to reporter oligonucleotides, wherein the reporter oligonucleotides are conjugated to cell labelling agents.

Embodiment 75. The population of oligonucleotides of Embodiment 74, wherein the cell labeling agents are selected from the group consisting of protein binding agents, lipophilic moieties, nanoparticles, cell-penetrating peptides, peptide-based chemical vectors, dyes, and fluorophores.

Embodiment 76. The population of oligonucleotides of Embodiment 75, wherein the protein binding agents are antibodies.

Embodiment 77. The population of oligonucleotides of Embodiment 7, wherein oligonucleotides in the population comprise nucleotide sequences capable of hybridizing to nucleic acid molecules corresponding to cellular analytes or derivatives thereof.

Embodiment 78. The population of oligonucleotides of Embodiment 77, wherein the cellular analytes are RNA or deoxy-ribonucleic acid (DNA).

Embodiment 79. A method, comprising: migrating a first oligonucleotide of any one of Embodiments 69-73, or a first population of oligonucleotides of any one of Embodiments 74-78, through a three-dimensional medium in a first dimension to separate the first oligonucleotide or individual oligonucleotides of the first population by size and immobilizing the separated first oligonucleotide or separated oligonucleotides of the first population in the medium.

Embodiment 80. The method of Embodiment 79, comprising: migrating a second oligonucleotide of any one of Embodiments 69-73, or a second population of oligonucleotides of any one of Embodiments 74-78, through the three-dimensional medium in a second dimension to separate the second oligonucleotide or individual oligonucleotides of the second population by size and immobilizing the separated second oligonucleotide or separated oligonucleotides of the second population in the medium.

Embodiment 81. The method of Embodiment 80, comprising: migrating a third oligonucleotide of any one of Embodiments 69-73, or a third population of oligonucleotides of any one of Embodiments 74-78, through the three-dimensional medium in a third dimension to separate the third oligonucleotide or individual oligonucleotides of the third population by size and immobilizing the separated third oligonucleotide or separated oligonucleotides of the third population in the medium.

EXAMPLE

The following example is included for illustrative purposes only and is not intended to limit the scope of the present disclosure.

The present example describes an exemplary workflow for analyzing a biological sample according to the methods provided herein. In an example, a tissue sample is prepared (e.g., according to standard fixation and permeabilization protocols). After the tissue sample is prepared, a set of probes (e.g., circular or circularized probes) are contacted with the sample that encounter and hybridize to endogenous analytes (e.g., intracellular mRNAs) within the intact tissue. The hybridized probes are enzymatically replicated as cDNA amplicons. In an example, the amplicons are constructed in situ with an acrylic acid N-hydroxysuccinimide moiety modification and then copolymerized with acrylamide to embed within a matrix (e.g., a hydrogel matrix), followed by clearance of unbound lipids and proteins.

In some examples, the amplicon (a product of an endogenous analyte) is the target molecule, and corresponds to the location of an intracellular mRNA. In other examples, the target molecule is the mRNA itself. In some examples the amplicon is immobilized in the matrix (e.g., the amplicons constructed with an acrylic acid N-hydroxysuccinimide moiety modification can be copolymerized with the matrix). In some embodiments, the mRNA is immobilized in the matrix, e.g. by crosslinking or by hybridization to an acrydite-modified poly-dT probe.

Spatial probes can be migrated into the biological sample by electrophoresis. Briefly, the method can comprise: (a) in a first dimension, migrating a first population of spatial probes into the biological sample, wherein a first-dimension spatial probe of the first population is targeted to a target molecule immobilized in the biological sample; (b) in a second dimension, migrating a second population of spatial probes into the biological sample, wherein a second-dimension spatial probe of the second population is targeted to the target molecule and/or the first-dimension spatial probe targeted thereto; (c) in a third dimension, migrating a third population of spatial probes into the biological sample, wherein a third-dimension spatial probe of the third population is targeted to the target molecule, the first-dimension spatial probe targeted thereto, and/or the second-dimension spatial probe targeted thereto, wherein the first-dimension spatial probe, the second-dimension spatial probe, and the third-dimension spatial probe each comprises: (i) a targeting domain, (ii) a migration domain corresponding to a location in the biological sample to which the spatial probe is migrated in the respective dimension, and optionally (iii) a migration barcode sequence corresponding to the migration domain. An exemplary device for migrating probes in a first dimension, a second dimension, and a third dimension is illustrated in FIG. 9.

In an example, the first population of spatial probes can be immobilized in the sample before migrating in the second population of spatial probes, and the second population of spatial probes can be immobilized before migrating in the third population of spatial probes.

Next, a product can be generated in the biological sample, the product comprising: (1) a sequence or complement thereof of the migration domains and/or the migration barcode sequences of the first-dimension spatial probe, the second-dimension spatial probe, and the third-dimension spatial probe; and (2) a sequence corresponding to the target molecule. Exemplary probe designs and resulting hybridization complexes for generating a product (e.g., a ligation product and/or an extension product) are illustrated in FIGS. 3-8.

Next, the sequence of the product can be determined, thereby identifying the location of the target molecule in a three-dimensional space in the biological sample. In an example, the product(s) can be isolated from the sample prior to determining the sequence of the product. A library is constructed using the products. The product(s) can be sequenced using any available sequencing platform. In some examples, the product comprises a functional sequence that may be used in subsequent processing. For example, the functional sequence may include one or more of a sequencer specific flow cell attachment sequence (e.g., a P5 and/or P7 sequence for Illumina® sequencing systems) and a sequencing primer sequence (e.g., an R1 and/or R2 primer for Illumina® sequencing systems). In some examples, the product can be attached to one or more functional sequence that can be used in subsequent processing according to standard sequencing workflows.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for three-dimensional analysis of a biological sample, comprising:
 (a) in a first dimension, electrophoretically migrating a first population of spatial probes into the biological sample, wherein the first population of spatial probes comprises a first-dimension spatial probe that is targeted to a target molecule immobilized in the biological sample;
 (b) in a second dimension, electrophoretically migrating a second population of spatial probes into the biological sample, wherein the second population of spatial probes comprises a second-dimension spatial probe that is targeted to the target molecule or the first-dimension spatial probe targeted thereto;
 (c) in a third dimension, electrophoretically migrating a third population of spatial probes into the biological sample, wherein the third population of spatial probes comprises a third-dimension spatial probe that is targeted to the target molecule, the first-dimension spatial probe targeted thereto, or the second-dimension spatial probe targeted thereto,
 wherein the first-dimension spatial probe comprises:
  a targeting domain that binds directly or indirectly to the target molecule, and
 wherein each probe of the first population, the second population, and the third population of spatial probes comprises:
  (i) a migration domain corresponding to a location in the biological sample to which the respective spatial probe is migrated in the respective dimension, wherein the migration domain is a variable-length sequence that varies in length between at least one other probe of the respective population of spatial probes, and
  (ii) a migration barcode sequence that identifies the migration domain of the respective spatial probe,
  wherein the migration barcode sequence of each spatial probe of the first population, the second population, and the third population of spatial probes identifies the length of the respective spatial probe and/or the length of the migration domain of the respective spatial probe;
 (d) generating a product in the biological sample, the product comprising:
  (1) a sequence or complement thereof of the migration barcode sequence of the first-dimension spatial probe, a sequence or complement thereof of migration barcode sequence of the second-dimension spatial probe, and a sequence or complement thereof of the migration barcode sequence of the third-dimension spatial probe; and
  (2) a sequence corresponding to the target molecule; and
 (e) determining a sequence of the product, thereby identifying a location of the target molecule in a three-dimensional space in the biological sample;
 wherein the method further comprises ceasing electrophoretic migration after each of steps (a), (b), and (c) to allow spatial probes of the first population, the second population, and the third population to directly or indirectly bind to target molecules at locations to which they are migrated in the biological sample.

2. The method of claim 1, wherein the second-dimension spatial probe comprises a targeting domain for binding to the target molecule and the third-dimension spatial probe comprises a targeting domain for binding to the target molecule.

3. The method of claim 1, wherein the first, second, and/or third populations of spatial probes comprise spatial probes targeting different target molecules.

4. The method of claim 1, wherein the migration domain of each spatial probe is cleavable from its respective spatial probe.

5. The method of claim 1, wherein the method further comprises anchoring the first-, second-, and/or third-dimension spatial probes in the corresponding locations to which they are migrated in the biological sample.

6. The method of claim 5, wherein:
 i) the first-dimension spatial probes are anchored to target molecules and/or other endogenous or exogenous molecules in the corresponding locations to which they are migrated in the biological sample; and/or
 ii) the second- and/or third-dimension spatial probes are anchored to target molecules, previously migrated spatial probe molecules, and/or other endogenous or exogenous molecules in the corresponding locations to which they are migrated in the biological sample.

7. The method of claim 6, wherein the anchoring comprises hybridization, ligation, primer extension, crosslinking, or any combination thereof in any order.

8. The method of claim 1, wherein step (d) comprises joining the sequence or complement thereof of the migration barcode sequences of the first-dimension spatial probe, the second-dimension spatial probe, and the third-dimension spatial probe to the sequence corresponding to the target molecule by ligation or extension to generate the product.

9. The method of claim 1, wherein the method further comprises releasing, removing, or isolating the product from the biological sample prior to the determining step of (e).

10. The method of claim 9, wherein the released, removed, or isolated product is sequenced using sequencing by synthesis, sequencing by ligation, sequencing by hybridization, sequencing by binding, nanopore sequencing, solid-state sequencing, electronic sequencing, digital sequencing, or any combination thereof in any order.

11. The method of claim 1, wherein the target molecule comprises a primary probe that directly or indirectly binds to an analyte in the biological sample or is a product of an endogenous molecule in the biological sample generated using the primary probe prior to step (a).

12. The method of claim 1, wherein the biological sample is embedded in a matrix prior to step (a).

13. The method of claim 12, wherein the target molecule in the biological sample is covalently anchored to the matrix.

14. A method for three-dimensional analysis of a biological sample, comprising:
  (a) generating a target nucleic acid molecule in the biological sample, wherein the target nucleic acid molecule is (i) a product of an endogenous nucleic acid molecule, (ii) a product of one or more nucleic acid probes that directly or indirectly hybridize to the endogenous nucleic acid molecule or to the product of (i), or (iii) a product of the product of (i) or (ii);
  (b) embedding the biological sample in a matrix to form a matrix-embedded biological sample, wherein the target nucleic acid molecule is crosslinked to the matrix, thereby immobilizing the target nucleic acid molecule in the matrix-embedded biological sample;
  (c) electrophoresis a first population of spatial probes for distribution by size in a first dimension, wherein the first population of spatial probes comprises a first-dimension spatial probe that is targeted to the target nucleic acid molecule immobilized in the matrix-embedded biological sample;
  (d) electrophoresis a second population of spatial probes for distribution by size in a second dimension, wherein the second population of spatial probes comprises a second-dimension spatial probe that is targeted to the target nucleic acid molecule or the first-dimension spatial probe targeted thereto;
  (e) electrophoresis a third population of spatial probes for distribution by size in a third dimension, wherein the third population of spatial probes comprises a third-dimension spatial probe that is targeted to the target nucleic acid molecule, the first-dimension spatial probe targeted thereto, or the second-dimension spatial probe targeted thereto, wherein each probe of the first population, the second population, and the third population of spatial probes comprises:
    (i) a targeting sequence for targeting,
    (ii) a variable-length sequence corresponding to a location in the matrix-embedded biological sample to which the respective spatial probe is migrated in the respective dimension, wherein the variable-length sequence varies in length between at least one other probe of the respective population of spatial probes, and
    (iii) a length-barcode sequence corresponding to the variable-length sequence, wherein the length-barcode sequence of each spatial probe of the first population, the second population, and the third population of spatial probes identifies the length of the respective spatial probe and/or the length of the variable-length sequence;
  (f) generating a product in the matrix-embedded biological sample, the product comprising:
    (1) a sequence or complement thereof of the length-barcode sequences of the first-dimension spatial probe, a sequence or complement thereof of the length-barcode of the second-dimension spatial probe, and a sequence or complement thereof of the length-barcode of the third-dimension spatial probe; and
    (2) a sequence or complement thereof of the target nucleic acid molecule;
  (g) releasing, removing, or isolating the product from the matrix-embedded biological sample; and
  (h) subjecting the released, removed, or isolated product to nucleic acid sequencing, thereby identifying a location of the target nucleic acid molecule in the first dimension, the second dimension, and the third dimension of the matrix-embedded biological sample;
  wherein the method further comprises ceasing electrophoretic migration after each of steps (c), (d), and (e) to allow spatial probes of the first population, the second population, and the third population to directly or indirectly bind to target molecules locations to which they are migrated in the biological sample.

15. The method of claim 14, wherein step (a) comprises contacting biological sample with a primary probe that directly or indirectly binds to an analyte in the biological sample and the target nucleic acid molecule comprises the primary probe or a product generated using the primary probe.

16. The method of claim 1, wherein the product generated in (d) comprises a sequence of complement thereof of the migration domain of the first-dimension spatial probe, a sequence of complement thereof of the migration domain of the second-dimension spatial probe, and a sequence or complement thereof of the migration domain of the third-dimension spatial probe.

* * * * *